US006692919B1

(12) United States Patent
Artavanis-Tsakonas et al.

(10) Patent No.: US 6,692,919 B1
(45) Date of Patent: Feb. 17, 2004

(54) ACTIVATED FORMS OF NOTCH AND METHODS BASED THEREON

(75) Inventors: Spyridon Artavanis-Tsakonas, Hamden, CT (US); Huilin Qi, Branford, CT (US); Matthew D. Rand, Branford, CT (US)

(73) Assignee: Yale University, New Haven, CT (US)

( * ) Notice: Subject to any disclaimer, the term of this patent is extended or adjusted under 35 U.S.C. 154(b) by 0 days.

(21) Appl. No.: 09/121,457

(22) Filed: Jul. 23, 1998

Related U.S. Application Data

(63) Continuation-in-part of application No. 08/899,232, filed on Jul. 23, 1997, now Pat. No. 6,436,650.

(51) Int. Cl.$^7$ ..................... G01N 33/53; G01N 33/567; G01N 33/574; A61K 38/00; C07K 16/00
(52) U.S. Cl. ................. 435/7.1; 435/7.2; 435/7.23; 530/320; 530/324
(58) Field of Search .................. 435/7.1, 7.2, 7.23; 530/320, 324

(56) References Cited

U.S. PATENT DOCUMENTS

| | | | |
|---|---|---|---|
| 5,637,471 A | 6/1997 | Artavanis-Tsakonas et al. | 435/7.23 |
| 5,648,464 A | 7/1997 | Artavanis-Tsakonas et al. | 530/350 |
| 5,750,652 A | 5/1998 | Artavanis-Tsakonas et al. | 530/350 |
| 5,780,300 A | 7/1998 | Artavanis-Tsakonas et al. | 435/372 |
| 5,786,158 A | 7/1998 | Artavanis-Tsakonas et al. | 435/7.23 |
| 5,789,195 A | 8/1998 | Artavanis-Tsakonas et al. | 435/67.1 |

FOREIGN PATENT DOCUMENTS

| | | |
|---|---|---|
| WO | WO 92/19734 | 11/1992 |
| WO | WO 93/12141 | 6/1993 |
| WO | WO 93/20242 | 10/1993 |
| WO | WO 94/07474 | 4/1994 |
| WO | WO 94/07522 | 4/1994 |
| WO | WO 94/08037 | 4/1994 |
| WO | WO 94/11401 | 5/1994 |
| WO | WO 95/19779 | 7/1995 |
| WO | WO 96/27610 | 9/1996 |
| WO | WO 97/01571 | 1/1997 |
| WO | WO 97/11716 | 4/1997 |
| WO | WO 97/18822 | 5/1997 |
| WO | WO 97/19172 | 5/1997 |

OTHER PUBLICATIONS

Adams et al., 1993, "3,400 new expressed sequence tags identify diversity of transcripts in human brain", Nature Genetics 4:256–267.

Ahmad et al., 1995, "Involvement of Notch–1 in mammalian retinal neurogenesis: Association of Notch–1 activity with both immature and terminally differentiation cells", Mechanisms of Development 53:78–85.
Artavanis–Tsakonas et al., 1995, "Notch signaling", Science 268;255–232.
Aster et al., 1994, "Functional analysis of the Tan–1 gene, a human homolog of drosophila notch", Cold Spring Harbor Symposia on Quantitative Biology 59:125–136.
Baker & Schubiger, 1996, "Autonomous and non–autonomous Notch functions for embryonic muscle and epidermis development in drosophila", Development 122:617–626.
Bierkamp et al., 1993, "A zebrafish homologue of the Drosophila neurogenic gene Notch and its pattern of transcription during early embryogenesis", Mech. Dev. 43:87–100.
Blaumueller & Artavanis–Tsakonas, 1997, "Comparative aspects of notch signalling in lower and higher eukaryotes", Perp. on Dev. Neurobiol. 4:325–343.
Brou et al., 1994, "Inhibition of the DNA–binding activity of Drosophila suppressor of hairless and its human homolog, KBF2/RBP–Jk, by direct protein–protein interaction with drosophila hairless", Genes Dev. 8:2491.
Coffman et al., 1993, "Expression of an extracellular deletion of Xotch diverts fate in Xenopus embryos", Cell 73:659.
Coffman et al., 1990, "Xotch, the xenopus homolog of drosophila notch", Science 249:1438–1441.
Delidakis et al., 1991, "Two genetically and molecularly distinct functions involved in early neurogenesis reside within the enhancer of split locus of drosophila melanogaster", Genetics 129:803.
Ellison et al., 1991, "TAN–1, the human homolog of the drosophila notch gene, is broken by chromosomal translocations in T lymphoblastic neoplasms", Cell 66:649–661.

(List continued on next page.)

*Primary Examiner*—Yvonne Eyler
*Assistant Examiner*—Janet L. Andres
(74) *Attorney, Agent, or Firm*—Pennie & Edmonds LLP

(57) ABSTRACT

The present invention is directed to methods for detecting or measuring Notch activation by observing or measuring the appearance of Notch on the cell surface or by observing or measuring Notch cleavage products that are indicative of Notch activation. The present invention is also directed to methods for detecting a molecule that modulates Notch activation by observing or measuring a change in the amount of Notch expressed on the cell surface or a change in the amount or pattern of Notch cleavage products. The present invention is also directed to a substantially purified activated heterodimeric form of Notch and components thereof and pharmaceutical compositions and kits thereof. The present invention is based, at least in part, on the discovery that Notch in its active form, i.e., the form that mediates signal transduction and that binds Notch ligands such as Delta, is a heterodimer of an about 180 kDa subunit ($N^{EC}$) and an about 110 kDa subunit ($N^{TM}$), which are tethered together through a reducing agent-sensitive linkage, in particular, a non-covalent, metal ion-dependent linkage.

6 Claims, 17 Drawing Sheets

OTHER PUBLICATIONS

Figure 1:
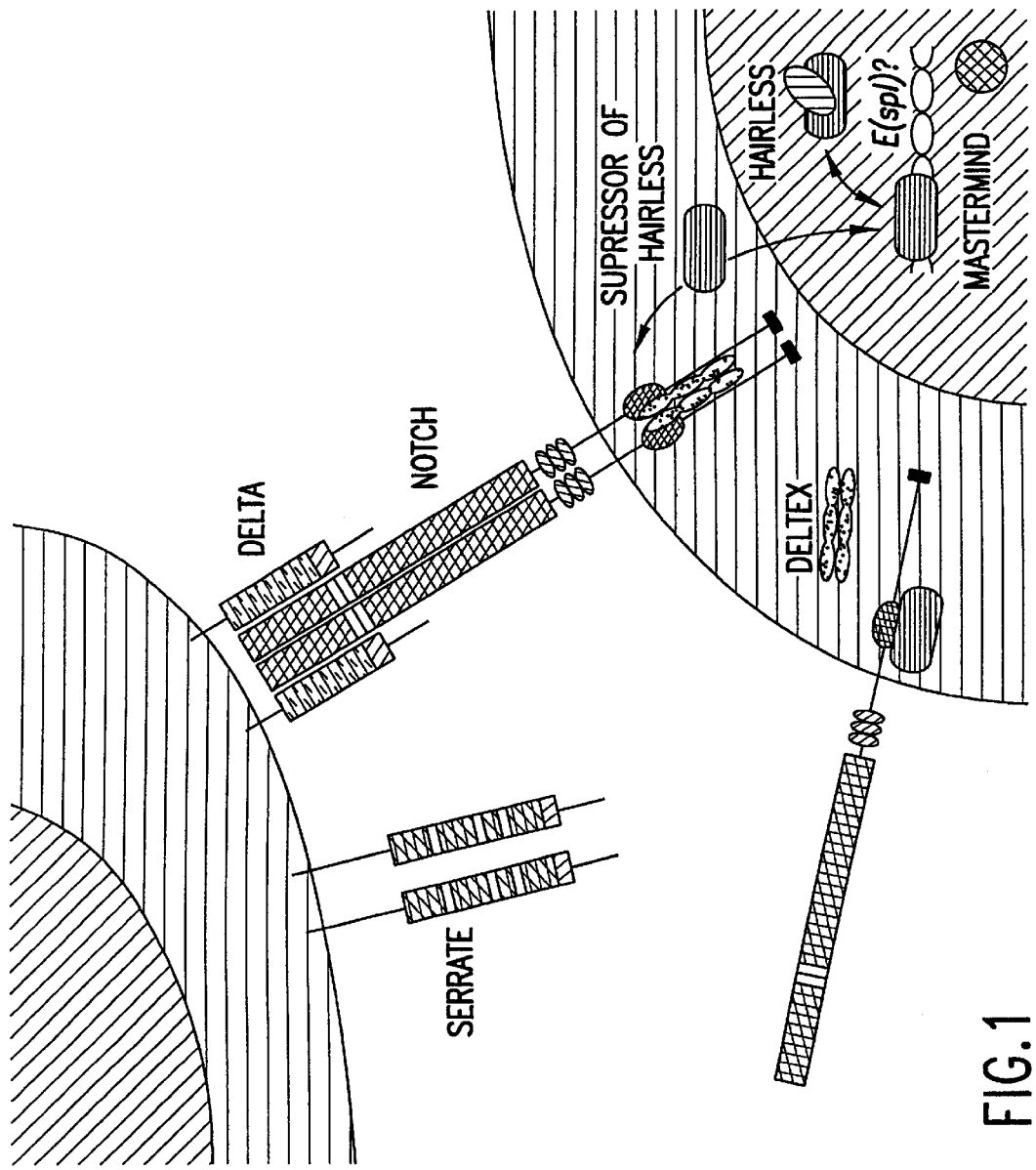

Fehon et al., 1990, "Molecular interactions between the protein products of the neurogenic loci notch and delta, two EGF–homologous genes in drosophila", Cell 61:523–534.

Fortini & Artavanis–Tsakonas, 1994, "Notch: neurogenesis is only part of the picture", Cell 75:1245–1247.

Fortini & Artavanis–Tsakonas, 1994, "The suppressor of hairless protein participates in notch receptor signalling", Cell 79:273–282.

Fortini et al., 1993, "An activated Notch receptor blocks cell–fate commitment in the developing drosophila eye", Nature 365:555–557.

Foster, 1975, "Negative complementation at the notch locus of drosophila melanogaster", Genetics 81:99–120.

Franco del Amo et al., 1992, "Expression pattern of Motch, a mouse homolog of drosophila notch, suggests an important role in early postimplantation mouse development", Development 115:737–744.

Genhring W., 1973, In genetic mechanisms of development: the 31st symposium of the society for developmental biology, ed by Ruddle F, New York: Academic Press Inc.:pp. 103–125.

Greenwald, 1994, "Structure/function studies of lin–12/notch proteins", Current Opinions in Genetics and Development 4:556–562.

Heitzler and Simpson, 1991, "The choice of cell fate in the epidermis of drosophila", Cell 64:1083–1092.

Henrique et al., 1995, "Expression of a delta homologue in prospective neurons in the chick", Nature 375:787–790.

Hoppe & Greenspan, 1990, "The notch locus of drosophila is required in epidermal cells for development", Dev. 109:875–885.

Horvitz et al., 1991, "Multiple intercellular signalling systems control the development of the *Caenorhabditis elegans* vulva", Nature 351:535–541.

Jan et al., 1993, "Functional gene cassettes in development", PNAS USA 90:8305–8307.

Jennings et al., 1994, "The notch signalling pathway is required for enhancer of split bHLH protein expression during neurogenesis in the Drosophila embryo", Development 120:3537–3548.

Knust et al., 1992, "Seven Genes of the Enhancer of split complex of *Drosophila melanogaster* encode helix–loop–helix proteins", Genetics 132:505–518.

Kooh et al., 1993, "Implications of dynamic patterns of Delta and Notch expression for cellular interactions during drosophila development", Development 117:493–507.

Kopan et al., 1996, "Signal transduction by activated mNotch: importance of proteolytic processing and its regulation by the extracellular domain", PNAS USA 93(4):1683–1688.

Kopan et al., 1994, "The intracellular domain of mouse Notch" a constitutively activated repressor of myogenesis directed at the basic helix–loop–helix region of MyoD, Development 120:2385–2396.

Kopan et al., 1993, "Mouse Notch: expression in hair follicles correlates with cell fate determination", J. Cell. Biol. 121:631–641.

Lardelli et al., 1994, "The novel Notch homologue mouse Notch 3 lacks specific epidermal growth factor–repeats and is expressed in proliferating neuroepithelium", Mech. Dev. 46:123–136.

Lardelli et al., 1993, "Motch A and motch B–two mouse Notch homologues coexpressed in a wide variety of tissues", Exp. Cell. Res. 204:364–372.

Larsson et al., 1994, "The human NOTCH1, 2, and 3 genes are located at chromosome positions 9q34, 1p13–p11, and 19p13.2–p13.1 in regions of neoplasia–associated translocation", Genomics 24:253–258.

Lieber et al., 1993, "Antineurogenic phenotypes induced by truncated Notch proteins indicate a role in signal transduction and may point to a novel function for Notch in nuclei", Genes and Development 7:1949–1965.

Lyman et al., 1993, "Further evidence for function of the drosophila notch protein as a transmembrane receptor", PNAS USA 90:10395–10399.

Mango et al., 1994, "Two maternal genes, apx–1 and pie–1 are required to distinguish the fates equivalent blastomeres in the early *Caenorabditis elegans* embryo", Development 120:2305–2315.

Mango et al., 1991, "Carboxy–terminal truncation activates glp–1 protein to specify vulval fates in *Caeorhabditis elegans*", Nature 352:811–815.

Markopoulou et al., 1990, "Developmental analysis of the facets, a group of intronic mutations at the notch locus of *Drosophila melanogaster* that affect postembryonic development", J. Exper. Zool. 27:23–27.

Matsuno et al., 1995, "Deltex acts as a positive regulator of Notch signalling through interactions with the Notch ankyrin repeats", Development 121:2633–2644.

Mello et al., 1994, "The maternal genes apx–1 and glp–1 and establishment of Dorsal–ventral polarity in the early *C. elegans* embryo", Cell 77:95–106.

Nusse & Varmus, 1992, "Wnt genes", 69(7):1073–87.

Reaume et al., 1992, "Expression Analysis of a Notch Homologue in the Mouse Embryo", Dev. Biol. 154:37/7–387.

Rebay et al., 1991, "Specific EGF repeats of Notch mediate interactions with delta and serrate: implications for notch as a multi–functional receptor", Cell 67:687–699.

Roehl et al., 1993, "Control of cell fate in *C. elegans* by a GLP–1 peptide consisting primarily of ankyrin repeats", Nature 364:632.

Simske et al., 1995, Nature 375:142–145.

Smoller et al., 1990, "The drosophila neurogenic locus mastermind encodes a nuclear protein unusually rich in amino acid homopolymers", Genes Dev. 4:1688.

Sternberg, 1993, "Falling off the knife edge", Current Biology 3:763–765.

Stifani et al., 1992, "Human homologs of a drosophila enhancer of split gene product define a novel family of nuclear proteins" Nature Genetics 2:119–127.

Struhl & Basler, 1993, "Organizing activity of Wingless Protein in Drosophila", Cell 74:527–540.

Struhl et al., 1993,"Intrinsic activity of the Lin–12 and notch intracellular domains in vivo", Cell 74:331.

Swiatek et al., 1994, "Notch1 is essential for postimplantation development in mice", Genes Dev. 8:707.

Sun & Artavanis–Tsakonas, 1996, "The intracellular deletions of DELTA and SERRATE define dominant negative forms if the drosophila notch ligands", Development 122:2465–2474.

Technau et al., 1987, "Cell autonomy of expression of neurogenic genes *Drosophila melanogaster*" PNAS USA 84:4500–4504.

Weinmaster et al., 1992, "Notch2: a second mammalian Notch gene", Development 116:931–941.

Weinmaster et al., 1991, "A homolog of drosophila Notch expressed during mammalian development", Development 113:199–205.

Wharton et al., 1985, "Nucleotide sequence from the neurogenic locus Notch implies a gene product that shares homology with proteins containing EGF–like repeats", Cell 43:567–581.

Xu et al., 1990, "The notch locus and the genetic circuitry involved in early drosophila neurogenesis", Genes Dev. 4:464–475.

Zagouras et al., 1995, "Alterations in Notch signalling in neoplastic lesions of the human cervix", PNAS USA 92:6414–6418.

Logeat et al., 1998, "The notch1 receptor is cleaved constitutively by a furin–like convertase", PNAS 95:8108–8112.

Schroeter et al., 1998, "The Notch–1 signalling requires ligand–induced proteolytic release of intracellular domain", Nature 393:382–386.

Rebay et al., 1993, "Specific truncations of Drosophila Notch define dominant activated and dominant negative forms of the receptor", Cell 74(2):319–329.

Johansen et al., 1989, J. Cell. Biol. 109:2427–2440; The Notch Gene Product is a Glycoprotein Expressed on the Outer Surface of Both Epidermal and Neuronal Precursor Cells during Drosophila Development.

Blaumueller et al., 1997, Cell 90:281–291; Intracellular Cleavage of Notch Leads to a Heterodimeric Receptor on the Plasma Membrane.

Fleming et al., 1997, Trends in Cell Biology 7:437–441; The NOTCH Receptor and its Ligands.

Wesley, 1999, Mol. Cell Biol. 19(8):5743–5758.

Wesley and Saez, 2000, J. Cell Biol. 149(3):683–696.

Qi et al., 1999, Science 283:91–94.

Sestan et al., 1999, Science 286:741–746.

Lindsell et al., 1995, Cell 80:909–917.

Nye et al., 1994, Development 120:2421–2430.

Robey et al., 1996, "An Activated Form of Notch Influences the Choice between CD4 and CD8 T Cell Lineages", Cell 87:483–492.

Washburn et al., 1997, "Notch Activity Influences the $\alpha\beta$ versus $\gamma\delta$ T Cell Lineage Decision", Cell 88:833–843.

Pui et al., 1999, "Notch1 Expression in Early Lymphopoiesis Influences B Versus T Lineage Determination", Immunity 11:299–308.

Joutel et al., 1996, "Notch3 mutatons in CADASIL, a hereditary adult–onset condition causing stroke and dementia", Nature 383:707–711.

ODA et al., 1997, "Mutations in the Human Jagged1 Gene are Responsible for Alagille Syndrome", Nature Genetics 16:235–242.

Li et al., 1997, "Alagille Syndrome is caused by mutations in human Jaggeed1, which encodes a ligand for Notch 1", 16:243–251.

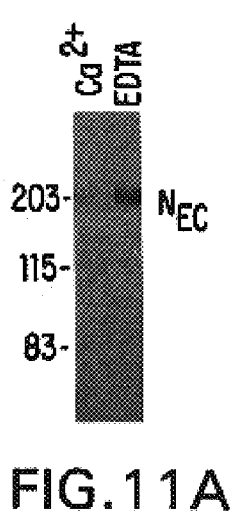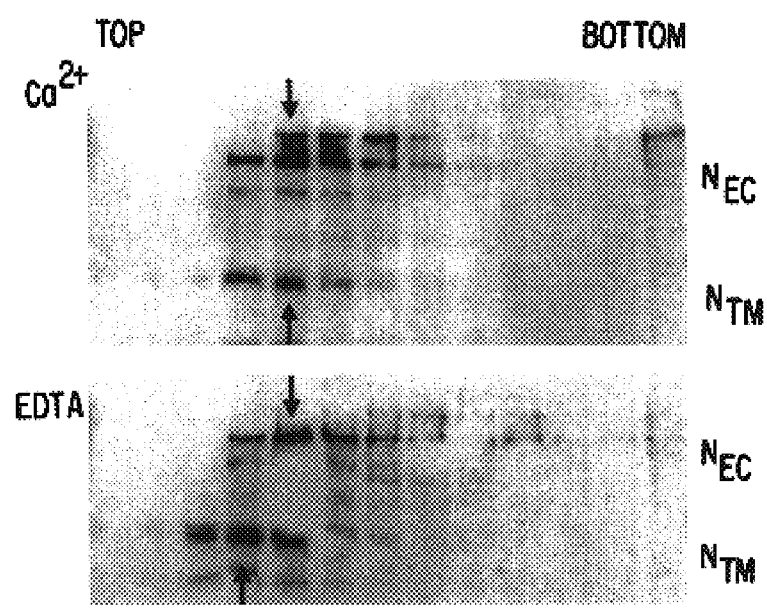
FIG.11A
FIG.11B

SEQUENCE LISTING

<160> NUMBER OF SEQ ID NOS: 4

<210> SEQ ID NO 1
<211> LENGTH: 2471
<212> TYPE: PRT
<213> ORGANISM: Homo sapiens

<400> SEQUENCE: 1

```
Met Pro Ala Leu Arg Pro Ala Leu Leu Trp Ala Leu Leu Ala Leu Trp
  1               5                  10                  15

Leu Cys Cys Ala Ala Pro Ala His Ala Leu Gln Cys Arg Asp Gly Tyr
             20                  25                  30

Glu Pro Cys Val Asn Glu Gly Met Cys Val Thr Tyr His Asn Gly Thr
         35                  40                  45

Gly Tyr Cys Lys Cys Pro Glu Gly Phe Leu Gly Glu Tyr Cys Gln His
     50                  55                  60

Arg Asp Pro Cys Glu Lys Asn Arg Cys Gln Asn Gly Gly Thr Cys Val
 65                  70                  75                  80

Ala Gln Ala Met Leu Gly Lys Ala Thr Cys Arg Cys Ala Ser Gly Phe
                 85                  90                  95

Thr Gly Glu Asp Cys Gln Tyr Ser Thr Ser His Pro Cys Phe Val Ser
            100                 105                 110

Arg Pro Cys Leu Asn Gly Gly Thr Cys His Met Leu Ser Arg Asp Thr
        115                 120                 125

Tyr Glu Cys Thr Cys Gln Val Gly Phe Thr Gly Lys Glu Cys Gln Trp
    130                 135                 140

Thr Asp Ala Cys Leu Ser His Pro Cys Ala Asn Gly Ser Thr Cys Thr
145                 150                 155                 160

Thr Val Ala Asn Gln Phe Ser Cys Lys Cys Leu Thr Gly Phe Thr Gly
                165                 170                 175

Gln Lys Cys Glu Thr Asp Val Asn Glu Cys Asp Ile Pro Gly His Cys
            180                 185                 190

Gln His Gly Gly Thr Cys Leu Asn Leu Pro Gly Ser Tyr Gln Cys Gln
        195                 200                 205

Cys Pro Gln Gly Phe Thr Gly Gln Tyr Cys Asp Ser Leu Tyr Val Pro
    210                 215                 220

Cys Ala Pro Ser Pro Cys Val Asn Gly Gly Thr Cys Arg Gln Thr Gly
225                 230                 235                 240

Asp Phe Thr Phe Glu Cys Asn Cys Leu Pro Gly Phe Glu Gly Ser Thr
                245                 250                 255

Cys Glu Arg Asn Ile Asp Asp Cys Pro Asn His Arg Cys Gln Asn Gly
            260                 265                 270

Gly Val Cys Val Asp Gly Val Asn Thr Tyr Asn Cys Arg Cys Pro Pro
        275                 280                 285

Gln Trp Thr Gly Gln Phe Cys Thr Glu Asp Val Asp Glu Cys Leu Leu
```

```
            290                 295                 300
Gln Pro Asn Ala Cys Gln Asn Gly Gly Thr Cys Ala Asn Arg Asn Gly
305                 310                 315                 320

Gly Tyr Gly Cys Val Cys Val Asn Gly Trp Ser Gly Asp Asp Cys Ser
                325                 330                 335

Glu Asn Ile Asp Asp Cys Ala Phe Ala Ser Cys Thr Pro Gly Ser Thr
                340                 345                 350

Cys Ile Asp Arg Val Ala Ser Phe Ser Cys Met Cys Pro Glu Gly Lys
                355                 360                 365

Ala Gly Leu Leu Cys His Leu Asp Asp Ala Cys Ile Ser Asn Pro Cys
370                 375                 380

His Lys Gly Ala Leu Cys Asp Thr Asn Pro Leu Asn Gly Gln Tyr Ile
385                 390                 395                 400

Cys Thr Cys Pro Gln Gly Tyr Lys Gly Ala Asp Cys Thr Glu Asp Val
                405                 410                 415

Asp Glu Cys Ala Met Ala Asn Ser Asn Pro Cys Glu His Ala Gly Lys
                420                 425                 430

Cys Val Asn Thr Asp Gly Ala Phe His Cys Glu Cys Leu Lys Gly Tyr
                435                 440                 445

Ala Gly Pro Arg Cys Glu Met Asp Ile Asn Glu Cys His Ser Asp Pro
450                 455                 460

Cys Gln Asn Asp Ala Thr Cys Leu Asp Lys Ile Gly Gly Phe Thr Cys
465                 470                 475                 480

Leu Cys Met Pro Gly Phe Lys Gly Val His Cys Glu Leu Glu Ile Asn
                485                 490                 495

Glu Cys Gln Ser Asn Pro Cys Val Asn Asn Gly Gln Cys Val Asp Lys
                500                 505                 510

Val Asn Arg Phe Gln Cys Leu Cys Pro Pro Gly Phe Thr Gly Pro Val
                515                 520                 525

Cys Gln Ile Asp Ile Asp Asp Cys Ser Ser Thr Pro Cys Leu Asn Gly
                530                 535                 540

Ala Lys Cys Ile Asp His Pro Asn Gly Tyr Glu Cys Gln Cys Ala Thr
545                 550                 555                 560

Gly Phe Thr Gly Val Leu Cys Glu Glu Asn Ile Asp Asn Cys Asp Pro
                565                 570                 575

Asp Pro Cys His His Gly Gln Cys Gln Asp Gly Ile Asp Ser Tyr Thr
                580                 585                 590

Cys Ile Cys Asn Pro Gly Tyr Met Gly Ala Ile Cys Ser Asp Gln Ile
                595                 600                 605

Asp Glu Cys Tyr Ser Ser Pro Cys Leu Asn Asp Gly Arg Cys Ile Asp
                610                 615                 620

Leu Val Asn Gly Tyr Gln Cys Asn Cys Gln Pro Gly Thr Ser Gly Val
625                 630                 635                 640

Asn Cys Glu Ile Asn Phe Asp Asp Cys Ala Ser Asn Pro Cys Ile His
                645                 650                 655

Gly Ile Cys Met Asp Gly Ile Asn Arg Tyr Ser Cys Val Cys Ser Pro
                660                 665                 670

Gly Phe Thr Gly Gln Arg Cys Asn Ile Asp Ile Asp Glu Cys Ala Ser
                675                 680                 685

Asn Pro Cys Arg Lys Gly Ala Thr Cys Ile Asn Gly Val Asn Gly Phe
                690                 695                 700

Arg Cys Ile Cys Pro Glu Gly Pro His His Pro Ser Cys Tyr Ser Gln
705                 710                 715                 720
```

-continued

```
Val Asn Glu Cys Leu Ser Asn Pro Cys Ile His Gly Asn Cys Thr Gly
            725                 730                 735
Gly Leu Ser Gly Tyr Lys Cys Leu Cys Asp Ala Gly Trp Val Gly Ile
            740                 745                 750
Asn Cys Glu Val Asp Lys Asn Glu Cys Leu Ser Asn Pro Cys Gln Asn
            755                 760                 765
Gly Gly Thr Cys Asp Asn Leu Val Asn Gly Tyr Arg Cys Thr Cys Lys
            770                 775                 780
Lys Gly Phe Lys Gly Tyr Asn Cys Gln Val Asn Ile Asp Glu Cys Ala
785                 790                 795                 800
Ser Asn Pro Cys Leu Asn Gln Gly Thr Cys Phe Asp Asp Ile Ser Gly
            805                 810                 815
Tyr Thr Cys His Cys Val Leu Pro Tyr Thr Gly Lys Asn Cys Gln Thr
            820                 825                 830
Val Leu Ala Pro Cys Ser Pro Asn Pro Cys Glu Asn Ala Ala Val Cys
            835                 840                 845
Lys Glu Ser Pro Asn Phe Glu Ser Tyr Thr Cys Leu Cys Ala Pro Gly
            850                 855                 860
Trp Gln Gly Gln Arg Cys Thr Ile Asp Ile Asp Glu Cys Ile Ser Lys
865                 870                 875                 880
Pro Cys Met Asn His Gly Leu Cys His Asn Thr Gln Gly Ser Tyr Met
            885                 890                 895
Cys Glu Cys Pro Pro Gly Phe Ser Gly Met Asp Cys Glu Glu Asp Ile
            900                 905                 910
Asp Asp Cys Leu Ala Asn Pro Cys Gln Asn Gly Gly Ser Cys Met Asp
            915                 920                 925
Gly Val Asn Thr Phe Ser Cys Leu Cys Leu Pro Gly Phe Thr Gly Asp
930                 935                 940
Lys Cys Gln Thr Asp Met Asn Glu Cys Leu Ser Glu Pro Cys Lys Asn
945                 950                 955                 960
Gly Gly Thr Cys Ser Asp Tyr Val Asn Ser Tyr Thr Cys Lys Cys Gln
            965                 970                 975
Ala Gly Phe Asp Gly Val His Cys Glu Asn Asn Ile Asn Glu Cys Thr
            980                 985                 990
Glu Ser Ser Cys Phe Asn Gly Gly Thr Cys Val Asp Gly Ile Asn Ser
            995                 1000                1005
Phe Ser Cys Leu Cys Pro Val Gly Phe Thr Gly Ser Phe Cys Leu His
    1010                1015                1020
Glu Ile Asn Glu Cys Ser Ser His Pro Cys Leu Asn Glu Gly Thr Cys
1025                1030                1035                1040
Val Asp Gly Leu Gly Thr Tyr Arg Cys Ser Cys Pro Leu Gly Tyr Thr
                1045                1050                1055
Gly Lys Asn Cys Gln Thr Leu Val Asn Leu Cys Ser Arg Ser Pro Cys
                1060                1065                1070
Lys Asn Lys Gly Thr Cys Val Gln Lys Lys Ala Glu Ser Gln Cys Leu
            1075                1080                1085
Cys Pro Ser Gly Trp Ala Gly Ala Tyr Cys Asp Val Pro Asn Val Ser
    1090                1095                1100
Cys Asp Ile Ala Ala Ser Arg Arg Gly Val Leu Val Glu His Leu Cys
1105                1110                1115                1120
Gln His Ser Gly Val Cys Ile Asn Ala Gly Asn Thr His Tyr Cys Gln
            1125                1130                1135
```

-continued

```
Cys Pro Leu Gly Tyr Thr Gly Ser Tyr Cys Glu Glu Gln Leu Asp Glu
        1140                1145                1150

Cys Ala Ser Asn Pro Cys Gln His Gly Ala Thr Cys Ser Asp Phe Ile
    1155                1160                1165

Gly Gly Tyr Arg Cys Glu Cys Val Pro Gly Tyr Gln Gly Val Asn Cys
1170                1175                1180

Glu Tyr Glu Val Asp Glu Cys Gln Asn Gln Pro Cys Gln Asn Gly Gly
1185                1190                1195                1200

Thr Cys Ile Asp Leu Val Asn His Phe Lys Cys Ser Cys Pro Pro Gly
            1205                1210                1215

Thr Arg Gly Leu Leu Cys Glu Glu Asn Ile Asp Asp Cys Ala Arg Gly
        1220                1225                1230

Pro His Cys Leu Asn Gly Gly Gln Cys Met Asp Arg Ile Gly Gly Tyr
    1235                1240                1245

Ser Cys Arg Cys Leu Pro Gly Phe Ala Gly Glu Arg Cys Glu Gly Asp
1250                1255                1260

Ile Asn Glu Cys Leu Ser Asn Pro Cys Ser Ser Glu Gly Ser Leu Asp
1265                1270                1275                1280

Cys Ile Gln Leu Thr Asn Asp Tyr Leu Cys Val Cys Arg Ser Ala Phe
            1285                1290                1295

Thr Gly Arg His Cys Glu Thr Phe Val Asp Val Cys Pro Gln Met Pro
        1300                1305                1310

Cys Leu Asn Gly Gly Thr Cys Ala Val Ala Ser Asn Met Pro Asp Gly
    1315                1320                1325

Phe Ile Cys Arg Cys Pro Pro Gly Phe Ser Gly Ala Arg Cys Gln Ser
1330                1335                1340

Ser Cys Gly Gln Val Lys Cys Arg Lys Gly Glu Gln Cys Val His Thr
1345                1350                1355                1360

Ala Ser Gly Pro Arg Cys Phe Cys Pro Ser Pro Arg Asp Cys Glu Ser
            1365                1370                1375

Gly Cys Ala Ser Ser Pro Cys Gln His Gly Gly Ser Cys His Pro Gln
        1380                1385                1390

Arg Gln Pro Pro Tyr Tyr Ser Cys Gln Cys Ala Pro Pro Phe Ser Gly
    1395                1400                1405

Ser Arg Cys Glu Leu Tyr Thr Ala Pro Pro Ser Thr Pro Pro Ala Thr
1410                1415                1420

Cys Leu Ser Gln Tyr Cys Ala Asp Lys Ala Arg Asp Gly Val Cys Asp
1425                1430                1435                1440

Glu Ala Cys Asn Ser His Ala Cys Gln Trp Asp Gly Gly Asp Cys Ser
            1445                1450                1455

Leu Thr Met Glu Asn Pro Trp Ala Asn Cys Ser Ser Pro Leu Pro Cys
        1460                1465                1470

Trp Asp Tyr Ile Asn Asn Gln Cys Asp Glu Leu Cys Asn Thr Val Glu
    1475                1480                1485

Cys Leu Phe Asp Asn Phe Glu Cys Gln Gly Asn Ser Lys Thr Cys Lys
1490                1495                1500

Tyr Asp Lys Tyr Cys Ala Asp His Phe Lys Asp Asn His Cys Asn Gln
1505                1510                1515                1520

Gly Cys Asn Ser Glu Glu Cys Gly Trp Asp Gly Leu Asp Cys Ala Ala
            1525                1530                1535

Asp Gln Pro Glu Asn Leu Ala Glu Gly Thr Leu Val Ile Val Val Leu
        1540                1545                1550

Met Pro Pro Glu Gln Leu Leu Gln Asp Ala Arg Ser Phe Leu Arg Ala
```

-continued

```
              1555                1560                1565

Leu Gly Thr Leu Leu His Thr Asn Leu Arg Ile Lys Arg Asp Ser Gln
    1570                1575                1580

Gly Glu Leu Met Val Tyr Pro Tyr Tyr Gly Glu Lys Ser Ala Ala Met
1585                1590                1595                1600

Lys Lys Gln Arg Met Thr Arg Arg Ser Leu Pro Gly Glu Gln Glu Gln
            1605                1610                1615

Glu Val Ala Gly Ser Lys Val Phe Leu Glu Ile Asp Asn Arg Gln Cys
        1620                1625                1630

Val Gln Asp Ser Asp His Cys Phe Lys Asn Thr Asp Ala Ala Ala Ala
    1635                1640                1645

Leu Leu Ala Ser His Ala Ile Gln Gly Thr Leu Ser Tyr Pro Leu Val
1650                1655                1660

Ser Val Val Ser Glu Ser Leu Thr Pro Glu Arg Thr Gln Leu Leu Tyr
1665                1670                1675                1680

Leu Leu Ala Val Ala Val Val Ile Ile Leu Phe Ile Ile Leu Leu Gly
            1685                1690                1695

Val Ile Met Ala Lys Arg Lys Arg Lys His Gly Ser Leu Trp Leu Pro
        1700                1705                1710

Glu Gly Phe Thr Leu Arg Arg Asp Ala Ser Asn His Lys Arg Arg Glu
    1715                1720                1725

Pro Val Gly Gln Asp Ala Val Gly Leu Lys Asn Leu Ser Val Gln Val
    1730                1735                1740

Ser Glu Ala Asn Leu Ile Gly Thr Gly Thr Ser Glu His Trp Val Asp
1745                1750                1755                1760

Asp Glu Gly Pro Gln Pro Lys Lys Val Lys Ala Glu Asp Glu Ala Leu
            1765                1770                1775

Leu Ser Glu Glu Asp Asp Pro Ile Asp Arg Arg Pro Trp Thr Gln Gln
        1780                1785                1790

His Leu Glu Ala Ala Asp Ile Arg Arg Thr Pro Ser Leu Ala Leu Thr
    1795                1800                1805

Pro Pro Gln Ala Glu Gln Glu Val Asp Val Leu Asp Val Asn Val Arg
    1810                1815                1820

Gly Pro Asp Gly Cys Thr Pro Leu Met Leu Ala Ser Leu Arg Gly Gly
1825                1830                1835                1840

Ser Ser Asp Leu Ser Asp Glu Asp Glu Asp Ala Glu Asp Ser Ser Ala
            1845                1850                1855

Asn Ile Ile Thr Asp Leu Val Tyr Gln Gly Ala Ser Leu Gln Ala Gln
        1860                1865                1870

Thr Asp Arg Thr Gly Glu Met Ala Leu His Leu Ala Ala Arg Tyr Ser
    1875                1880                1885

Arg Ala Asp Ala Ala Lys Arg Leu Leu Asp Ala Gly Ala Asp Ala Asn
    1890                1895                1900

Ala Gln Asp Asn Met Gly Arg Cys Pro Leu His Ala Ala Val Ala Ala
1905                1910                1915                1920

Asp Ala Gln Gly Val Phe Gln Ile Leu Ile Arg Asn Arg Val Thr Asp
            1925                1930                1935

Leu Asp Ala Arg Met Asn Asp Gly Thr Thr Pro Leu Ile Leu Ala Ala
        1940                1945                1950

Arg Leu Ala Val Glu Gly Met Val Ala Glu Leu Ile Asn Cys Gln Ala
    1955                1960                1965

Asp Val Asn Ala Val Asp Asp His Gly Lys Ser Ala Leu His Trp Ala
    1970                1975                1980
```

-continued

```
Ala Ala Val Asn Asn Val Glu Ala Thr Leu Leu Leu Lys Asn Gly
1985                1990                1995                2000

Ala Asn Arg Asp Met Gln Asp Asn Lys Glu Glu Thr Pro Leu Phe Leu
        2005                2010                2015

Ala Ala Arg Glu Gly Ser Tyr Glu Ala Ala Lys Ile Leu Leu Asp His
        2020                2025                2030

Phe Ala Asn Arg Asp Ile Thr Asp His Met Asp Arg Leu Pro Arg Asp
        2035                2040                2045

Val Ala Arg Asp Arg Met His His Asp Ile Val Arg Leu Leu Asp Glu
    2050                2055                2060

Tyr Asn Val Thr Pro Ser Pro Pro Gly Thr Val Leu Thr Ser Ala Leu
2065                2070                2075                2080

Ser Pro Val Ile Cys Gly Pro Asn Arg Ser Phe Leu Ser Leu Lys His
                2085                2090                2095

Thr Pro Met Gly Lys Lys Ser Arg Arg Pro Ser Ala Lys Ser Thr Met
            2100                2105                2110

Pro Thr Ser Leu Pro Asn Leu Ala Lys Glu Ala Lys Asp Ala Lys Gly
        2115                2120                2125

Ser Arg Arg Lys Lys Ser Leu Ser Glu Lys Val Gln Leu Ser Glu Ser
    2130                2135                2140

Ser Val Thr Leu Ser Pro Val Asp Ser Leu Glu Ser Pro His Thr Tyr
2145                2150                2155                2160

Val Ser Asp Thr Thr Ser Ser Pro Met Ile Thr Ser Pro Gly Ile Leu
            2165                2170                2175

Gln Ala Ser Pro Asn Pro Met Leu Ala Thr Ala Ala Pro Pro Ala Pro
        2180                2185                2190

Val His Ala Gln His Ala Leu Ser Phe Ser Asn Leu His Glu Met Gln
    2195                2200                2205

Pro Leu Ala His Gly Ala Ser Thr Val Leu Pro Ser Val Ser Gln Leu
        2210                2215                2220

Leu Ser His His His Ile Val Ser Pro Gly Ser Gly Ser Ala Gly Ser
2225                2230                2235                2240

Leu Ser Arg Leu His Pro Val Pro Val Pro Ala Asp Trp Met Asn Arg
            2245                2250                2255

Met Glu Val Asn Glu Thr Gln Tyr Asn Glu Met Phe Gly Met Val Leu
        2260                2265                2270

Ala Pro Ala Glu Gly Thr His Pro Gly Ile Ala Pro Gln Ser Arg Pro
    2275                2280                2285

Pro Glu Gly Lys His Ile Thr Thr Pro Arg Glu Pro Leu Pro Pro Ile
    2290                2295                2300

Val Thr Phe Gln Leu Ile Pro Lys Gly Ser Ile Ala Gln Pro Ala Gly
2305                2310                2315                2320

Ala Pro Gln Pro Gln Ser Thr Cys Pro Pro Ala Val Ala Gly Pro Leu
        2325                2330                2335

Pro Thr Met Tyr Gln Ile Pro Glu Met Ala Arg Leu Pro Ser Val Ala
            2340                2345                2350

Phe Pro Thr Ala Met Met Pro Gln Gln Asp Gly Gln Val Ala Gln Thr
        2355                2360                2365

Ile Leu Pro Ala Tyr His Pro Phe Pro Ala Ser Val Gly Lys Tyr Pro
    2370                2375                2380

Thr Pro Pro Ser Gln His Ser Tyr Ala Ser Ser Asn Ala Ala Glu Arg
2385                2390                2395                2400
```

```
Thr Pro Ser His Ser Gly His Leu Gln Gly Glu His Pro Tyr Leu Thr
            2405                2410                2415

Pro Ser Pro Glu Ser Pro Asp Gln Trp Ser Ser Ser Pro His Ser
            2420                2425                2430

Ala Ser Asp Trp Ser Asp Val Thr Thr Ser Pro Thr Pro Gly Gly Ala
            2435                2440                2445

Gly Gly Gly Gln Arg Gly Pro Gly Thr His Met Ser Glu Pro Pro His
    2450                2455                2460

Asn Asn Met Gln Val Tyr Ala
2465                2470

<210> SEQ ID NO 2
<211> LENGTH: 2556
<212> TYPE: PRT
<213> ORGANISM: Homo sapiens

<400> SEQUENCE: 2

Met Pro Pro Leu Leu Ala Pro Leu Leu Cys Leu Ala Leu Leu Pro Ala
 1               5                  10                  15

Leu Ala Ala Arg Gly Pro Arg Cys Ser Gln Pro Gly Glu Thr Cys Leu
            20                  25                  30

Asn Gly Gly Lys Cys Glu Ala Ala Asn Gly Thr Glu Ala Cys Val Cys
        35                  40                  45

Gly Gly Ala Phe Val Gly Pro Arg Cys Gln Asp Pro Asn Pro Cys Leu
    50                  55                  60

Ser Thr Pro Cys Lys Asn Ala Gly Thr Cys His Val Val Asp Arg Arg
65                  70                  75                  80

Gly Val Ala Asp Tyr Ala Cys Ser Cys Ala Leu Gly Phe Ser Gly Pro
                85                  90                  95

Leu Cys Leu Thr Pro Leu Asp Asn Ala Cys Leu Thr Asn Pro Cys Arg
            100                 105                 110

Asn Gly Gly Thr Cys Asp Leu Leu Thr Leu Thr Glu Tyr Lys Cys Arg
        115                 120                 125

Cys Pro Pro Gly Trp Ser Gly Lys Ser Cys Gln Gln Ala Asp Pro Cys
    130                 135                 140

Ala Ser Asn Pro Cys Ala Asn Gly Gly Gln Cys Leu Pro Phe Glu Ala
145                 150                 155                 160

Ser Tyr Ile Cys His Cys Pro Pro Ser Phe His Gly Pro Thr Cys Trp
                165                 170                 175

Gln Asp Val Asn Glu Cys Gly Gln Lys Pro Arg Leu Cys Arg His Gly
            180                 185                 190

Gly Thr Cys His Asn Glu Val Gly Ser Tyr Arg Cys Val Cys Arg Ala
        195                 200                 205

Thr His Thr Gly Pro Asn Cys Glu Trp Pro Tyr Val Pro Cys Ser Pro
    210                 215                 220

Ser Pro Cys Gln Asn Gly Gly Thr Cys Arg Pro Thr Gly Asp Val Thr
225                 230                 235                 240

His Glu Cys Ala Cys Leu Pro Gly Phe Thr Gly Gln Asn Cys Glu Glu
                245                 250                 255

Asn Ile Asp Asp Cys Pro Gly Asn Asn Cys Lys Asn Gly Gly Ala Cys
            260                 265                 270

Val Asp Gly Val Asn Thr Tyr Asn Cys Pro Cys Pro Pro Glu Trp Thr
        275                 280                 285

Gly Gln Tyr Cys Thr Glu Asp Val Asp Glu Cys Gln Leu Met Pro Asn
    290                 295                 300
```

-continued

```
Ala Cys Gln Asn Gly Gly Thr Cys His Asn Thr His Gly Gly Tyr Asn
305                 310                 315                 320

Cys Val Cys Val Asn Gly Trp Thr Gly Glu Asp Cys Ser Glu Asn Ile
                325                 330                 335

Asp Asp Cys Ala Ser Ala Cys Phe His Gly Ala Thr Cys His Asp
            340                 345                 350

Arg Val Ala Ser Phe Tyr Cys Glu Cys Pro His Gly Arg Thr Gly Leu
                355                 360                 365

Leu Cys His Leu Asn Asp Ala Cys Ile Ser Asn Pro Cys Asn Glu Gly
    370                 375                 380

Ser Asn Cys Asp Thr Asn Pro Val Asn Gly Lys Ala Ile Cys Thr Cys
385                 390                 395                 400

Pro Ser Gly Tyr Thr Gly Pro Ala Cys Ser Gln Asp Val Asp Glu Cys
                405                 410                 415

Ser Leu Gly Ala Asn Pro Cys Glu His Ala Gly Lys Cys Ile Asn Thr
                420                 425                 430

Leu Gly Ser Phe Glu Cys Gln Cys Leu Gln Gly Tyr Thr Gly Pro Arg
        435                 440                 445

Cys Glu Ile Asp Val Asn Glu Cys Val Ser Asn Pro Cys Gln Asn Asp
    450                 455                 460

Ala Thr Cys Leu Asp Gln Ile Gly Glu Phe Gln Cys Met Cys Met Pro
465                 470                 475                 480

Gly Tyr Glu Gly Val His Cys Glu Val Asn Thr Asp Glu Cys Ala Ser
                485                 490                 495

Ser Pro Cys Leu His Asn Gly Arg Cys Leu Asp Lys Ile Asn Glu Phe
            500                 505                 510

Gln Cys Glu Cys Pro Thr Gly Phe Thr Gly His Leu Cys Gln Tyr Asp
    515                 520                 525

Val Asp Glu Cys Ala Ser Thr Pro Cys Lys Asn Gly Ala Lys Cys Leu
    530                 535                 540

Asp Gly Pro Asn Thr Tyr Thr Cys Val Cys Thr Glu Gly Tyr Thr Gly
545                 550                 555                 560

Thr His Cys Glu Val Asp Ile Asp Glu Cys Asp Pro Asp Pro Cys His
            565                 570                 575

Tyr Gly Ser Cys Lys Asp Gly Val Ala Thr Phe Thr Cys Leu Cys Arg
                580                 585                 590

Pro Gly Tyr Thr Gly His His Cys Glu Thr Asn Ile Asn Glu Cys Ser
            595                 600                 605

Ser Gln Pro Cys Arg Leu Trp Gly Thr Cys Gln Asp Pro Asp Asn Ala
    610                 615                 620

Tyr Leu Cys Phe Cys Leu Lys Gly Thr Thr Gly Pro Asn Cys Glu Ile
625                 630                 635                 640

Asn Leu Asp Asp Cys Ala Ser Ser Pro Cys Asp Ser Gly Thr Cys Leu
                645                 650                 655

Asp Lys Ile Asp Gly Tyr Glu Cys Ala Cys Glu Pro Tyr Thr Gly
                660                 665                 670

Ser Met Cys Asn Ser Asn Ile Asp Glu Cys Ala Gly Asn Pro Cys His
                675                 680                 685

Asn Gly Gly Thr Cys Glu Asp Gly Ile Asn Gly Phe Thr Cys Arg Cys
    690                 695                 700

Pro Glu Gly Tyr His Asp Pro Thr Cys Leu Ser Glu Val Asn Glu Cys
705                 710                 715                 720
```

-continued

```
Asn Ser Asn Pro Cys Val His Gly Ala Cys Trp Asp Ser Leu Asn Gly
            725                 730                 735
Tyr Lys Cys Asp Cys Asp Pro Gly Trp Ser Gly Thr Asn Cys Asp Ile
            740                 745                 750
Asn Asn Asn Glu Cys Glu Ser Asn Pro Cys Val Asn Gly Gly Thr Cys
            755                 760                 765
Lys Asp Met Thr Ser Gly Ile Val Cys Thr Cys Trp Glu Gly Phe Ser
            770                 775                 780
Gly Pro Asn Cys Gln Thr Asn Ile Asn Glu Cys Ala Ser Asn Pro Cys
785                 790                 795                 800
Leu Asn Lys Gly Thr Cys Ile Asp Asp Val Ala Gly Tyr Lys Cys Asn
            805                 810                 815
Cys Leu Leu Pro Tyr Thr Gly Ala Thr Cys Glu Val Val Leu Ala Pro
            820                 825                 830
Cys Ala Pro Ser Pro Cys Arg Asn Gly Gly Glu Cys Arg Gln Ser Glu
            835                 840                 845
Asp Tyr Glu Ser Phe Ser Cys Val Cys Pro Thr Ala Gly Ala Lys Gly
            850                 855                 860
Gln Thr Cys Glu Val Asp Ile Asn Glu Cys Val Leu Ser Pro Cys Trp
865                 870                 875                 880
His Gly Ala Ser Cys Gln Asn Thr His Gly Xaa Tyr Arg Cys His Cys
            885                 890                 895
Gln Ala Gly Tyr Ser Gly Arg Asn Cys Glu Thr Asp Ile Asp Asp Cys
            900                 905                 910
Trp Pro Asn Pro Cys His Asn Gly Gly Ser Cys Thr Asp Gly Ile Asn
            915                 920                 925
Thr Ala Phe Cys Asp Cys Leu Pro Gly Phe Trp Gly Thr Phe Cys Glu
            930                 935                 940
Glu Asp Ile Asn Glu Cys Ala Ser Asp Pro Cys Arg Asn Gly Ala Asn
945                 950                 955                 960
Cys Thr Asp Cys Val Asp Ser Tyr Thr Cys Thr Cys Pro Ala Gly Phe
            965                 970                 975
Ser Gly Ile His Cys Glu Asn Asn Thr Pro Asp Cys Thr Glu Ser Ser
            980                 985                 990
Cys Phe Asn Gly Gly Thr Cys Val Asp Gly Ile Asn Ser Phe Thr Cys
            995                 1000                1005
Leu Cys Pro Pro Gly Phe Thr Gly Ser Tyr Cys Gln His Val Val Asn
            1010                1015                1020
Glu Cys Asp Ser Arg Pro Cys Leu Leu Gly Gly Thr Cys Gln Asp Gly
1025                1030                1035                1040
Arg Gly Leu His Arg Cys Thr Cys Pro Gln Gly Tyr Thr Gly Pro Asn
            1045                1050                1055
Cys Gln Asn Leu Val His Trp Cys Asp Ser Ser Pro Cys Lys Asn Gly
            1060                1065                1070
Gly Lys Cys Trp Gln Thr His Thr Gln Tyr Arg Cys Glu Cys Pro Ser
            1075                1080                1085
Gly Trp Thr Gly Leu Tyr Cys Asp Val Pro Ser Val Ser Cys Glu Val
            1090                1095                1100
Ala Ala Gln Arg Gln Gly Val Asp Val Ala Arg Leu Cys Gln His Gly
1105                1110                1115                1120
Gly Leu Cys Val Asp Ala Gly Asn Thr His His Cys Arg Cys Gln Ala
            1125                1130                1135
Gly Tyr Thr Gly Ser Tyr Cys Glu Asp Leu Val Asp Glu Cys Ser Pro
```

```
                  1140           1145           1150
Ser Pro Cys Gln Asn Gly Ala Thr Cys Thr Asp Tyr Leu Gly Gly Tyr
        1155            1160           1165
Ser Cys Lys Cys Val Ala Gly Tyr His Gly Val Asn Cys Ser Glu Glu
    1170            1175           1180
Ile Asp Glu Cys Leu Ser His Pro Cys Gln Asn Gly Gly Thr Cys Leu
1185           1190           1195           1200
Asp Leu Pro Asn Thr Tyr Lys Cys Ser Cys Pro Trp Gly Thr Gln Gly
            1205           1210           1215
Val His Cys Glu Ile Asn Val Asp Asp Cys Asn Pro Pro Val Asp Pro
        1220           1225           1230
Val Ser Trp Ser Pro Lys Cys Phe Asn Asn Gly Thr Cys Val Asp Gln
        1235           1240           1245
Val Gly Gly Tyr Ser Cys Thr Cys Pro Pro Gly Phe Val Gly Glu Arg
        1250           1255           1260
Cys Glu Gly Asp Val Asn Glu Cys Leu Ser Asn Pro Cys Asp Ala Arg
1265           1270           1275           1280
Gly Thr Gln Asn Cys Val Gln Arg Val Asn Asp Phe His Cys Glu Cys
            1285           1290           1295
Arg Ala Gly His Thr Gly Arg Arg Cys Glu Ser Val Ile Asn Gly Cys
        1300           1305           1310
Lys Gly Lys Pro Cys Lys Asn Gly Gly Thr Cys Ala Val Ala Ser Asn
        1315           1320           1325
Thr Ala Arg Gly Phe Ile Cys Lys Cys Pro Ala Gly Phe Glu Gly Ala
        1330           1335           1340
Thr Cys Glu Asn Asp Ala Arg Thr Cys Gly Ser Leu Arg Cys Leu Asn
1345           1350           1355           1360
Gly Gly Thr Cys Ile Ser Gly Pro Arg Ser Pro Thr Cys Leu Cys Leu
        1365           1370           1375
Gly Pro Phe Thr Gly Pro Glu Cys Gln Phe Pro Ala Ser Ser Pro Cys
        1380           1385           1390
Leu Gly Gly Asn Pro Cys Tyr Asn Gln Gly Thr Cys Glu Pro Thr Ser
        1395           1400           1405
Glu Ser Pro Phe Tyr Arg Cys Leu Cys Pro Ala Lys Phe Asn Gly Leu
    1410           1415           1420
Leu Cys His Ile Leu Asp Tyr Ser Phe Gly Gly Gly Ala Gly Arg Asp
1425           1430           1435           1440
Ile Pro Pro Pro Leu Ile Glu Glu Ala Cys Glu Leu Pro Glu Cys Gln
            1445           1450           1455
Glu Asp Ala Gly Asn Lys Val Cys Ser Leu Gln Cys Asn Asn His Ala
        1460           1465           1470
Cys Gly Trp Asp Gly Gly Asp Cys Ser Leu Asn Phe Asn Asp Pro Trp
        1475           1480           1485
Lys Asn Cys Thr Gln Ser Leu Gln Cys Trp Lys Tyr Phe Ser Asp Gly
    1490           1495           1500
His Cys Asp Ser Gln Cys Asn Ser Ala Gly Cys Leu Phe Asp Gly Phe
1505           1510           1515           1520
Asp Cys Gln Arg Ala Glu Gly Gln Cys Asn Pro Leu Tyr Asp Gln Tyr
            1525           1530           1535
Cys Lys Asp His Phe Ser Asp Gly His Cys Asp Gln Gly Cys Asn Ser
            1540           1545           1550
Ala Glu Cys Glu Trp Asp Gly Leu Asp Cys Ala Glu His Val Pro Glu
        1555           1560           1565
```

-continued

Arg Leu Ala Ala Gly Thr Leu Val Val Val Leu Met Pro Pro Glu
    1570                1575                1580

Gln Leu Arg Asn Ser Ser Phe His Phe Leu Trp Glu Leu Ser Arg Val
1585                1590                1595                1600

Leu His Thr Asn Val Val Phe Lys Arg Asp Ala His Gly Gln Gln Met
            1605                1610                1615

Ile Phe Pro Tyr Tyr Gly Arg Glu Glu Leu Arg Lys His Pro Ile
        1620                1625                1630

Lys Arg Ala Ala Glu Gly Trp Ala Ala Pro Asp Ala Leu Leu Gly Gln
    1635                1640                1645

Val Lys Ala Ser Leu Leu Pro Gly Gly Ser Glu Gly Gly Trp Trp Trp
    1650                1655                1660

Arg Glu Leu Asp Pro Met Asp Val Arg Gly Ser Ile Val Tyr Leu Glu
1665                1670                1675                1680

Ile Asp Asn Trp Gln Cys Val Gln Ala Ser Ser Gln Cys Phe Gln Ser
            1685                1690                1695

Ala Thr Asp Val Ala Ala Phe Leu Gly Ala Leu Ala Ser Leu Gly Ser
        1700                1705                1710

Leu Asn Ile Pro Tyr Lys Ile Glu Ala Val Gln Ser Glu Thr Val Glu
    1715                1720                1725

Pro Pro Pro Ala Gln Leu His Phe Met Tyr Val Ala Ala Ala Ala
    1730                1735                1740

Phe Val Leu Leu Phe Phe Val Gly Cys Gly Val Leu Leu Ser Arg Lys
1745                1750                1755                1760

Arg Trp Xaa Gln His Gly Gln Leu Trp Phe Pro Glu Gly Phe Lys Val
            1765                1770                1775

Ser Glu Ala Ser Lys Lys Lys Trp Trp Glu Xaa Leu Gly Glu Asp Ser
        1780                1785                1790

Val Gly Leu Lys Pro Leu Lys Asn Ala Ser Asp Gly Ala Leu Met Asp
    1795                1800                1805

Asp Asn Gln Asn Glu Trp Gly Asp Glu Asp Leu Glu Thr Lys Lys Phe
    1810                1815                1820

Trp Phe Glu Glu Pro Val Val Leu Pro Asp Leu Asp Asp Gln Thr Asp
1825                1830                1835                1840

His Trp Gln Trp Thr Gln Gln His Leu Asp Ala Ala Asp Leu Arg Met
            1845                1850                1855

Ser Ala Met Ala Pro Thr Pro Pro Gln Gly Glu Val Asp Ala Asp Cys
        1860                1865                1870

Met Asp Val Asn Val Arg Gly Pro Asp Gly Phe Thr Pro Leu Met Ile
    1875                1880                1885

Ala Ser Cys Ser Gly Gly Gly Leu Glu Thr Gly Asn Ser Glu Glu Glu
    1890                1895                1900

Glu Asp Ala Pro Ala Val Ile Ser Asp Phe Ile Tyr Gln Gly Ala Ser
1905                1910                1915                1920

Leu His Asn Gln Thr Asp Arg Thr Gly Glu Thr Ala Leu His Leu Ala
            1925                1930                1935

Ala Arg Tyr Ser Arg Ser Asp Ala Ala Lys Arg Leu Leu Glu Ala Ser
        1940                1945                1950

Ala Asp Ala Asn Ile Gln Asp Asn Met Gly Arg Thr Pro Leu His Ala
    1955                1960                1965

Ala Val Ser Ala Asp Ala Gln Gly Val Phe Gln Ile Leu Ile Trp Asn
    1970                1975                1980

-continued

```
Arg Ala Thr Asp Leu Asp Ala Arg Met His Asp Gly Thr Thr Pro Leu
1985                1990                1995                2000

Ile Leu Ala Ala Arg Leu Ala Val Glu Gly Met Leu Glu Asp Leu Ile
        2005                2010                2015

Asn Ser His Ala Asp Val Asn Ala Val Asp Asp Leu Gly Lys Ser Ala
            2020                2025                2030

Leu His Trp Ala Ala Val Asn Asn Val Asp Ala Ala Val Val Leu
        2035                2040                2045

Leu Lys Asn Gly Ala Asn Lys Asp Met Gln Asn Asn Arg Glu Glu Thr
        2050                2055                2060

Pro Leu Phe Leu Ala Ala Trp Glu Gly Ser Tyr Glu Thr Ala Lys Val
2065                2070                2075                2080

Leu Leu Asp His Phe Ala Asn Trp Asp Ile Thr Asp His Met Asp Arg
            2085                2090                2095

Leu Pro Arg Asp Ile Ala Gln Glu Arg Met His His Asp Ile Val Arg
            2100                2105                2110

Leu Leu Asp Glu Tyr Asn Leu Val Arg Ser Pro Gln Leu His Gly Ala
            2115                2120                2125

Pro Leu Gly Gly Thr Pro Thr Leu Ser Pro Pro Leu Cys Ser Pro Asn
    2130                2135                2140

Gly Tyr Leu Gly Ser Leu Lys Pro Gly Val Gln Gly Lys Lys Val Arg
2145                2150                2155                2160

Lys Pro Ser Ser Lys Gly Leu Ala Cys Gly Ser Lys Glu Ala Lys Asp
            2165                2170                2175

Leu Lys Ala Trp Arg Lys Lys Ser Gln Asp Gly Lys Gly Cys Leu Leu
            2180                2185                2190

Asp Ser Ser Gly Met Leu Ser Pro Val Asp Ser Leu Glu Ser Pro His
        2195                2200                2205

Gly Tyr Leu Ser Asp Val Ala Ser Pro Pro Leu Leu Pro Ser Pro Phe
    2210                2215                2220

Gln Gln Ser Pro Ser Val Pro Leu Asn His Leu Pro Gly Met Pro Asp
2225                2230                2235                2240

Thr His Leu Gly Ile Gly His Leu Asn Val Ala Ala Lys Pro Glu Met
            2245                2250                2255

Ala Ala Leu Gly Gly Gly Gly Trp Leu Ala Phe Glu Thr Gly Pro Pro
            2260                2265                2270

Arg Leu Ser His Leu Pro Val Ala Ser Gly Thr Ser Thr Val Leu Gly
            2275                2280                2285

Ser Ser Ser Gly Gly Ala Leu Asn Phe Thr Val Gly Gly Ser Thr Ser
        2290                2295                2300

Leu Asn Gly Gln Cys Glu Trp Leu Ser Trp Leu Gln Ser Gly Met Val
2305                2310                2315                2320

Pro Asn Gln Tyr Asn Pro Leu Trp Gly Ser Val Ala Pro Gly Pro Leu
            2325                2330                2335

Ser Thr Gln Ala Pro Ser Leu Gln His Gly Met Val Gly Pro Leu His
            2340                2345                2350

Ser Ser Leu Ala Ala Ser Ala Leu Ser Gln Met Met Ser Tyr Gln Gly
        2355                2360                2365

Leu Pro Ser Thr Trp Leu Ala Thr Gln Pro His Leu Val Gln Thr Gln
    2370                2375                2380

Gln Val Gln Pro Gln Asn Leu Gln Met Gln Gln Asn Leu Gln Pro
2385                2390                2395                2400

Ala Asn Ile Gln Gln Gln Gln Ser Leu Gln Pro Pro Pro Pro Pro Pro
```

-continued

```
                      2405                2410                  2415
Gln Pro His Leu Gly Val Ser Ala Ala Ser Gly His Leu Gly Trp
            2420                2425                2430

Ser Phe Leu Ser Gly Glu Pro Ser Gln Ala Asp Val Gln Pro Leu Gly
        2435                2440                2445

Pro Ser Ser Leu Ala Val His Thr Ile Leu Pro Gln Glu Ser Pro Ala
    2450                2455                2460

Leu Pro Thr Ser Leu Pro Ser Ser Leu Val Pro Pro Val Thr Ala Ala
2465                2470                2475                2480

Gln Phe Leu Thr Pro Pro Ser Gln His Ser Tyr Ser Ser Pro Val Glu
            2485                2490                2495

Asn Thr Pro Ser His Gln Leu Gln Val Pro Glu His Pro Phe Leu Thr
        2500                2505                2510

Pro Ser Pro Glu Ser Pro Asp Gln Trp Ser Ser Ser Ser Pro His Ser
    2515                2520                2525

Asn Val Ser Asp Trp Ser Glu Gly Val Ser Ser Pro Pro Thr Ser Met
2530                2535                2540

Gln Ser Gln Ile Ala Arg Ile Pro Glu Ala Phe Lys
2545                2550                2555

<210> SEQ ID NO 3
<211> LENGTH: 2523
<212> TYPE: PRT
<213> ORGANISM: Xenopus sp.

<400> SEQUENCE: 3

Met Asp Arg Ile Gly Leu Ala Val Leu Leu Cys Ser Leu Pro Val Leu
1               5                   10                  15

Thr Gln Gly Leu Arg Cys Thr Gln Thr Ala Glu Met Cys Leu Asn Gly
            20                  25                  30

Gly Arg Cys Glu Met Thr Pro Gly Thr Gly Val Cys Leu Cys Gly
        35                  40                  45

Asn Leu Tyr Phe Gly Glu Arg Cys Gln Phe Pro Asn Pro Cys Thr Ile
    50                  55                  60

Lys Asn Gln Cys Met Asn Phe Gly Thr Cys Glu Pro Val Leu Gln Gly
65                  70                  75                  80

Asn Ala Ile Asp Phe Ile Cys His Cys Pro Val Gly Phe Thr Asp Lys
                85                  90                  95

Val Cys Leu Thr Pro Val Asp Asn Ala Cys Val Asn Asn Pro Cys Arg
            100                 105                 110

Asn Gly Gly Thr Cys Glu Leu Leu Asn Ser Val Thr Glu Tyr Lys Cys
        115                 120                 125

Arg Cys Pro Pro Gly Trp Thr Gly Asp Ser Cys Gln Gln Ala Asp Pro
    130                 135                 140

Cys Ala Ser Asn Pro Cys Ala Asn Gly Gly Lys Cys Leu Pro Phe Glu
145                 150                 155                 160

Ile Gln Tyr Ile Cys Lys Cys Pro Pro Gly Phe His Gly Ala Thr Cys
                165                 170                 175

Lys Gln Asp Ile Asn Glu Cys Ser Gln Asn Pro Cys Lys Asn Gly Gly
            180                 185                 190

Gln Cys Ile Asn Glu Phe Gly Ser Tyr Arg Cys Thr Cys Gln Asn Arg
        195                 200                 205

Phe Thr Gly Arg Asn Cys Asp Glu Pro Tyr Val Pro Cys Asn Pro Ser
    210                 215                 220
```

-continued

```
Pro Cys Leu Asn Gly Gly Thr Cys Arg Gln Thr Asp Thr Ser Tyr
225                 230                 235                 240

Asp Cys Thr Cys Leu Pro Gly Phe Ser Gly Gln Asn Cys Glu Glu Asn
                245                 250                 255

Ile Asp Asp Cys Pro Ser Asn Asn Cys Arg Asn Gly Gly Thr Cys Val
            260                 265                 270

Asp Gly Val Asn Thr Tyr Asn Cys Gln Cys Pro Pro Asp Trp Thr Gly
        275                 280                 285

Gln Tyr Cys Thr Glu Asp Val Asp Glu Cys Gln Leu Met Pro Asn Ala
    290                 295                 300

Cys Gln Asn Gly Gly Thr Cys His Asn Thr Tyr Gly Gly Tyr Asn Cys
305                 310                 315                 320

Val Cys Val Asn Gly Trp Thr Gly Glu Asp Cys Ser Glu Asn Ile Asp
                325                 330                 335

Asp Cys Ala Asn Ala Ala Cys His Ser Gly Ala Thr Cys His Asp Arg
            340                 345                 350

Val Ala Ser Phe Tyr Cys Glu Cys Pro His Gly Arg Thr Gly Leu Leu
        355                 360                 365

Cys His Leu Asp Asn Ala Cys Ile Ser Asn Pro Cys Asn Glu Gly Ser
370                 375                 380

Asn Cys Asp Thr Asn Pro Val Asn Gly Lys Ala Ile Cys Thr Cys Pro
385                 390                 395                 400

Pro Gly Tyr Thr Gly Pro Ala Cys Asn Asn Asp Val Asp Glu Cys Ser
            405                 410                 415

Leu Gly Ala Asn Pro Cys Glu His Gly Gly Arg Cys Thr Asn Thr Leu
        420                 425                 430

Gly Ser Phe Gln Cys Asn Cys Pro Gln Gly Tyr Ala Gly Pro Arg Cys
    435                 440                 445

Glu Ile Asp Val Asn Glu Cys Leu Ser Asn Pro Cys Gln Asn Asp Ser
450                 455                 460

Thr Cys Leu Asp Gln Ile Gly Glu Phe Gln Cys Ile Cys Met Pro Gly
465                 470                 475                 480

Tyr Glu Gly Leu Tyr Cys Glu Thr Asn Ile Asp Glu Cys Ala Ser Asn
            485                 490                 495

Pro Cys Leu His Asn Gly Lys Cys Ile Asp Lys Ile Asn Glu Phe Arg
        500                 505                 510

Cys Asp Cys Pro Thr Gly Phe Ser Gly Asn Leu Cys Gln His Asp Phe
    515                 520                 525

Asp Glu Cys Thr Ser Thr Pro Cys Lys Asn Gly Ala Lys Cys Leu Asp
530                 535                 540

Gly Pro Asn Ser Tyr Thr Cys Gln Cys Thr Glu Gly Phe Thr Gly Arg
545                 550                 555                 560

His Cys Glu Gln Asp Ile Asn Glu Cys Ile Pro Asp Pro Cys His Tyr
            565                 570                 575

Gly Thr Cys Lys Asp Gly Ile Ala Thr Phe Thr Cys Leu Cys Arg Pro
        580                 585                 590

Gly Tyr Thr Gly Arg Leu Cys Asp Asn Asp Ile Asn Glu Cys Leu Ser
    595                 600                 605

Lys Pro Cys Leu Asn Gly Gly Gln Cys Thr Asp Arg Glu Asn Gly Tyr
610                 615                 620

Ile Cys Thr Cys Pro Lys Gly Thr Thr Gly Val Asn Cys Glu Thr Lys
625                 630                 635                 640

Ile Asp Asp Cys Ala Ser Asn Leu Cys Asp Asn Gly Lys Cys Ile Asp
```

-continued

```
                645                 650                 655
Lys Ile Asp Gly Tyr Glu Cys Thr Cys Glu Pro Gly Tyr Thr Gly Lys
                660                 665                 670
Leu Cys Asn Ile Asn Ile Asn Glu Cys Asp Ser Asn Pro Cys Arg Asn
                675                 680                 685
Gly Gly Thr Cys Lys Asp Gln Ile Asn Gly Phe Thr Cys Val Cys Pro
            690                 695                 700
Asp Gly Tyr His Asp His Met Cys Leu Ser Glu Val Asn Glu Cys Asn
705                 710                 715                 720
Ser Asn Pro Cys Ile His Gly Ala Cys His Asp Gly Val Asn Gly Tyr
                725                 730                 735
Lys Cys Asp Cys Glu Ala Gly Trp Ser Gly Ser Asn Cys Asp Ile Asn
            740                 745                 750
Asn Asn Glu Cys Glu Ser Asn Pro Cys Met Asn Gly Gly Thr Cys Lys
                755                 760                 765
Asp Met Thr Gly Ala Tyr Ile Cys Thr Cys Lys Ala Gly Phe Ser Gly
            770                 775                 780
Pro Asn Cys Gln Thr Asn Ile Asn Glu Cys Ser Ser Asn Pro Cys Leu
785                 790                 795                 800
Asn His Gly Thr Cys Ile Asp Asp Val Ala Gly Tyr Lys Cys Asn Cys
                805                 810                 815
Met Leu Pro Tyr Thr Gly Ala Ile Cys Glu Ala Val Leu Ala Pro Cys
            820                 825                 830
Ala Gly Ser Pro Cys Lys Asn Gly Gly Arg Cys Lys Glu Ser Glu Asp
                835                 840                 845
Phe Glu Thr Phe Ser Cys Glu Cys Pro Pro Gly Trp Gln Gly Gln Thr
            850                 855                 860
Cys Glu Ile Asp Met Asn Glu Cys Val Asn Arg Pro Cys Arg Asn Gly
865                 870                 875                 880
Ala Thr Cys Gln Asn Thr Asn Gly Ser Tyr Lys Cys Asn Cys Lys Pro
                885                 890                 895
Gly Tyr Thr Gly Arg Asn Cys Glu Met Asp Ile Asp Cys Gln Pro
            900                 905                 910
Asn Pro Cys His Asn Gly Gly Ser Cys Ser Asp Gly Ile Asn Met Phe
            915                 920                 925
Phe Cys Asn Cys Pro Ala Gly Phe Arg Gly Pro Lys Cys Glu Glu Asp
930                 935                 940
Ile Asn Glu Cys Ala Ser Asn Pro Cys Lys Asn Gly Ala Asn Cys Thr
945                 950                 955                 960
Asp Cys Val Asn Ser Tyr Thr Cys Thr Cys Gln Pro Gly Phe Ser Gly
                965                 970                 975
Ile His Cys Glu Ser Asn Thr Pro Asp Cys Thr Glu Ser Ser Cys Phe
                980                 985                 990
Asn Gly Gly Thr Cys Ile Asp Gly Ile Asn Thr Phe Thr Cys Gln Cys
            995                 1000                1005
Pro Pro Gly Phe Thr Gly Ser Tyr Cys Gln His Asp Ile Asn Glu Cys
    1010                1015                1020
Asp Ser Lys Pro Cys Leu Asn Gly Gly Thr Cys Gln Asp Ser Tyr Gly
1025                1030                1035                1040
Thr Tyr Lys Cys Thr Cys Pro Gln Gly Tyr Thr Gly Leu Asn Cys Gln
                1045                1050                1055
Asn Leu Val Arg Trp Cys Asp Ser Ser Pro Cys Lys Asn Gly Gly Lys
            1060                1065                1070
```

-continued

```
Cys Trp Gln Thr Asn Asn Phe Tyr Arg Cys Glu Cys Lys Ser Gly Trp
    1075                1080                1085
Thr Gly Val Tyr Cys Asp Val Pro Ser Val Ser Cys Glu Val Ala Ala
    1090                1095                1100
Lys Gln Gln Gly Val Asp Ile Val His Leu Cys Arg Asn Ser Gly Met
1105                1110                1115                1120
Cys Val Asp Thr Gly Asn Thr His Phe Cys Arg Cys Gln Ala Gly Tyr
                1125                1130                1135
Thr Gly Ser Tyr Cys Glu Glu Gln Val Asp Glu Cys Ser Pro Asn Pro
            1140                1145                1150
Cys Gln Asn Gly Ala Thr Cys Thr Asp Tyr Leu Gly Gly Tyr Ser Cys
        1155                1160                1165
Glu Cys Val Ala Gly Tyr His Gly Val Asn Cys Ser Glu Glu Ile Asn
    1170                1175                1180
Glu Cys Leu Ser His Pro Cys Gln Asn Gly Gly Thr Cys Ile Asp Leu
1185                1190                1195                1200
Ile Asn Thr Tyr Lys Cys Ser Cys Pro Arg Gly Thr Gln Gly Val His
                1205                1210                1215
Cys Glu Ile Asn Val Asp Asp Cys Thr Pro Phe Tyr Asp Ser Phe Thr
            1220                1225                1230
Leu Glu Pro Lys Cys Phe Asn Asn Gly Lys Cys Ile Asp Arg Val Gly
        1235                1240                1245
Gly Tyr Asn Cys Ile Cys Pro Pro Gly Phe Val Gly Glu Arg Cys Glu
    1250                1255                1260
Gly Asp Val Asn Glu Cys Leu Ser Asn Pro Cys Asp Ser Arg Gly Thr
1265                1270                1275                1280
Gln Asn Cys Ile Gln Leu Val Asn Asp Tyr Arg Cys Glu Cys Arg Gln
                1285                1290                1295
Gly Phe Thr Gly Arg Arg Cys Glu Ser Val Val Asp Gly Cys Lys Gly
            1300                1305                1310
Met Pro Cys Arg Asn Gly Gly Thr Cys Ala Val Ala Ser Asn Thr Glu
        1315                1320                1325
Arg Gly Phe Ile Cys Lys Cys Pro Pro Gly Phe Asp Gly Ala Thr Cys
    1330                1335                1340
Glu Tyr Asp Ser Arg Thr Cys Ser Asn Leu Arg Cys Gln Asn Gly Gly
1345                1350                1355                1360
Thr Cys Ile Ser Val Leu Thr Ser Ser Lys Cys Val Cys Ser Glu Gly
                1365                1370                1375
Tyr Thr Gly Ala Thr Cys Gln Tyr Pro Val Ile Ser Pro Cys Ala Ser
            1380                1385                1390
His Pro Cys Tyr Asn Gly Gly Thr Cys Gln Phe Phe Ala Glu Glu Pro
        1395                1400                1405
Phe Phe Gln Cys Phe Cys Pro Lys Asn Phe Asn Gly Leu Phe Cys His
    1410                1415                1420
Ile Leu Asp Tyr Glu Phe Pro Gly Gly Leu Gly Lys Asn Ile Thr Pro
1425                1430                1435                1440
Pro Asp Asn Asp Asp Ile Cys Glu Asn Glu Gln Cys Ser Glu Leu Ala
                1445                1450                1455
Asp Asn Lys Val Cys Asn Ala Asn Cys Asn Asn His Ala Cys Gly Trp
            1460                1465                1470
Asp Gly Gly Asp Cys Ser Leu Asn Phe Asn Asp Pro Trp Lys Asn Cys
        1475                1480                1485
```

-continued

Thr Gln Ser Leu Gln Cys Trp Lys Tyr Phe Asn Asp Gly Lys Cys Asp
    1490                1495                1500

Ser Gln Cys Asn Asn Thr Gly Cys Leu Tyr Asp Gly Phe Asp Cys Gln
1505                1510                1515                1520

Lys Val Glu Val Gln Cys Asn Pro Leu Tyr Asp Gln Tyr Cys Lys Asp
            1525                1530                1535

His Phe Gln Asp Gly His Cys Asp Gln Gly Cys Asn Asn Ala Glu Cys
        1540                1545                1550

Glu Trp Asp Gly Leu Asp Cys Ala Asn Met Pro Glu Asn Leu Ala Glu
        1555                1560                1565

Gly Thr Leu Val Leu Val Val Leu Met Pro Pro Glu Arg Leu Lys Asn
        1570                1575                1580

Asn Ser Val Asn Phe Leu Arg Glu Leu Ser Arg Val Leu His Thr Asn
1585                1590                1595                1600

Val Val Phe Lys Lys Asp Ser Lys Gly Glu Tyr Lys Ile Tyr Pro Tyr
            1605                1610                1615

Tyr Gly Asn Glu Glu Glu Leu Lys Lys His His Ile Lys Arg Ser Thr
        1620                1625                1630

Asp Tyr Trp Ser Asp Ala Pro Ser Ala Ile Phe Ser Thr Met Lys Glu
        1635                1640                1645

Ser Ile Leu Leu Gly Arg His Arg Arg Glu Leu Asp Glu Met Glu Val
    1650                1655                1660

Arg Gly Ser Ile Val Tyr Leu Glu Ile Asp Asn Arg Gln Cys Tyr Lys
1665                1670                1675                1680

Ser Ser Ser Gln Cys Phe Asn Ser Ala Thr Asp Val Ala Ala Phe Leu
            1685                1690                1695

Gly Ala Leu Ala Ser Leu Gly Ser Leu Asp Thr Leu Ser Tyr Lys Ile
        1700                1705                1710

Glu Ala Val Lys Ser Glu Asn Met Glu Thr Pro Lys Pro Ser Thr Leu
        1715                1720                1725

Tyr Pro Met Leu Ser Met Leu Val Ile Pro Leu Leu Ile Ile Phe Val
    1730                1735                1740

Phe Met Met Val Ile Val Asn Lys Lys Arg Arg Arg Glu His Asp Ser
1745                1750                1755                1760

Phe Gly Ser Pro Thr Ala Leu Phe Gln Lys Asn Pro Ala Lys Arg Asn
            1765                1770                1775

Gly Glu Thr Pro Trp Glu Asp Ser Val Gly Leu Lys Pro Ile Lys Asn
        1780                1785                1790

Met Thr Asp Gly Ser Phe Met Asp Asp Asn Gln Asn Glu Trp Gly Asp
        1795                1800                1805

Glu Glu Thr Leu Glu Asn Lys Arg Phe Arg Phe Glu Glu Gln Val Ile
    1810                1815                1820

Leu Pro Glu Leu Val Asp Asp Lys Thr Asp Pro Arg Gln Trp Thr Arg
1825                1830                1835                1840

Gln His Leu Asp Ala Ala Asp Leu Arg Ile Ser Ser Met Ala Pro Thr
            1845                1850                1855

Pro Pro Gln Gly Glu Ile Glu Ala Asp Cys Met Asp Val Asn Val Arg
        1860                1865                1870

Gly Pro Asp Gly Phe Thr Pro Leu Met Ile Ala Ser Cys Ser Gly Gly
        1875                1880                1885

Gly Leu Glu Thr Gly Asn Ser Glu Glu Glu Asp Ala Ser Ala Asn
    1890                1895                1900

Met Ile Ser Asp Phe Ile Gly Gln Gly Ala Gln Leu His Asn Gln Thr

```
                1905                1910                1915                1920
Asp Arg Thr Gly Glu Thr Ala Leu His Leu Ala Ala Arg Tyr Ala Arg
                    1925                1930                1935
Ala Asp Ala Ala Lys Arg Leu Leu Glu Ser Ser Ala Asp Ala Asn Val
            1940                1945                1950
Gln Asp Asn Met Gly Arg Thr Pro Leu His Ala Ala Val Ala Ala Asp
        1955                1960                1965
Ala Gln Gly Val Phe Gln Ile Leu Ile Arg Asn Arg Ala Thr Asp Leu
    1970                1975                1980
Asp Ala Arg Met Phe Asp Gly Thr Thr Pro Leu Ile Leu Ala Ala Arg
1985                1990                1995                2000
Leu Ala Val Glu Gly Met Val Glu Glu Leu Ile Asn Ala His Ala Asp
                2005                2010                2015
Val Asn Ala Val Asp Glu Phe Gly Lys Ser Ala Leu His Trp Ala Ala
            2020                2025                2030
Ala Val Asn Asn Val Asp Ala Ala Val Leu Leu Lys Asn Ser Ala
        2035                2040                2045
Asn Lys Asp Met Gln Asn Asn Lys Glu Glu Thr Ser Leu Phe Leu Ala
    2050                2055                2060
Ala Arg Glu Gly Ser Tyr Glu Thr Ala Lys Val Leu Leu Asp His Tyr
2065                2070                2075                2080
Ala Asn Arg Asp Ile Thr Asp His Met Asp Arg Leu Pro Arg Asp Ile
                2085                2090                2095
Ala Gln Glu Arg Met His His Asp Ile Val His Leu Leu Asp Glu Tyr
            2100                2105                2110
Asn Leu Val Lys Ser Pro Thr Leu His Asn Gly Pro Leu Gly Ala Thr
        2115                2120                2125
Thr Leu Ser Pro Pro Ile Cys Ser Pro Asn Gly Tyr Met Gly Asn Met
    2130                2135                2140
Lys Pro Ser Val Gln Ser Lys Lys Ala Arg Lys Pro Ser Ile Lys Gly
2145                2150                2155                2160
Asn Gly Cys Lys Glu Ala Lys Glu Leu Lys Ala Arg Arg Lys Lys Ser
                2165                2170                2175
Gln Asp Gly Lys Thr Thr Leu Leu Asp Ser Gly Ser Ser Gly Val Leu
            2180                2185                2190
Ser Pro Val Asp Ser Leu Glu Ser Thr His Gly Tyr Leu Ser Asp Val
        2195                2200                2205
Ser Ser Pro Pro Leu Met Thr Ser Pro Phe Gln Gln Ser Pro Ser Met
    2210                2215                2220
Pro Leu Asn His Leu Thr Ser Met Pro Glu Ser Gln Leu Gly Met Asn
2225                2230                2235                2240
His Ile Asn Met Ala Thr Lys Gln Glu Met Ala Ala Gly Ser Asn Arg
                2245                2250                2255
Met Ala Phe Asp Ala Met Val Pro Arg Leu Thr His Leu Asn Ala Ser
            2260                2265                2270
Ser Pro Asn Thr Ile Met Ser Asn Gly Ser Met His Phe Thr Val Gly
        2275                2280                2285
Gly Ala Pro Thr Met Asn Ser Gln Cys Asp Trp Leu Ala Arg Leu Gln
    2290                2295                2300
Asn Gly Met Val Gln Asn Gln Tyr Asp Pro Ile Arg Asn Gly Ile Gln
2305                2310                2315                2320
Gln Gly Asn Ala Gln Gln Ala Gln Ala Leu Gln His Gly Leu Met Thr
                2325                2330                2335
```

-continued

```
Ser Leu His Asn Gly Leu Pro Ala Thr Thr Leu Ser Gln Met Met Thr
            2340                2345                2350

Tyr Gln Ala Met Pro Asn Thr Arg Leu Ala Asn Gln Pro His Leu Met
        2355                2360                2365

Gln Ala Gln Gln Met Gln Gln Gln Asn Leu Gln Leu His Gln Ser
    2370                2375                2380

Met Gln Gln Gln His His Asn Ser Ser Thr Thr Ser Thr His Ile Asn
2385                2390                2395                2400

Ser Pro Phe Cys Ser Ser Asp Ile Ser Gln Thr Asp Leu Gln Gln Met
            2405                2410                2415

Ser Ser Asn Asn Ile His Ser Val Met Pro Gln Asp Thr Gln Ile Phe
        2420                2425                2430

Ala Ala Ser Leu Pro Ser Asn Leu Thr Gln Ser Met Thr Thr Ala Gln
    2435                2440                2445

Phe Leu Thr Pro Pro Ser Gln His Ser Tyr Ser Ser Pro Met Asp Asn
        2450                2455                2460

Thr Pro Ser His Gln Leu Gln Val Pro Asp His Pro Phe Leu Thr Pro
2465                2470                2475                2480

Ser Pro Glu Ser Pro Asp Gln Trp Ser Ser Ser Pro His Ser Asn
            2485                2490                2495

Met Ser Asp Trp Ser Glu Gly Ile Ser Ser Pro Pro Thr Ser Met Gln
        2500                2505                2510

Pro Gln Arg Thr His Ile Pro Glu Ala Phe Lys
    2515                2520

<210> SEQ ID NO 4
<211> LENGTH: 2703
<212> TYPE: PRT
<213> ORGANISM: Drosophila sp.

<400> SEQUENCE: 4

Met Gln Ser Gln Arg Ser Arg Arg Ser Arg Ala Pro Asn Thr Trp
 1               5                   10                  15

Ile Cys Phe Trp Ile Asn Lys Met His Ala Val Ala Ser Leu Pro Ala
                20                  25                  30

Ser Leu Pro Leu Leu Leu Leu Thr Leu Ala Phe Ala Asn Leu Pro Asn
            35                  40                  45

Ile Val Arg Gly Thr Asp Thr Ala Leu Ala Ala Ser Cys Thr Ser
        50                  55                  60

Val Gly Cys Gln Asn Gly Gly Thr Cys Val Thr Gln Leu Asn Gly Lys
 65                  70                  75                  80

Thr Tyr Cys Ala Cys Asp Ser His Tyr Val Gly Asp Tyr Cys Glu His
                85                  90                  95

Arg Asn Pro Cys Asn Ser Met Arg Cys Gln Asn Gly Gly Thr Cys Gln
            100                 105                 110

Val Thr Phe Arg Asn Gly Arg Pro Gly Ile Ser Cys Lys Cys Pro Leu
        115                 120                 125

Gly Phe Asp Glu Ser Leu Cys Glu Ile Ala Val Pro Asn Ala Cys Asp
    130                 135                 140

His Val Thr Cys Leu Asn Gly Gly Thr Cys Gln Leu Lys Thr Leu Glu
145                 150                 155                 160

Glu Tyr Thr Cys Ala Cys Ala Asn Gly Tyr Thr Gly Glu Arg Cys Glu
                165                 170                 175

Thr Lys Asn Leu Cys Ala Ser Ser Pro Cys Arg Asn Gly Ala Thr Cys
```

-continued

```
                180                 185                 190
Thr Ala Leu Ala Gly Ser Ser Phe Thr Cys Ser Cys Pro Pro Gly
            195                 200                 205

Phe Thr Gly Asp Thr Cys Ser Tyr Asp Ile Glu Glu Cys Gln Ser Asn
210                 215                 220

Pro Cys Lys Tyr Gly Gly Ile Cys Val Asn Thr His Gly Ser Tyr Gln
225                 230                 235                 240

Cys Met Cys Pro Thr Gly Tyr Thr Gly Lys Asp Cys Asp Thr Lys Tyr
                245                 250                 255

Lys Pro Cys Ser Pro Ser Pro Cys Gln Asn Ala Gly Ile Cys Arg Ser
                260                 265                 270

Asn Gly Leu Ser Tyr Glu Cys Lys Cys Pro Lys Gly Phe Glu Gly Lys
            275                 280                 285

Asn Cys Glu Gln Asn Tyr Asp Asp Cys Leu Gly His Leu Cys Gln Asn
        290                 295                 300

Gly Gly Thr Cys Ile Asp Gly Ile Ser Asp Tyr Thr Cys Arg Cys Pro
305                 310                 315                 320

Pro Asn Phe Thr Gly Arg Phe Cys Gln Asp Val Asp Glu Cys Ala
                325                 330                 335

Gln Arg Asp His Pro Val Cys Gln Asn Gly Ala Thr Cys Thr Asn Thr
                340                 345                 350

His Gly Ser Tyr Ser Cys Ile Cys Val Asn Gly Trp Ala Gly Leu Asp
            355                 360                 365

Cys Ser Asn Asn Thr Asp Asp Cys Lys Gln Ala Ala Cys Phe Tyr Gly
        370                 375                 380

Ala Thr Cys Ile Asp Gly Val Gly Ser Phe Tyr Cys Gln Cys Thr Lys
385                 390                 395                 400

Gly Lys Thr Gly Leu Leu Cys His Leu Asp Asp Ala Cys Thr Ser Asn
                405                 410                 415

Pro Cys His Ala Asp Ala Ile Cys Asp Thr Ser Pro Ile Asn Gly Ser
                420                 425                 430

Tyr Ala Cys Ser Cys Ala Thr Gly Tyr Lys Gly Val Asp Cys Ser Glu
            435                 440                 445

Asp Ile Asp Glu Cys Asp Gln Gly Ser Pro Cys Glu His Asn Gly Ile
450                 455                 460

Cys Val Asn Thr Pro Gly Ser Tyr Arg Cys Asn Cys Ser Gln Gly Phe
465                 470                 475                 480

Thr Gly Pro Arg Cys Glu Thr Asn Ile Asn Glu Cys Glu Ser His Pro
                485                 490                 495

Cys Gln Asn Glu Gly Ser Cys Leu Asp Asp Pro Gly Thr Phe Arg Cys
                500                 505                 510

Val Cys Met Pro Gly Phe Thr Gly Thr Gln Cys Glu Ile Asp Ile Asp
            515                 520                 525

Glu Cys Gln Ser Asn Pro Cys Leu Asn Asp Gly Thr Cys His Asp Lys
        530                 535                 540

Ile Asn Gly Phe Lys Cys Ser Cys Ala Leu Gly Phe Thr Gly Ala Arg
545                 550                 555                 560

Cys Gln Ile Asn Ile Asp Asp Cys Gln Ser Gln Pro Cys Arg Asn Arg
                565                 570                 575

Gly Ile Cys His Asp Ser Ile Ala Gly Tyr Ser Cys Glu Cys Pro Pro
                580                 585                 590

Gly Tyr Thr Gly Thr Ser Cys Glu Ile Asn Ile Asn Asp Cys Asp Ser
            595                 600                 605
```

```
Asn Pro Cys His Arg Gly Lys Cys Ile Asp Val Asn Ser Phe Lys
        610                 615                 620
Cys Leu Cys Asp Pro Gly Tyr Thr Gly Tyr Ile Cys Gln Lys Gln Ile
625                 630                 635                 640
Asn Glu Cys Glu Ser Asn Pro Cys Gln Phe Asp Gly His Cys Gln Asp
                645                 650                 655
Arg Val Gly Ser Tyr Tyr Cys Gln Cys Gln Ala Gly Thr Ser Gly Lys
                660                 665                 670
Asn Cys Glu Val Asn Val Asn Glu Cys His Ser Asn Pro Cys Asn Asn
            675                 680                 685
Gly Ala Thr Cys Ile Asp Gly Ile Asn Ser Tyr Lys Cys Gln Cys Val
        690                 695                 700
Pro Gly Phe Thr Gly Gln His Cys Glu Lys Asn Val Asp Glu Cys Ile
705                 710                 715                 720
Ser Ser Pro Cys Ala Asn Asn Gly Val Cys Ile Asp Gln Val Asn Gly
                725                 730                 735
Tyr Lys Cys Glu Cys Pro Arg Gly Phe Tyr Asp Ala His Cys Leu Ser
                740                 745                 750
Asp Val Asp Glu Cys Ala Ser Asn Pro Cys Val Asn Glu Gly Arg Cys
            755                 760                 765
Glu Asp Gly Ile Asn Glu Phe Ile Cys His Cys Pro Pro Gly Tyr Thr
        770                 775                 780
Gly Lys Arg Cys Glu Leu Asp Ile Asp Glu Cys Ser Ser Asn Pro Cys
785                 790                 795                 800
Gln His Gly Gly Thr Cys Tyr Asp Lys Leu Asn Ala Phe Ser Cys Gln
                805                 810                 815
Cys Met Pro Gly Tyr Thr Gly Gln Lys Cys Glu Thr Asn Ile Asp Asp
                820                 825                 830
Cys Val Thr Asn Pro Cys Gly Asn Gly Thr Cys Ile Asp Lys Val
            835                 840                 845
Asn Gly Tyr Lys Cys Val Cys Lys Val Pro Phe Thr Gly Arg Asp Cys
        850                 855                 860
Glu Ser Lys Met Asp Pro Cys Ala Arg Asn Arg Cys Lys Asn Glu Ala
865                 870                 875                 880
Lys Cys Thr Pro Ser Ser Asn Phe Leu Asp Phe Ser Cys Thr Cys Lys
                885                 890                 895
Leu Gly Tyr Thr Gly Arg Tyr Cys Asp Glu Asp Ile Asp Glu Cys Ser
                900                 905                 910
Leu Ser Ser Pro Cys Arg Asn Gly Ala Ser Cys Leu Asn Val Pro Gly
            915                 920                 925
Ser Tyr Arg Cys Leu Cys Thr Lys Gly Tyr Glu Gly Arg Asp Cys Ala
        930                 935                 940
Ile Asn Thr Asp Asp Cys Ala Ser Phe Pro Cys Gln Asn Gly Arg Thr
945                 950                 955                 960
Cys Leu Asp Gly Ile Gly Asp Tyr Ser Cys Leu Cys Val Asp Gly Phe
                965                 970                 975
Asp Gly Lys His Cys Glu Thr Asp Ile Asn Glu Cys Leu Ser Gln Pro
            980                 985                 990
Cys Gln Asn Gly Ala Thr Cys Ser Gln Tyr Val Asn Ser Tyr Thr Cys
            995                 1000                1005
Thr Cys Pro Leu Gly Phe Ser Gly Ile Asn Cys Gln Thr Asn Asp Glu
    1010                1015                1020
```

-continued

Asp Cys Thr Glu Ser Ser Cys Leu Asn Gly Gly Ser Cys Ile Asp Gly
1025                1030                1035                1040

Ile Asn Gly Tyr Asn Cys Ser Cys Leu Ala Gly Tyr Ser Gly Ala Asn
            1045                1050                1055

Cys Gln Tyr Lys Leu Asn Lys Cys Asp Ser Asn Pro Cys Leu Asn Gly
        1060                1065                1070

Ala Thr Cys His Glu Gln Asn Asn Glu Tyr Thr Cys His Cys Pro Ser
    1075                1080                1085

Gly Phe Thr Gly Lys Gln Cys Ser Glu Tyr Val Asp Trp Cys Gly Gln
1090                1095                1100

Ser Pro Cys Glu Asn Gly Ala Thr Cys Ser Gln Met Lys His Gln Phe
1105                1110                1115                1120

Ser Cys Lys Cys Ser Ala Gly Trp Thr Gly Lys Leu Cys Asp Val Gln
            1125                1130                1135

Thr Ile Ser Cys Gln Asp Ala Ala Asp Arg Lys Gly Leu Ser Leu Arg
        1140                1145                1150

Gln Leu Cys Asn Asn Gly Thr Cys Lys Asp Tyr Gly Asn Ser His Val
    1155                1160                1165

Cys Tyr Cys Ser Gln Gly Tyr Ala Gly Ser Tyr Cys Gln Lys Glu Ile
1170                1175                1180

Asp Glu Cys Gln Ser Gln Pro Cys Gln Asn Gly Gly Thr Cys Arg Asp
1185                1190                1195                1200

Leu Ile Gly Ala Tyr Glu Cys Gln Cys Arg Gln Gly Phe Gln Gly Gln
            1205                1210                1215

Asn Cys Glu Leu Asn Ile Asp Asp Cys Ala Pro Asn Pro Cys Gln Asn
        1220                1225                1230

Gly Gly Thr Cys His Asp Arg Val Met Asn Phe Ser Cys Ser Cys Pro
    1235                1240                1245

Pro Gly Thr Met Gly Ile Ile Cys Glu Ile Asn Lys Asp Asp Cys Lys
1250                1255                1260

Pro Gly Ala Cys His Asn Asn Gly Ser Cys Ile Asp Arg Val Gly Gly
1265                1270                1275                1280

Phe Glu Cys Val Cys Gln Pro Gly Phe Val Gly Ala Arg Cys Glu Gly
            1285                1290                1295

Asp Ile Asn Glu Cys Leu Ser Asn Pro Cys Ser Asn Ala Gly Thr Leu
        1300                1305                1310

Asp Cys Val Gln Leu Val Asn Asn Tyr His Cys Asn Cys Arg Pro Gly
    1315                1320                1325

His Met Gly Arg His Cys Glu His Lys Val Asp Phe Cys Ala Gln Ser
1330                1335                1340

Pro Cys Gln Asn Gly Gly Asn Cys Asn Ile Arg Gln Ser Gly His His
1345                1350                1355                1360

Cys Ile Cys Asn Asn Gly Phe Tyr Gly Lys Asn Cys Glu Leu Ser Gly
            1365                1370                1375

Gln Asp Cys Asp Ser Asn Pro Cys Arg Val Gly Asn Cys Val Val Ala
        1380                1385                1390

Asp Glu Gly Phe Gly Tyr Arg Cys Glu Cys Pro Arg Gly Thr Leu Gly
    1395                1400                1405

Glu His Cys Glu Ile Asp Thr Leu Asp Glu Cys Ser Pro Asn Pro Cys
1410                1415                1420

Ala Gln Gly Ala Ala Cys Glu Asp Leu Leu Gly Asp Tyr Glu Cys Leu
1425                1430                1435                1440

Cys Pro Ser Lys Trp Lys Gly Lys Arg Cys Asp Ile Tyr Asp Ala Asn

```
                    1445                1450                1455
Tyr Pro Gly Trp Asn Gly Gly Ser Gly Ser Gly Asn Asp Arg Tyr Ala
           1460                1465                1470
Ala Asp Leu Glu Gln Gln Arg Ala Met Cys Asp Lys Arg Gly Cys Thr
      1475                1480                1485
Glu Lys Gln Gly Asn Gly Ile Cys Asp Ser Asp Cys Asn Thr Tyr Ala
      1490                1495                1500
Cys Asn Phe Asp Gly Asn Asp Cys Ser Leu Gly Ile Asn Pro Trp Ala
1505                1510                1515                1520
Asn Cys Thr Ala Asn Glu Cys Trp Asn Lys Phe Lys Asn Gly Lys Cys
           1525                1530                1535
Asn Glu Glu Cys Asn Asn Ala Ala Cys His Tyr Asp Gly His Asp Cys
           1540                1545                1550
Glu Arg Lys Leu Lys Ser Cys Asp Thr Leu Phe Asp Ala Tyr Cys Gln
      1555                1560                1565
Lys His Tyr Gly Asp Gly Phe Cys Asp Tyr Gly Cys Asn Asn Ala Glu
      1570                1575                1580
Cys Ser Trp Asp Gly Leu Asp Cys Glu Asn Lys Thr Gln Ser Pro Val
1585                1590                1595                1600
Leu Ala Glu Gly Ala Met Ser Val Val Met Leu Met Asn Val Glu Ala
           1605                1610                1615
Phe Arg Glu Ile Gln Ala Gln Phe Leu Arg Asn Met Ser His Met Leu
           1620                1625                1630
Arg Thr Thr Val Arg Leu Lys Lys Asp Ala Leu Gly His Asp Ile Ile
      1635                1640                1645
Ile Asn Trp Lys Asp Asn Val Arg Val Pro Glu Ile Glu Asp Thr Asp
      1650                1655                1660
Phe Ala Arg Lys Asn Lys Ile Leu Tyr Thr Gln Gln Val His Gln Thr
1665                1670                1675                1680
Gly Ile Gln Ile Tyr Leu Glu Ile Asp Asn Arg Lys Cys Thr Glu Cys
           1685                1690                1695
Phe Thr His Ala Val Glu Ala Ala Glu Phe Leu Ala Ala Thr Ala Ala
           1700                1705                1710
Lys His Gln Leu Arg Asn Asp Phe Gln Ile His Ser Val Arg Gly Ile
      1715                1720                1725
Lys Asn Pro Gly Asp Glu Asp Asn Gly Glu Pro Pro Ala Asn Val Lys
      1730                1735                1740
Tyr Val Ile Thr Gly Ile Ile Leu Val Ile Ile Ala Leu Ala Phe Phe
1745                1750                1755                1760
Gly Met Val Leu Ser Thr Gln Arg Lys Arg Ala His Gly Val Thr Trp
           1765                1770                1775
Phe Pro Glu Gly Phe Arg Ala Pro Ala Ala Val Met Ser Arg Arg Arg
           1780                1785                1790
Arg Asp Pro His Gly Gln Glu Met Arg Asn Leu Asn Lys Gln Val Ala
      1795                1800                1805
Met Gln Ser Gln Gly Val Gly Gln Pro Gly Ala His Trp Ser Asp Asp
      1810                1815                1820
Glu Ser Asp Met Pro Leu Pro Lys Arg Gln Arg Ser Asp Pro Val Ser
1825                1830                1835                1840
Gly Val Gly Leu Gly Asn Asn Gly Gly Tyr Ala Ser Asp His Thr Met
           1845                1850                1855
Val Ser Glu Tyr Glu Glu Ala Asp Gln Arg Val Trp Ser Gln Ala His
           1860                1865                1870
```

-continued

```
Leu Asp Val Val Asp Val Arg Ala Ile Met Thr Pro Pro Ala His Gln
    1875                1880                1885
Asp Gly Gly Lys His Asp Val Asp Ala Arg Gly Pro Cys Gly Leu Thr
    1890                1895                1900
Pro Leu Met Ile Ala Ala Val Arg Gly Gly Leu Asp Thr Gly Glu
1905                1910                1915                1920
Asp Ile Glu Asn Asn Glu Asp Ser Thr Ala Gln Val Ile Ser Asp Leu
            1925                1930                1935
Leu Ala Gln Gly Ala Glu Leu Asn Ala Thr Met Asp Lys Thr Gly Glu
            1940                1945                1950
Thr Ser Leu His Leu Ala Ala Arg Phe Ala Arg Ala Asp Ala Ala Lys
    1955                1960                1965
Arg Leu Phe His Ala Gly Ala Asp Ala Asn Cys Gln Asp Asn Thr Gly
    1970                1975                1980
Arg Thr Pro Leu His Ala Ala Val Ala Ala Asp Ala Met Gly Val Phe
1985                1990                1995                2000
Gln Ile Leu Leu Arg Asn Arg Ala Thr Asn Leu Asn Ala Arg Met His
            2005                2010                2015
Asp Gly Thr Thr Pro Leu Ile Leu Ala Ala Arg Leu Ala Ile Glu Gly
            2020                2025                2030
Met Val Glu Asp Leu Ile Thr Ala Asp Ala Asp Ile Asn Ala Ala Asp
    2035                2040                2045
Asn Ser Gly Lys Thr Ala Leu His Trp Ala Ala Ala Val Asn Asn Thr
    2050                2055                2060
Glu Ala Val Asn Ile Leu Leu Met His His Ala Asn Arg Asp Ala Gln
2065                2070                2075                2080
Asp Asp Lys Asp Glu Thr Pro Leu Phe Leu Ala Ala Arg Glu Gly Ser
            2085                2090                2095
Tyr Glu Ala Cys Lys Ala Leu Leu Asp Asn Phe Ala Asn Arg Glu Ile
            2100                2105                2110
Thr Asp His Met Asp Arg Leu Pro Arg Asp Val Ala Ser Glu Arg Leu
    2115                2120                2125
His His Asp Ile Val Arg Leu Leu Asp Glu His Val Pro Arg Ser Pro
    2130                2135                2140
Gln Met Leu Ser Met Thr Pro Gln Ala Met Ile Gly Ser Pro Pro Pro
2145                2150                2155                2160
Gly Gln Gln Gln Pro Gln Leu Ile Thr Gln Pro Thr Val Ile Ser Ala
            2165                2170                2175
Gly Asn Gly Gly Asn Asn Gly Asn Gly Asn Ala Ser Gly Lys Gln Ser
            2180                2185                2190
Asn Gln Thr Ala Lys Gln Lys Ala Ala Lys Lys Ala Lys Leu Ile Glu
    2195                2200                2205
Gly Ser Pro Asp Asn Gly Leu Asp Ala Thr Gly Ser Leu Arg Arg Lys
    2210                2215                2220
Ala Ser Ser Lys Lys Thr Ser Ala Ala Ser Lys Lys Ala Ala Asn Leu
2225                2230                2235                2240
Asn Gly Leu Asn Pro Gly Gln Leu Thr Gly Gly Val Ser Gly Val Pro
            2245                2250                2255
Gly Val Pro Pro Thr Asn Ser Ala Val Gln Ala Ala Ala Ala Ala
            2260                2265                2270
Ala Ala Val Ala Ala Met Ser His Glu Leu Glu Gly Ser Pro Val Gly
    2275                2280                2285
```

-continued

```
Val Gly Met Gly Gly Asn Leu Pro Ser Pro Tyr Asp Thr Ser Ser Met
    2290             2295             2300

Tyr Ser Asn Ala Met Ala Ala Pro Leu Ala Asn Gly Asn Pro Asn Thr
2305             2310             2315             2320

Gly Ala Lys Gln Pro Pro Ser Tyr Glu Asp Cys Ile Lys Asn Ala Gln
        2325             2330             2335

Ser Met Gln Ser Leu Gln Gly Asn Gly Leu Asp Met Ile Lys Leu Asp
        2340             2345             2350

Asn Tyr Ala Tyr Ser Met Gly Ser Pro Phe Gln Gln Glu Leu Leu Asn
    2355             2360             2365

Gly Gln Gly Leu Gly Met Asn Gly Asn Gly Gln Arg Asn Gly Val Gly
    2370             2375             2380

Pro Gly Val Leu Pro Gly Gly Leu Cys Gly Met Gly Gly Leu Ser Gly
2385             2390             2395             2400

Ala Gly Asn Gly Asn Ser Arg Glu Gln Gly Leu Ser Pro Pro Tyr Ser
        2405             2410             2415

Asn Gln Ser Pro Pro His Ser Val Gln Ser Ser Leu Ala Leu Ser Pro
        2420             2425             2430

His Ala Tyr Leu Gly Ser Pro Ser Pro Ala Lys Ser Leu Pro Ser Leu
        2435             2440             2445

Pro Thr Ser Pro Thr His Ile Gln Ala Met Arg His Ala Thr Gln Gln
    2450             2455             2460

Lys Gln Phe Gly Gly Ser Asn Leu Asn Ser Leu Leu Gly Gly Ala Asn
2465             2470             2475             2480

Gly Gly Gly Val Val Gly Gly Gly Gly Gly Gly Gly Gly Gly Val Gly
        2485             2490             2495

Gln Gly Pro Gln Asn Ser Pro Val Ser Leu Gly Ile Ile Ser Pro Thr
        2500             2505             2510

Gly Ser Asp Met Gly Ile Met Leu Ala Pro Pro Gln Ser Ser Lys Asn
        2515             2520             2525

Ser Ala Ile Met Gln Thr Ile Ser Pro Gln Gln Gln Gln Gln Gln Gln
        2530             2535             2540

Gln Gln Gln Gln Gln Gln His Gln Gln Gln Gln Gln Gln Gln Gln Gln
2545             2550             2555             2560

Gln Gln Gln Gln Gln Gln Gln Gln Leu Gly Gly Leu Glu Phe Gly Ser
        2565             2570             2575

Ala Gly Leu Asp Leu Asn Gly Phe Cys Gly Ser Pro Asp Ser Phe His
        2580             2585             2590

Ser Gly Gln Met Asn Pro Pro Ser Ile Gln Ser Ser Met Ser Gly Ser
        2595             2600             2605

Ser Pro Ser Thr Asn Met Leu Ser Pro Ser Ser Gln His Asn Gln Gln
    2610             2615             2620

Ala Phe Tyr Gln Tyr Leu Thr Pro Ser Ser Gln His Ser Gly Gly His
2625             2630             2635             2640

Thr Pro Gln His Leu Val Gln Thr Leu Asp Ser Tyr Pro Thr Pro Ser
            2645             2650             2655

Pro Glu Ser Pro Gly His Trp Ser Ser Ser Ser Pro Arg Ser Asn Ser
        2660             2665             2670

Asp Trp Ser Glu Gly Val Gln Ser Pro Ala Ala Asn Asn Leu Tyr Ile
    2675             2680             2685

Ser Gly Gly His Gln Ala Asn Lys Gly Ser Glu Ala Ile Tyr Ile
    2690             2695             2700
```

ACTIVATED FORMS OF NOTCH AND METHODS BASED THEREON

This application is a continuation-in-part application of U.S. application Ser. No. 08/899,232 filed Jul. 23, 1997, now U.S. Pat. No. 6,436,650, which is incorporated herein in its entirety.

This invention was made with government support under grant number NS 26084 awarded by the National Institutes of Health. The government has certain rights in the invention.

1. FIELD OF THE INVENTION

The present invention is directed to methods for detecting or measuring Notch activation by observing or measuring the appearance of Notch on the cell surface or by observing or measuring Notch cleavage products that are indicative of Notch activation. The present invention is also directed to methods for detecting a molecule that modulates Notch activation by observing or measuring a change in the amount of Notch expressed on the cell surface or a change in the amount or pattern of Notch cleavage products. The present invention is also directed to a substantially purified activated heterodimeric form of Notch and pharmaceutical compositions and kits thereof.

2. BACKGROUND OF THE INVENTION

Genetic and molecular studies have led to the identification of a group of genes which define distinct elements of the Notch signaling pathway. While the identification of these various elements has come exclusively from Drosophila using genetic tools as the initial guide, subsequent analyses have lead to the identification of homologous proteins in vertebrate species including humans. FIG. 1 depicts the molecular relationships between the known Notch pathway elements as well as their subcellular localization (Artavanis-Tsakonas et al., 1995, Science 268:225–232).

The Drosophila Notch gene encodes an ~300 kD transmembrane protein that acts as a receptor in a cell-cell signaling mechanism controlling cell fate decisions throughout development (reviewed, e.g., in Artavanis-Tsakonas et al., 1995, Science 268:225–232). Closely related homologs of Drosophila Notch have been isolated from a number of vertebrate species, including humans, with multiple paralogs representing the single Drosophila gene in vertebrate genomes. The isolation of cDNA clones encoding the C-terminus of a human Notch paralog, originally termed hN, has been reported (Stifani et al., 1992, Nature Genetics 2:119–127). The encoded protein is designated human Notch2 because of its close relationship to the Notch2 proteins found in other species (Weinmaster et al., 1992, Development 116:931–941). The hallmark Notch2 structures are common to all the Notch-related proteins, including, in the extracellular domain, a stretch of 34 to 36 tandem Epidermal Growth Factor-like (EGF) repeats and three Lin-12/Notch repeats (LN repeats), and, in the intracellular domain, 6 Ankyrin repeats and a PEST-containing region. Like Drosophila Notch and the related *C. elegans* genes lin-12 and glp-1 (Sternberg, 1993, Current Biology 3:763–765; Greenwald, 1994, Current Opinion in Genetics and Development 4:556–562), the vertebrate Notch homologs play a role in a variety of developmental processes by controlling cell fate decisions (reviewed, e.g., in Blaumueller and Artavanis-Tsakonas, 1997, Persp. on Dev. Neurobiol. 4:325–343). (For further human Notch sequences, see International Publication WO 92/19734.)

The extracellular domain of Notch carries 36 Epidermal Growth Factor-like (EGF) repeats, two of which (repeats 11 and 12) have been implicated in interactions with the Notch ligands Serrate and Delta. Delta and Serrate are membrane bound ligands with EGF homologous extracellular domains, which interact physically with Notch on adjacent cells to trigger signaling.

Functional analyses involving the expression of truncated forms of the Notch receptor have indicated that receptor activation depends on the six cdc10/ankyrin repeats in the intracellular domain. Deltex and Suppressor of Hairless, whose over-expression results in an apparent activation of the pathway, associate with those repeats.

Deltex is a cytoplasmic protein which contains a ring zinc finger. Suppressor of Hairless on the other hand, is the Drosophila homologue of CBF1, a mammalian DNA binding protein involved in the Epstein-Barr virus-induced immortalization of B cells. It has been demonstrated that, at least in cultured cells, Suppressor of Hairless associates with the cdc10/ankyrin repeats in the cytoplasm and translocates into the nucleus upon the interaction of the Notch receptor with its ligand Delta on adjacent cells (Fortini and Artavanis, 1994, Cell 79:273–282). The association of Hairless, a novel nuclear protein, with Suppressor of Hairless has been documented using the yeast two hybrid system; therefore, it is believed that the involvement of Suppressor of Hairless in transcription is modulated by Hairless (Brou et al., 1994, Genes Dev. 8:2491; Knust et al. 1992, Genetics 129:803).

Finally, it is known that Notch signaling results in the activation of at least certain basic helix-loop-helix (bHLH) genes within the Enhancer of Split complex (Delidakis et al., 1991, Genetics 129:803). Mastermind encodes a novel ubiquitous nuclear protein whose relationship to Notch signaling remains unclear but is involved in the Notch pathway as shown by genetic analysis (Smoller et al., 1990, Genes Dev. 4:1688).

The generality of the Notch pathway manifests itself at different levels. At the genetic level, many mutations exist which affect the development of a very broad spectrum of cell types in Drosophila. Knockout mutations in mice are embryonic lethals consistent with a fundamental role for Notch function (Swiatek et al., 1994, Genes Dev. 8:707). Mutations in the Notch pathway in the hematopoietic system in humans are associated with lymphoblastic leukemia (Ellison et al., 1991, Cell 66:649–661). Finally the expression of mutant forms of Notch in developing Xenopus embryos interferes profoundly with normal development (Coffman et al., 1993, Cell 73:659). Increased level of Notch expression is found in some malignant tissue in humans (International Publication WO 94/07474).

The expression patterns of Notch in the Drosophila embryo are complex and dynamic. The Notch protein is broadly expressed in the early embryo, and subsequently becomes restricted to uncommitted or proliferative groups of cells as development proceeds. In the adult, expression persists in the regenerating tissues of the ovaries and testes (reviewed in Fortini et al., 1993, Cell 75:1245–1247; Jan et al., 1993, Proc. Natl. Acad. Sci. USA 90:8305–8307; Sternberg, 1993, Curr. Biol. 3:763–765; Greenwald, 1994, Curr. Opin. Genet. Dev. 4:556–562; Artavanis-Tsakonas et al., 1995, Science 268:225–232). Studies of the expression of Notch1, one of three known vertebrate homologs of Notch, in zebrafish and Xenopus, have shown that the general patterns are similar; with Notch expression associated in general with non-terminally differentiated, proliferative cell populations. Tissues with high expression levels include the developing brain, eye and neural tube (Coffman et al., 1990, Science 249:1438–1441; Bierkamp et al., 1993, Mech. Dev. 43:87–100). While studies in mammals have shown the expression of the corresponding Notch homologs to begin later in development, the proteins are expressed in dynamic patterns in tissues undergoing cell fate determination or rapid proliferation (Weinmaster et al., 1991, Development 113:199–205; Reaume et al., 1992, Dev. Biol. 154:377–387; Stifani et al., 1992, Nature Genet. 2:119–127; Weinmaster et al., 1992, Development 116:931–941; Kopan et al., 1993, J. Cell Biol. 121:631–641; Lardelli et al., 1993, Exp. Cell Res. 204:364–372; Lardelli et al., 1994, Mech. Dev. 46:123–136; Henrique et al., 1995, Nature 375:787–790; Horvitz et al., 1991, Nature 351:535–541; Franco del Amo et al., 1992, Development 115:737–744). Among the tissues in which mammalian Notch homologs are first expressed are the pre-somitic mesoderm and the developing neuroepithelium of the embryo. In the pre-somitic mesoderm, expression of Notch1 is seen in all of the migrated mesoderm, and a particularly dense band is seen at the anterior edge of pre-somitic mesoderm. This expression has been shown to decrease once the somites have formed, indicating a role for Notch in the differentiation of somatic precursor cells (Reaume et al., 1992, Dev. Biol. 154:377–387; Horvitz et al., 1991, Nature 351:535–541). Similar expression patterns are seen for mouse Delta (Simske et al., 1995, Nature 375:142–145).

Within the developing mammalian nervous system, expression patterns of Notch homologue have been shown to be prominent in particular regions of the ventricular zone of the spinal cord, as well as in components of the peripheral nervous system, in an overlapping but non-identical pattern. Notch expression in the nervous system appears to be limited to regions of cellular proliferation, and is absent from nearby populations of recently differentiated cells (Weinmaster et al., 1991, Development 113:199–205; Reaume et al., 1992, Dev. Biol. 154:377–387; Weinmaster et al., 1992, Development 116:931–941; Kopan et al., 1993, J. Cell Biol. 121:631–641; Lardelli et al., 1993, Exp. Cell Res. 204:364–372; Lardelli et al., 1994, Mech. Dev. 46:123–136; Henrique et al., 1995, Nature 375:787–790; Horvitz et al., 1991, Nature 351:535–541). A rat Notch ligand is also expressed within the developing spinal cord, in distinct bands of the ventricular zone that overlap with the expression domains of the Notch genes. The spatio-temporal expression pattern of this ligand correlates well with the patterns of cells committing to spinal cord neuronal fates, which demonstrates the usefulness of Notch as a marker of populations of cells for neuronal fates (Henrique et al., 1995, Nature 375:787–790). This has also been suggested for vertebrate Delta homologs, whose expression domains also overlap with those of Notch1 (Larsson et al., 1994, Genomics 24:253–258; Fortini et al., 1993, Nature 365:555–557; Simske et al., 1995, Nature 375:142–145). In the cases of the Xenopus and chicken homologs, Delta is actually expressed only in scattered cells within the Notch1 expression domain, as would be expected from the lateral specification model, and these patterns "foreshadow" future patterns of neuronal differentiation (Larsson et al., 1994, Genomics 24:253–258; Fortini et al., 1993, Nature 365:555–557).

Other vertebrate studies of particular interest have focused on the expression of Notch homologs in developing sensory structures, including the retina, hair follicles and tooth buds. In the case of the Xenopus retina, Notch1 is expressed in the undifferentiated cells of the central marginal zone and central retina (Coffman et al., 1990, Science 249:1439–1441; Mango et al., 1991, Nature 352:811–815).

Studies in the rat have also demonstrated an association of Notch1 with differentiating cells in the developing retina have been interpreted to suggest that Notch1 plays a role in successive cell fate choices in this tissue (Lyman et al., 1993, Proc. Natl. Acad. Sci. USA 90:10395–10399).

A detailed analysis of mouse Notch1 expression in the regenerating matrix cells of hair follicles was undertaken to examine the potential participation of Notch proteins in epithelial/mesenchymal inductive interactions (Franco del Amo et al., 1992, Development 115:737–744). Such a role had originally been suggested for Notch1 based on its expression in rat whiskers and tooth buds (Weinmaster et al., 1991, Development 113:199–205). Notch1 expression was instead found to be limited to subsets of non-mitotic, differentiating cells that are not subject to epithelial/mesenchymal interactions, a finding that is consistent with Notch expression elsewhere.

Expression studies of Notch proteins in human tissue and cell lines have also been reported. The aberrant expression of a truncated Notch1 RNA in human T-cell leukemia results from a translocation with a breakpoint in Notch1 (Ellisen et al., 1991, Cell 66:649–661). A study of human Notch1 expression during hematopoiesis has suggested a role for Notch1 in the early differentiation of T-cell precursors (Mango et al., 1994, Development 120:2305–2315). Additional studies of human Notch1 and Notch2 expression have been performed on adult tissue sections including both normal and neoplastic cervical and colon tissue. Notch1 and Notch2 appear to be expressed in overlapping patterns in differentiating populations of cells within squamous epithelia of normal tissues that have been examined and are clearly not expressed in normal columnar epithelia, except in some of the precursor cells. Both proteins are expressed in neoplasias, in cases ranging from relatively benign squamous metaplasias to cancerous invasive adenocarcinomas in which columnar epithelia are replaced by these tumors (Mello et al., 1994, Cell 77:95–106).

Insight into the developmental role and the general nature of Notch signaling has emerged from studies with truncated, constitutively activated forms of Notch in several species. These recombinantly engineered Notch forms, which lack extracellular ligand-binding domains, resemble the naturally occurring oncogenic variants of mammalian Notch proteins and are constitutively activated using phenotypic criteria (Greenwald, 1994, Curr. Opin. Genet. Dev. 4:556; Fortini et al., 1993, Nature 365:555–557; Coffman et al., 1993, Cell 73:659–671; Struhl et al., 1993, Cell 69:1073; Rebay et al., 1993, Cell 74: 319–329; Kopan et al., 1994, Development 120:2385; Roehl et al., 1993, Nature 364:632).

Ubiquitous expression of activated Notch in the Drosophila embryo suppresses neuroblast segregation without impairing epidermal differentiation (Struhl et al., 1993, Cell 69:331; Rebay et al., 1993, Cell 74:319–329).

Persistent expression of activated Notch in developing imaginal epithelia likewise results in an overproduction of epidermis at the expense of neural structures (Struhl et al., 1993, Cell 69:331).

Neuroblast segregation occurs in temporal waves that are delayed but not prevented by transient expression of activated Notch in the embryo (Struhl et al., 1993, Cell 69:331).

Transient expression in well-defined cells of the rosophila eye imaginal disc causes the cells to ignore their normal inductive cues and to adopt alternative cell fates (Fortini et al., 1993, Nature 365:555–557).

Studies utilizing transient expression of activated Notch in either the Drosophila embryo or the eye disc indicate that once Notch signaling activity has subsided, cells may recover and differentiate properly or respond to later developmental cues (Fortini et al., 1993, Nature 365:555–557; Struhl et al., 1993, Cell 69:331).

For a general review on the Notch pathway and Notch signaling, see Artavanis-Tsakonas et al., 1995, Science 268:225–232.

Ligands, cytoplasmic effectors and nuclear elements of Notch signaling have been identified in Drosophila, and vertebrate counterparts have also been cloned (reviewed in Artavanis-Tsakonas et al., 1995, Science 268:225–232). While protein interactions between the various elements have been documented, the biochemical nature of Notch signaling remains elusive. Expression of truncated forms of Notch reveal that Notch proteins without transmembrane and extracellular domains are translocated to the nucleus both in transgenic flies and in transfected mammalian or Drosophila cells (Lieber et al., 1993, Genes and Development 7:1949–1965; Fortini et al., 1993, Nature 365:555–557; Ahmad et al., 1995, Mechanisms of Development 53:78–85; Zagouras et al., 1995, Proc. Natl. Acad. Sci. USA 92:6414–6418). Sequence comparisons between mammalian and Drosophila Notch molecules, along with deletion analysis, have found two nuclear localization sequences that reside on either side of the Ankyrin repeats (Stifani et al., 1992, Nature Genetics 2:119–127; Lieber et al., 1993, Genes and Development 7:1949–1965; Kopan et al., 1994, Development 120:2385–2396). These findings prompted the speculation that Notch may be directly participating in nuclear events by means of a proteolytic cleavage and subsequent translocation of the intracellular fragment into the nucleus. However, conclusive functional evidence for such a hypothesis remained elusive (Artavanis-Tsakonas et al., 1995, Science 268:225–232) until the disclosure of Schroeter et al., 1998, Nature 393:382–386. Schroeter et al. demonstrated that Notch1, upon ligand binding, is cleaved between amino acid G1743 and V1744 releasing the intracellular domain. The released intracellular domain translocates into the nucleus, and through interaction with members of the CSL (CBF-1, Su(H), Lag-1) family of DNA binding proteins, activates transcription.

In a separate study, Logeat et al., 1998, Proc. Natl. Acad. Sci. USA 95:8108–8112 (Logeat et al.), have demonstrated that human Notch1 is constitutively cleaved by the convertase furin at the carboxyl side of the sequence ArgGlnArgArg (amino acids 1651–1654), which sequence is located between the transmembrane domain and the Lin-12/Notch repeats. The cleavage of Notch1 by furin results in the cell surface expression of a heterodimeric functional receptor.

Citation or identification of any reference in Section 2 or any other section of this application shall not be construed as an admission that such reference is available as prior art to the present invention.

3. SUMMARY OF THE INVENTION

The present invention is directed to methods for detecting or measuring Notch activation by observing or measuring the appearance of Notch on the cell surface or by observing or measuring Notch cleavage products that are indicative of Notch activation. In one aspect of this embodiment of the invention, the method for detecting or measuring Notch activation in a cell comprises detecting or measuring the expression of Notch on the surface of said cell, wherein the presence and amount of Notch on the surface indicates the presence and amount, respectively, of Notch activation. In another aspect, the method comprises detecting or measuring the expression of one or more Notch cleavage products selected from the group consisting of $N^{EC}$ and $N^{TM}$. In yet another aspect, the method comprises detecting or measuring one or more fragments of Notch selected from the group consisting of an amino-terminal fragment of full-length Notch terminating between the epidermal growth factor-like repeat domain and the transmembrane domain (in particular, between the Lin-12/Notch repeats and the transmembrane domain) of full-length Notch, and a carboxy-terminal fragment of full-length Notch with its amino terminus situated between the epidermal growth factor-like repeat domain and the transmembrane domain (in particular, between the Lin-12/Notch repeats and the transmembrane domain), or detecting or measuring one or more fragments of Notch selected from the group consisting of Notch fragments having a molecular weight of about 270, 200, 170, 140, 110, 100, 90 and 85 kilodaltons. In yet another aspect, the method comprises detecting or measuring a Notch heterodimer containing a reducing agent-sensitive linkage, in particular, a non-covalent, metal ion-dependent (e.g., calcium ion-dependent) linkage.

The present invention is based, at least in part, on the discovery that Notch in its active form, i.e., the form that mediates signal transduction and that binds Notch ligands such as Delta, is a heterodimer of two Notch cleavage products, an about (±10%) 180 kilodaltons (kDa) subunit ($N^{EC}$) and an about (±10%) 110 kDa subunit ($N^{TM}$), which are tethered together through a reducing agent-sensitive linkage, in particular, a non-covalent, metal ion-dependent (e.g., calcium ion-dependent) linkage. Full length Notch is not expressed on the cell surface and is ligand inaccessible. As shown by way of example infra, the two subunits arise due to a proteolytic cleavage of the full length Notch molecule in the trans-Golgi at a site in Notch amino-terminal to the transmembrane domain and carboxy-terminal to the EGF repeat region, thus generating an extracellular fragment ($N^{EC}$) of about 180 kDa and a transmembrane/intracellular fragment ($N^{TM}$) of about 110 kDa. The detection of full length Notch and of Notch cleavage products, as well as Notch that is present on the cell surface, can be carried out by methods well known to those of skill in the art, e.g., precipitation or binding to an immobilized binding partner (e.g., on a plate or column), e.g., anti-Notch antibodies or ligands of Notch, such as Delta and Serrate.

The detection or measurement of Notch activation is important in the study and manipulation of differentiation processes, since Notch plays a key role in cell fate (differentiation) determination. Also, disorders of cell fate, in particular hyperproliferative (e.g., cancer) or hypoproliferative disorders, involving aberrant or undesirable levels of active Notch expression can be diagnosed or screened for by detecting such active Notch expression, as described more fully infra. Molecules that modulate Notch function are important tools for studying and manipulating differentiation processes, e.g., in expanding cell populations without substantial differentiation (International Publication WO 97/11716), in cancer studies and therapy (International Publication WO 94/07474), and differentiation studies on normal tissue.

In another embodiment, the present invention is also directed to methods for identifying a molecule that modulates Notch activation by detecting or measuring a change in the amount of Notch expressed on the cell surface or a change in the amount or pattern of Notch cleavage products. In one aspect of this embodiment of the invention, the method for identifying a modulator of Notch activation comprises providing a cell with a candidate modulator molecule and detecting or measuring the amount of Notch on the surface of the cell, in which a difference in the presence or amount compared to a cell not contacted with the candidate molecule indicates that the candidate molecule modulates Notch activation. In another aspect, the method for identifying a modulator of Notch activation comprises providing a cell with a candidate modulator molecule and detecting or measuring the expression by the cell of one or more Notch cleavage products selected from the group consisting of $N^{EC}$ and $N^{TM}$, in which a difference in the presence or amount of said one or more cleavage products compared to a Notch cell not contacted with the candidate molecule indicates that the molecule modulates Notch activity.

In an alternative aspect, the method for identifying a modulator of Notch activation comprises contacting a candidate modulator molecule with a full length Notch in the presence of a composition comprising cellular proteins, under conditions conducive to cleavage of the full-length Notch by one or more components of the composition and detecting or measuring the amount of Notch cleavage products $N^{EC}$ and $N^{TM}$ that result, in which a difference in the presence or amount of said Notch cleavage products compared to a full-length Notch in presence of said composition not contacted with the candidate molecule indicates that the molecule modulates Notch activity.

The present invention is also directed to a substantially purified active form of Notch which comprises Notch fragments tethered together through a reducing agent-sensitive linkage, particularly, a non-covalent, metal ion-dependent linkage, and pharmaceutical compositions and kits thereof.

4. BRIEF DESCRIPTION OF THE FIGURES

FIG. 1 is a schematic diagram of the Notch signaling pathway. The Notch receptor can bind to either Delta or Serrate through its extracellular domain. Ligand binding can result in receptor multimerization that is stabilized by interactions between the intracellular ankyrin repeats of Notch and the cytoplasmic protein Deltex. These events can control the nuclear translocation of the DNA-binding protein Suppressor of Hairless and its known association with the Hairless protein. The transcriptional induction of the Enhancer of Split basic helix-loop-helix (bHLH) genes appears to depend on Notch signaling.

Figure 2A:
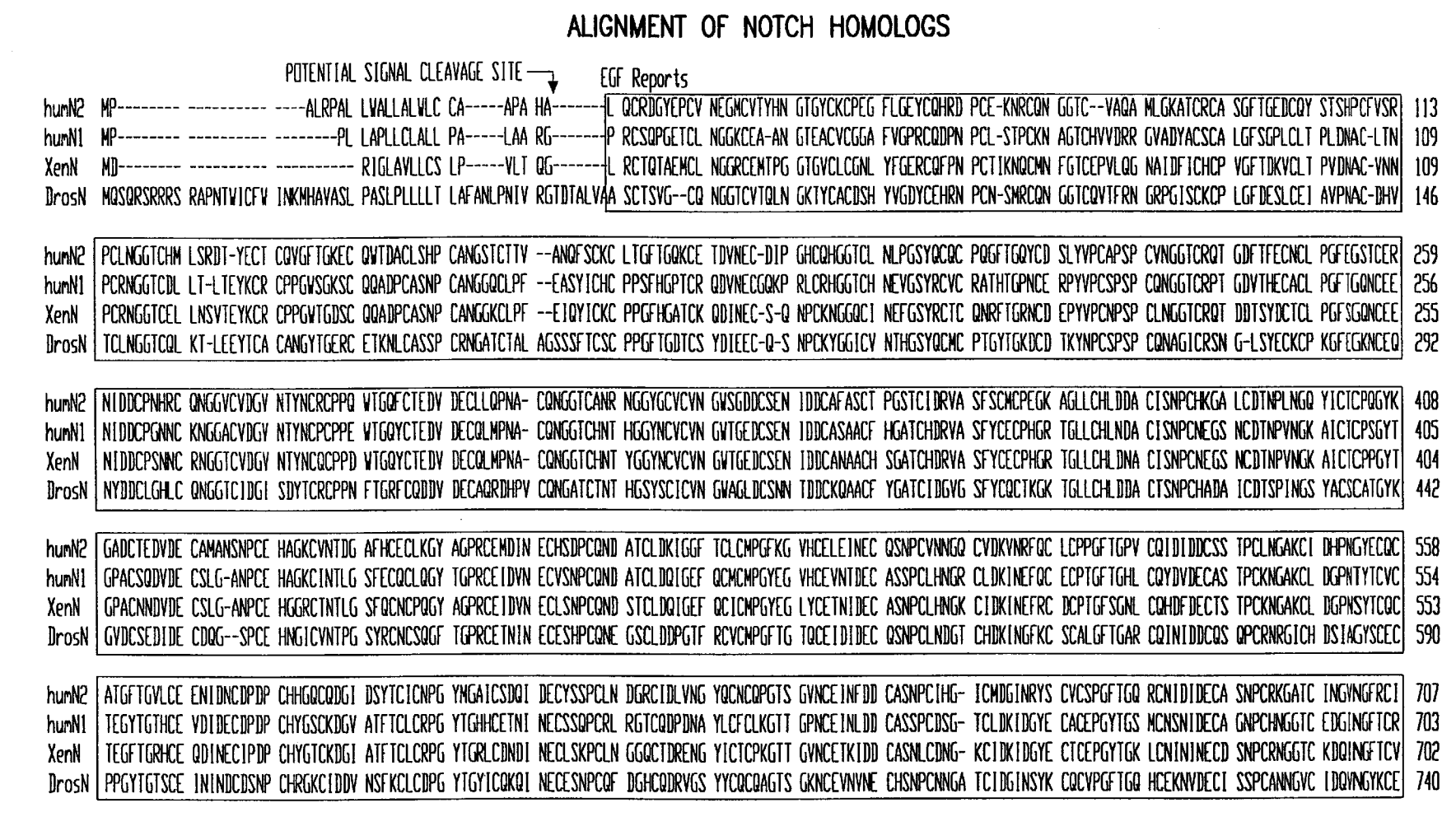
Figure 2B:
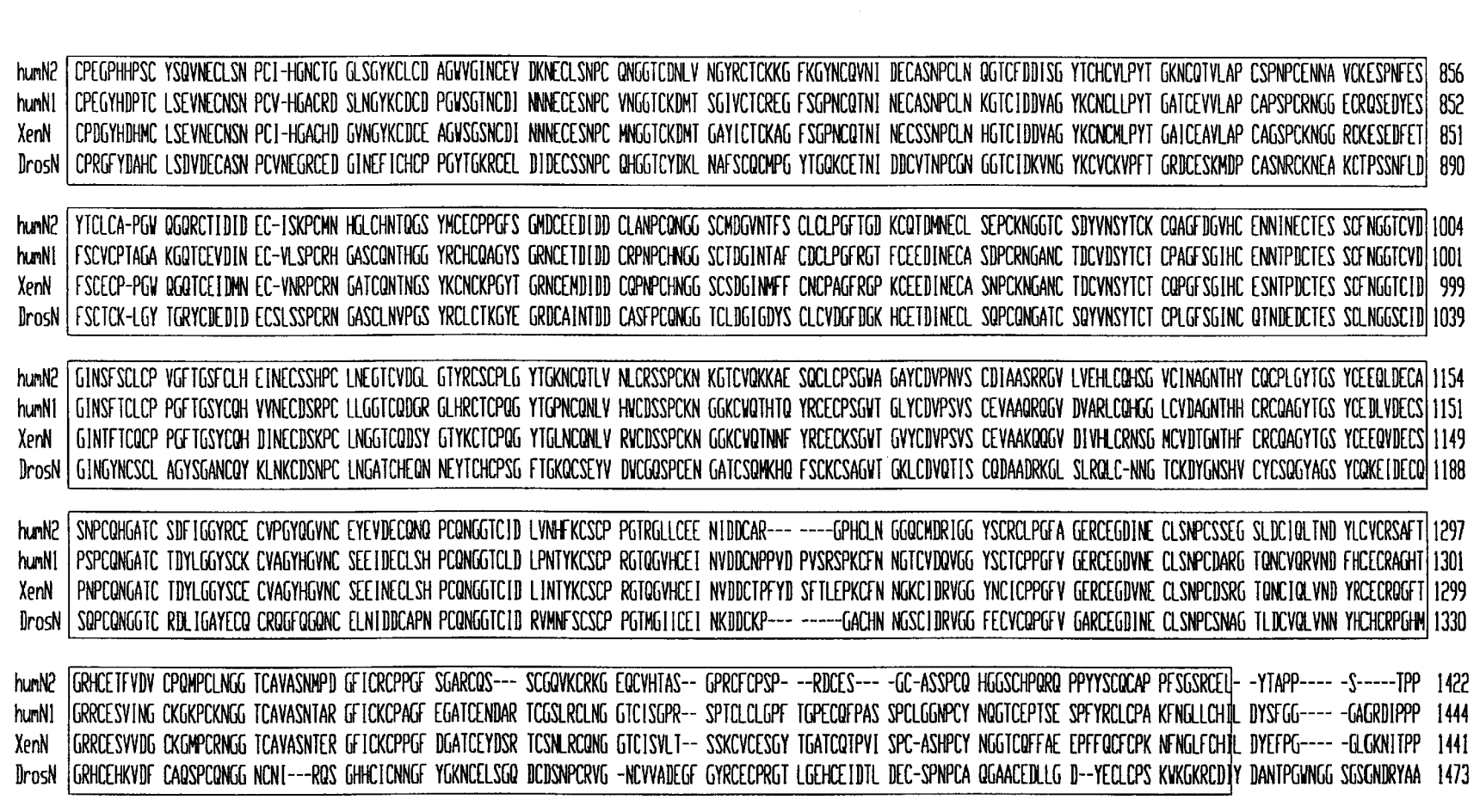
Figure 2C:
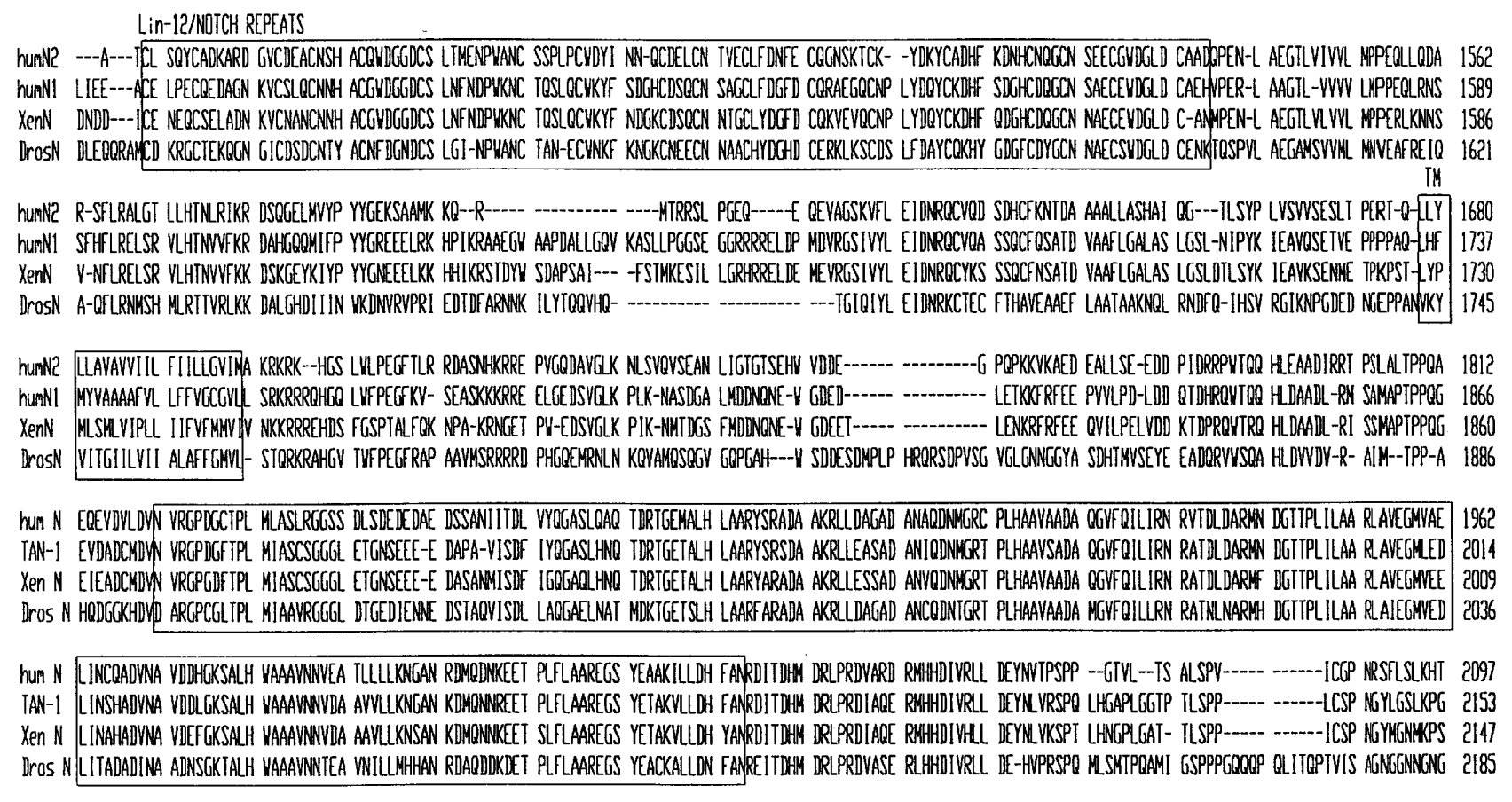
Figure 2D:
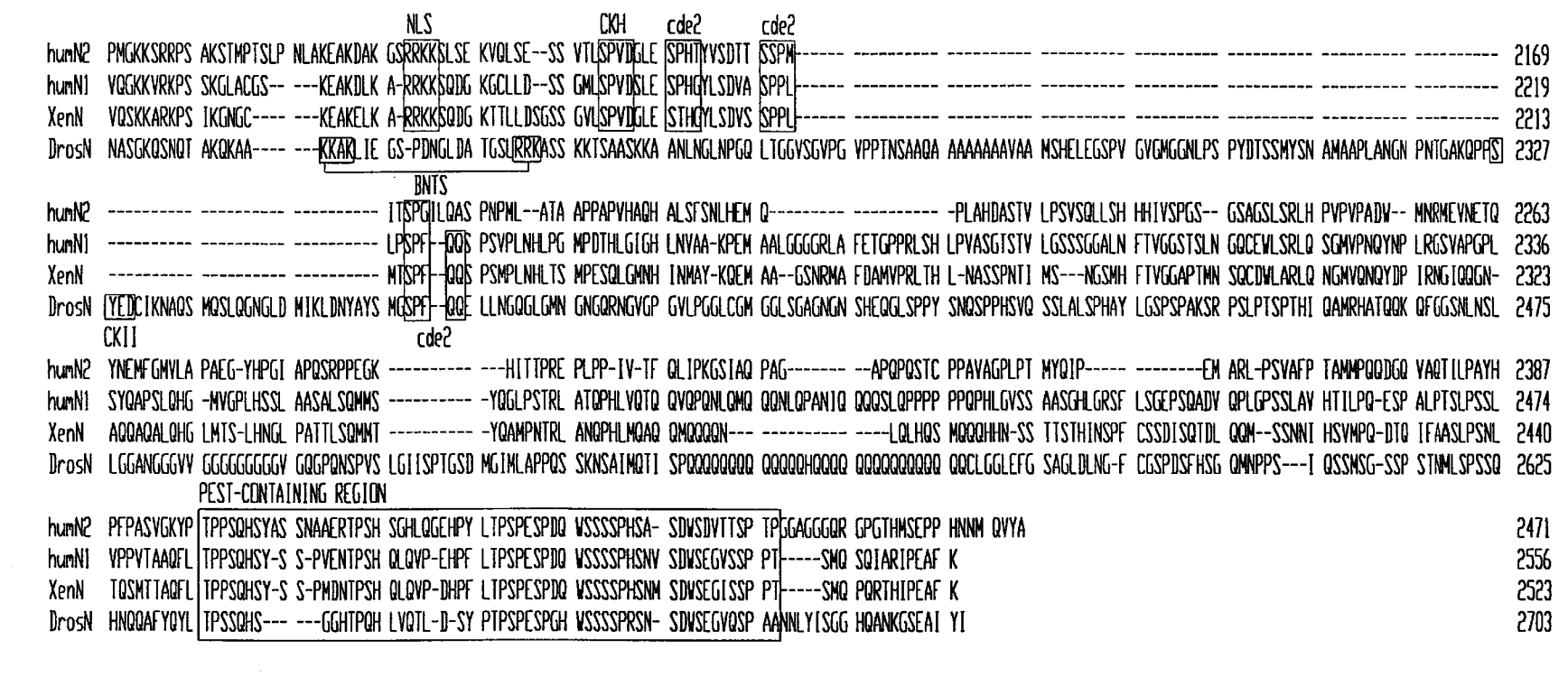

FIGS. 2A–2D depict is a Notch homolog sequence comparison. The human Notch2 (humN2) (SEQ ID NO:1), human Notch1 (humN1) (SEQ ID NO:2), Xenopus Notch/Xotch (XenN) (SEQ ID NO:3), and Drosophila Notch (DrosN) (SEQ ID NO:4) protein sequences are aligned, with names indicated to the left and numbering to the right (Wharton et al., 1985, Cell 43:567–581; Coffman et al., 1990, Science 249:1438–1441; Ellisen et al., 1991, Cell 66:649–661; Stifani et al., 1992, Nature Genetics 2:119–127). Major Notch protein motifs are enclosed in boxes. Starting from the N-terminal, the boxed regions indicate: EGF repeats, Lin-12/Notch (LN) repeats, transmembrane domain (TM), Ankyrin repeats, and PEST-containing region. Also indicated are the putative CcN motif components (Stifani et al., 1992, Nature Genetics 2:119–127) nuclear localization signal (NLS, BNTS) and putative CKII and cdc2 phosphorylation sites. The calculated signal cleavage site is indicated with an arrow.

Figure 3A:
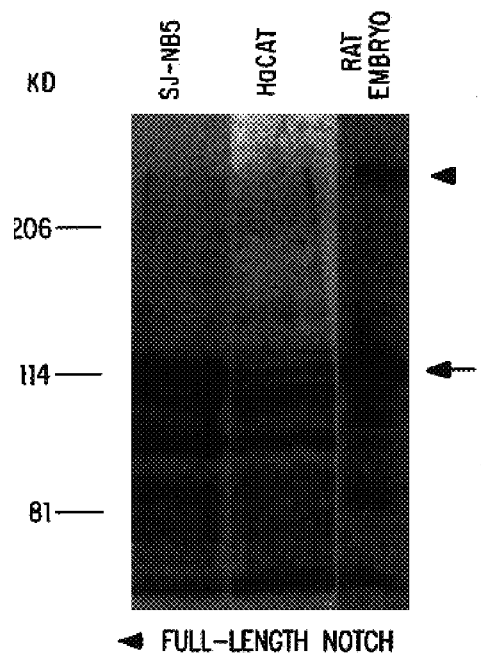
Figure 3B:
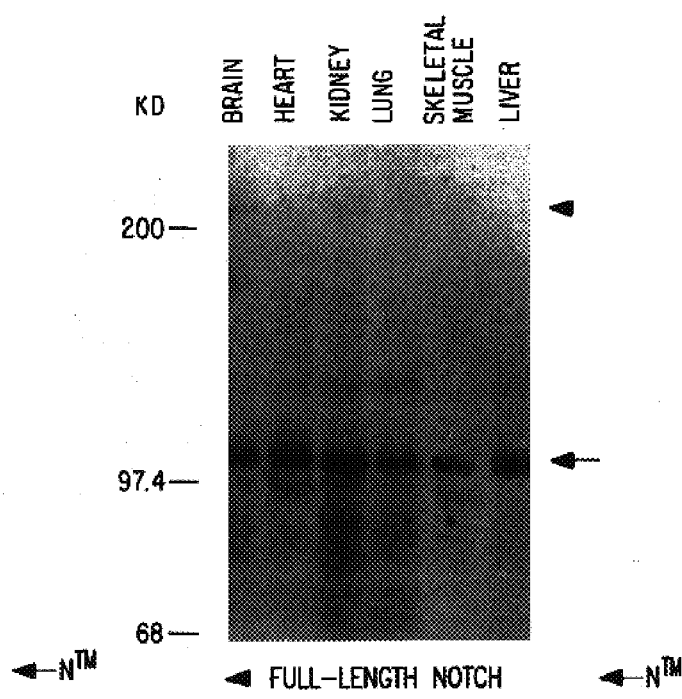
Figure 3C:
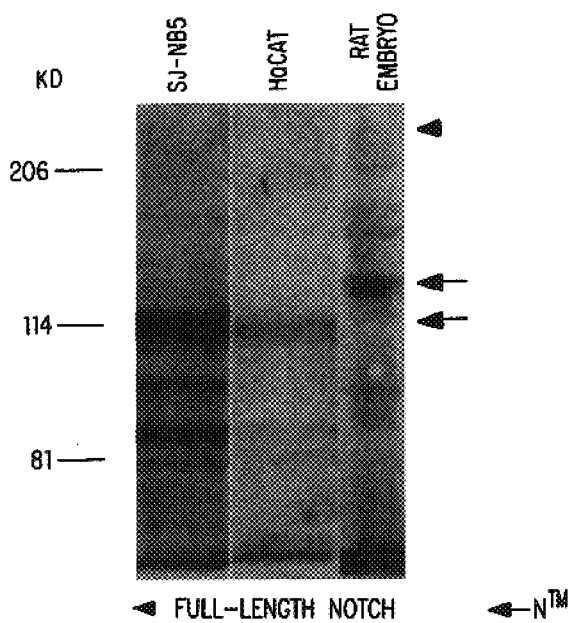
Figure 3D:
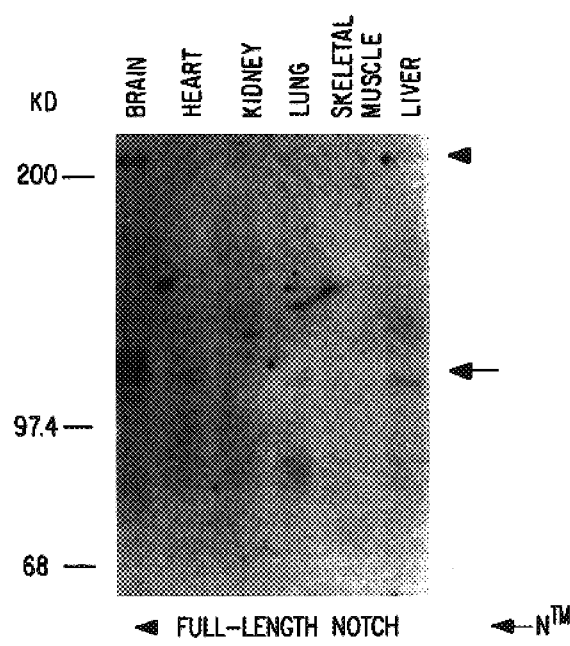
Figure 3E:
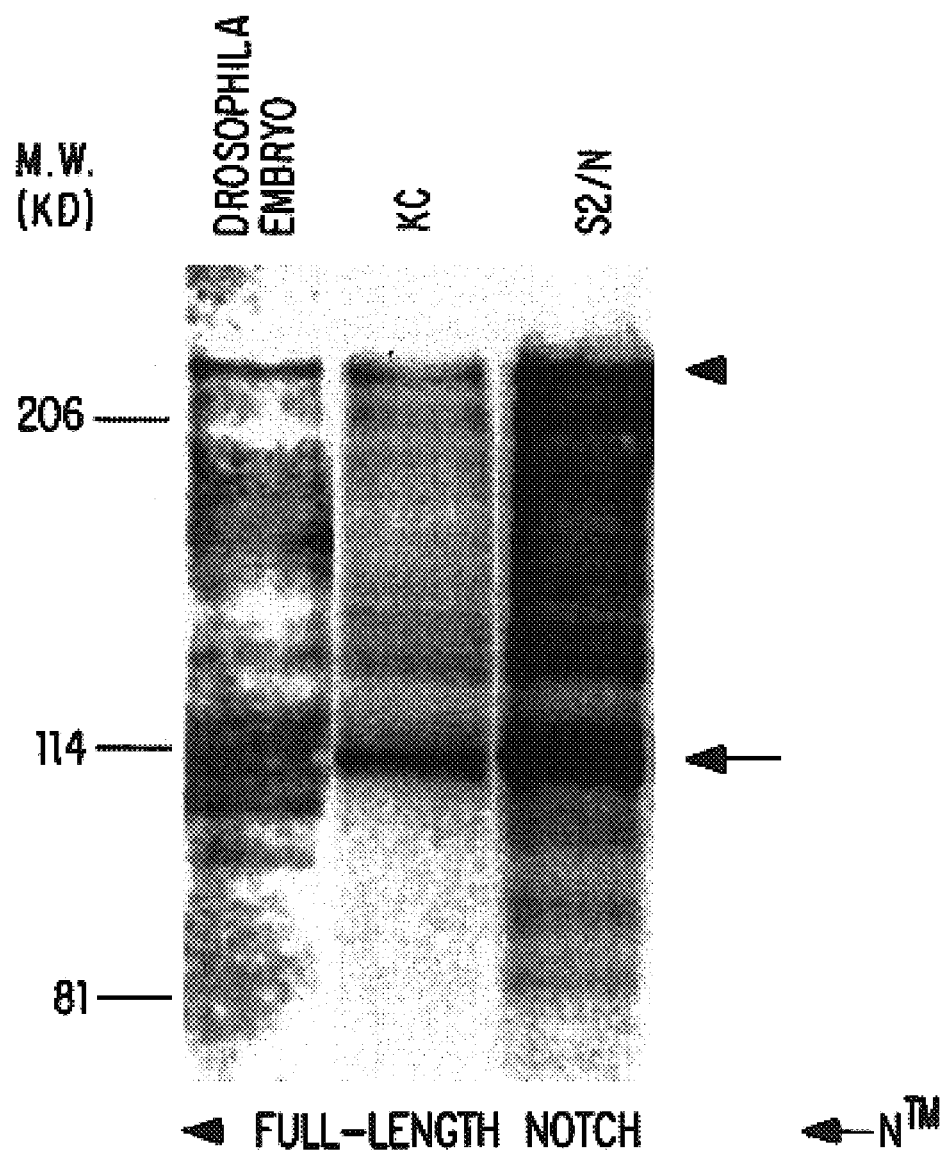

FIGS. 3A–3E are Western blot analyses of human cell lines, human tissues, Drosophila cell lines, rat and Drosophila embryos. The cell source of each lysate is indicated above the lanes. Notch2 expression was monitored with antibody bhN6D and Notch1 expression with antibody bTAN20. Both recognize intracellular epitopes of the protein (Zagouras et al., 1995, Proc. Natl. Acad. Sci. USA 92:6414–6418). FIGS. 3A and 3B show Notch2 expression. FIGS. 3C and 3D show Notch1 expression. FIG. 3E shows the expression of Drosophila Notch in embryos, Drosophila KC cultured cells, which endogenously express Notch, and Drosophila S2 cells, which do not endogenously express Notch but have been stably transfected with a Notch expression vector. The antibody used (9C6) recognizes an intracellular epitope (Fehon et al., 1990, Cell 61:523–534). In all the panels the 110 kDa major breakdown product ($N^{TM}$) and the position of the full-length Notch protein are indicated. Molecular weight markers are shown on the left of each panel.

Figure 4:
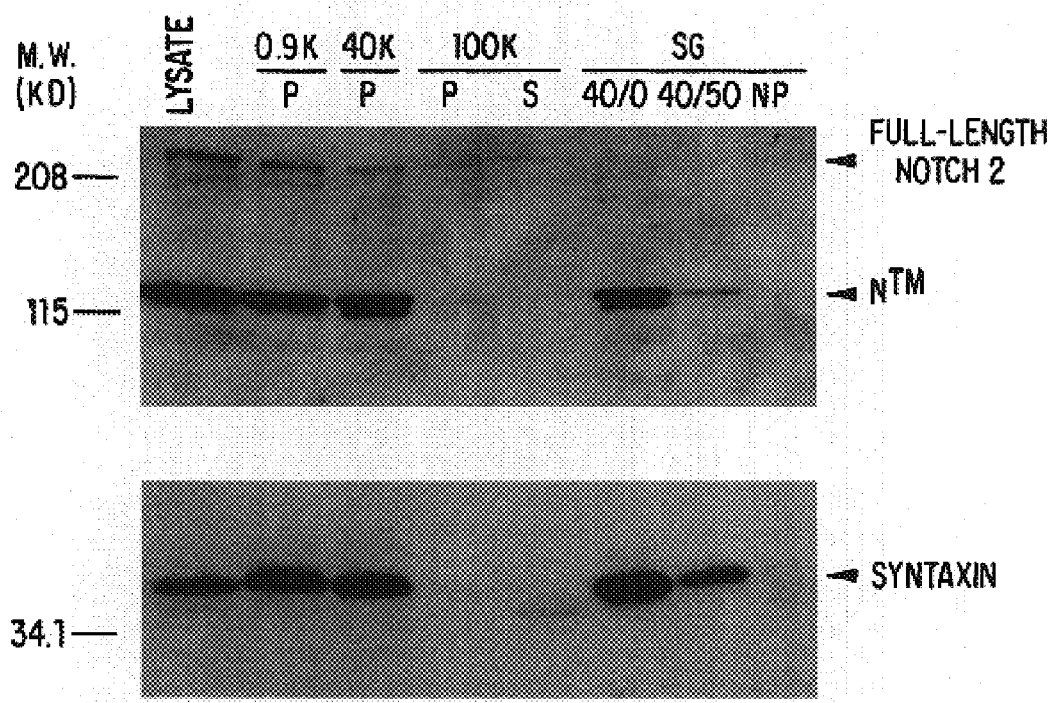

FIG. 4 shows the subcellular location of the 110 kDa ($N^{TM}$) fragment. Subcellular fractionation of SJ-NB5 cells followed by SDS-PAGE and Western blot with a Notch2 antibody raised against an intracellular epitope (bhN6D). Whole cell lysate is shown on the left lane. This lysate was centrifuged at 900×g and the pellet (0.9K) is in the second lane. This pellet was resuspended and analyzed on a sucrose step gradient at 0%, 40% and 50% sucrose. The pellet of the gradient, which contains the nuclei (NP), and the interphases are analyzed as indicated in the last three lanes. The supernatant of the initial low spin was centrifuged at 40,000×g and the pellet was analyzed in the lane indicated as 40K. Finally the supernatant of the 40K spin was centrifuged again at 100,000×g (lanes indicated as 100K) and the resulting pellet (P) and supernatant (S) were loaded on the gel.

Figure 5:
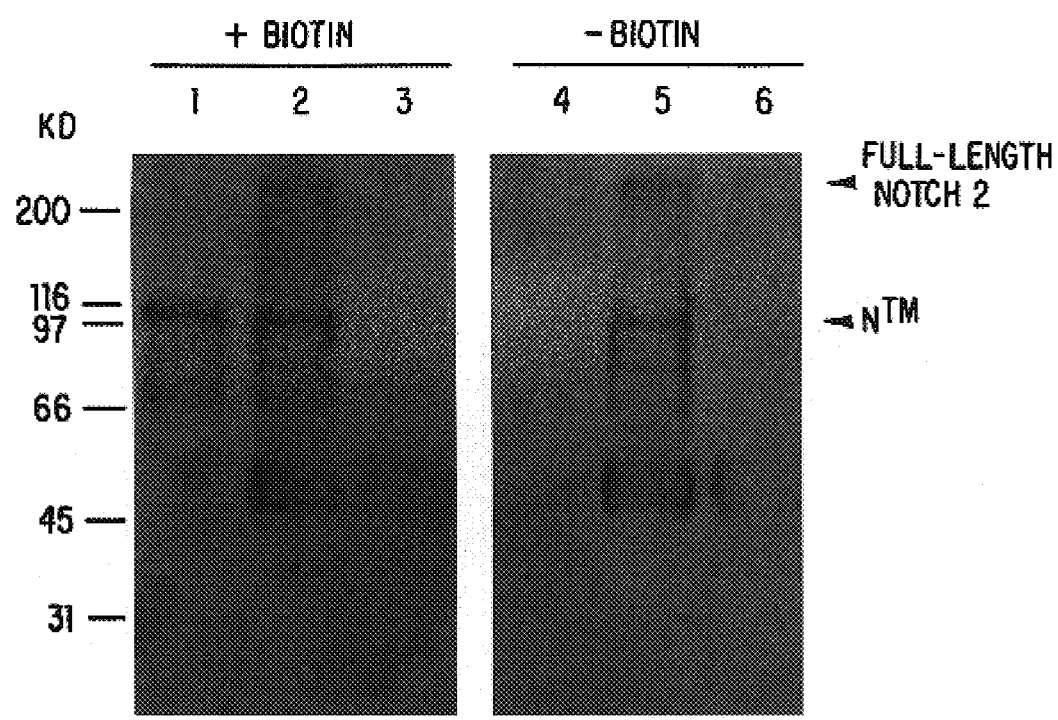

FIG. 5 shows that the 110 kDa ($N^{TM}$) fragment is expressed on the cell surface. SJ-NB5 cells were treated with biotin (+Biotin) while control cells were not (−Biotin). Each sample was lysed and divided into three equal portions precipitated with immobilized streptavidin, anti-Notch2 antibody PGHN (lanes 1, 2 and 3) or normal rabbit serum (lanes 4, 5 and 6). Samples were run on a 4–20% SDS-PAGE gel and blotted with antibody bhN6D. Molecular weight markers are shown on the left. $N^{TM}$ accumulates on the surface, while full-length Notch is not precipitated by streptavidin.

Figure 6A:
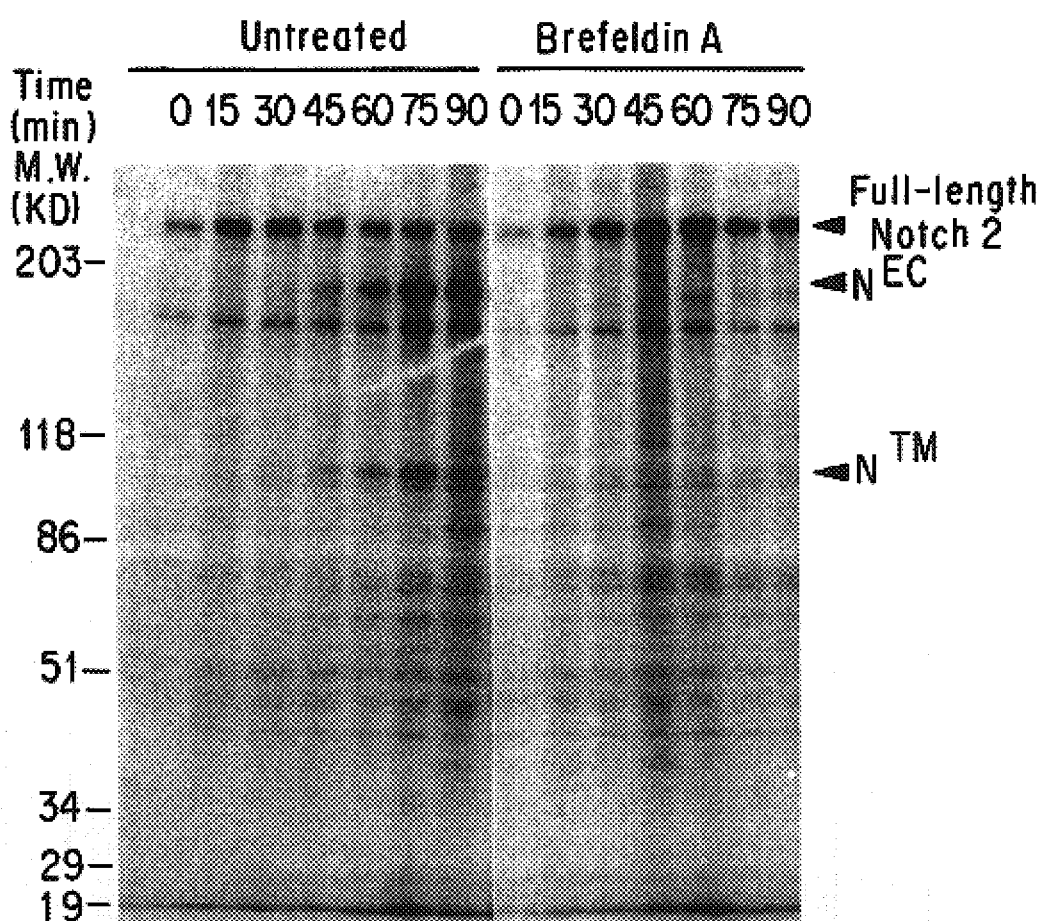
Figure 6B:
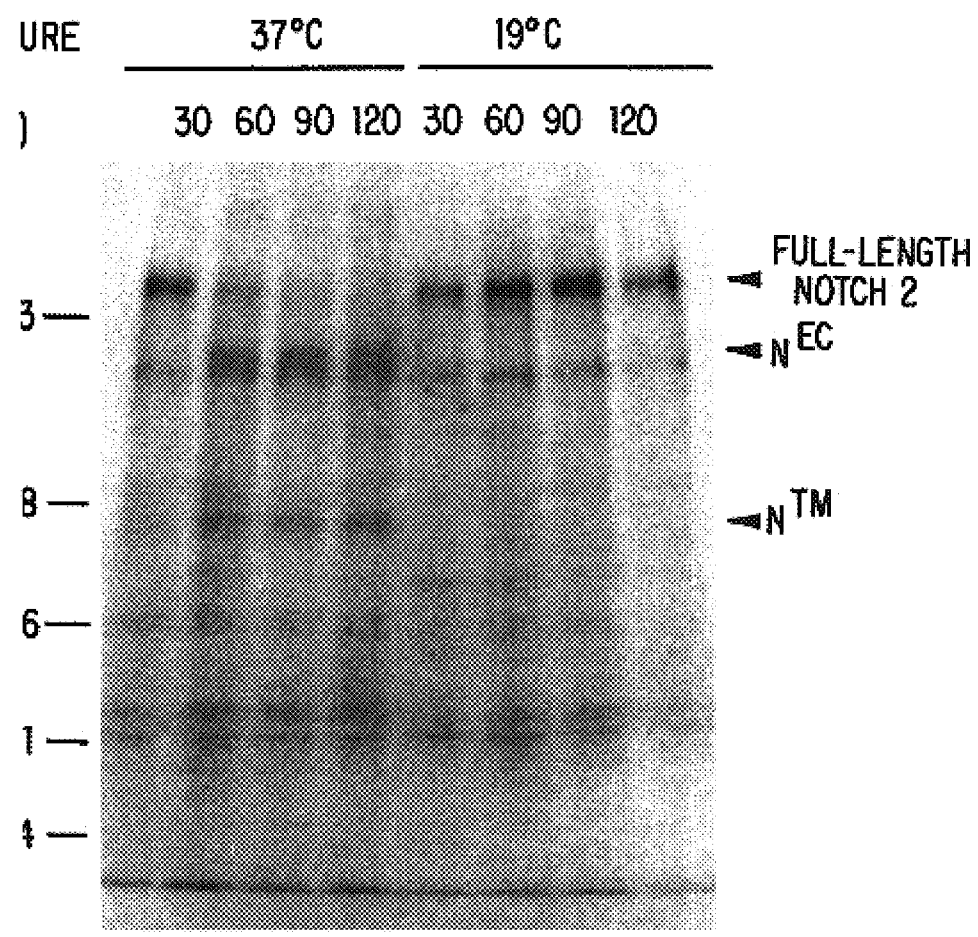

FIGS. 6A–6B show that the processing of Notch2 is blocked by Brefeldin A and at 19° C. FIG. 6A shows the results of a pulse labeling experiment in SJ-NB5 cells in the presence or absence of Brefeldin A. [$^{35}$S]-Methionine was allowed to incorporate for 20 minutes and then chased for 0, 15, 30, 45, 60, 90 minutes at 37° C. The cell lysates were immunoprecipitated by PGHN (a polyclonal antibody raised against intracellular Notch2 epitopes, Zagouras et al., 1995, Proc. Natl. Acad. Sci. USA 92:6414–6418), analyzed by SDS-PAGE and followed by fluorography. FIG. 6B shows SJ-NB5 cells labeled with [$^{35}$S]-methionine for 20 minutes, chased either at 37° C. or 19° C. for 0, 30, 60, 90 minutes, immunoprecipitated by PGHN and analyzed by SDS-PAGE, followed by fluorography. Two fragments accumulate during the chase and co-immunoprecipitate with PGHN: a 180 kDa fragment ($N^{EC}$) and a 110 kDa fragment ($N^{TM}$).

Figure 7:
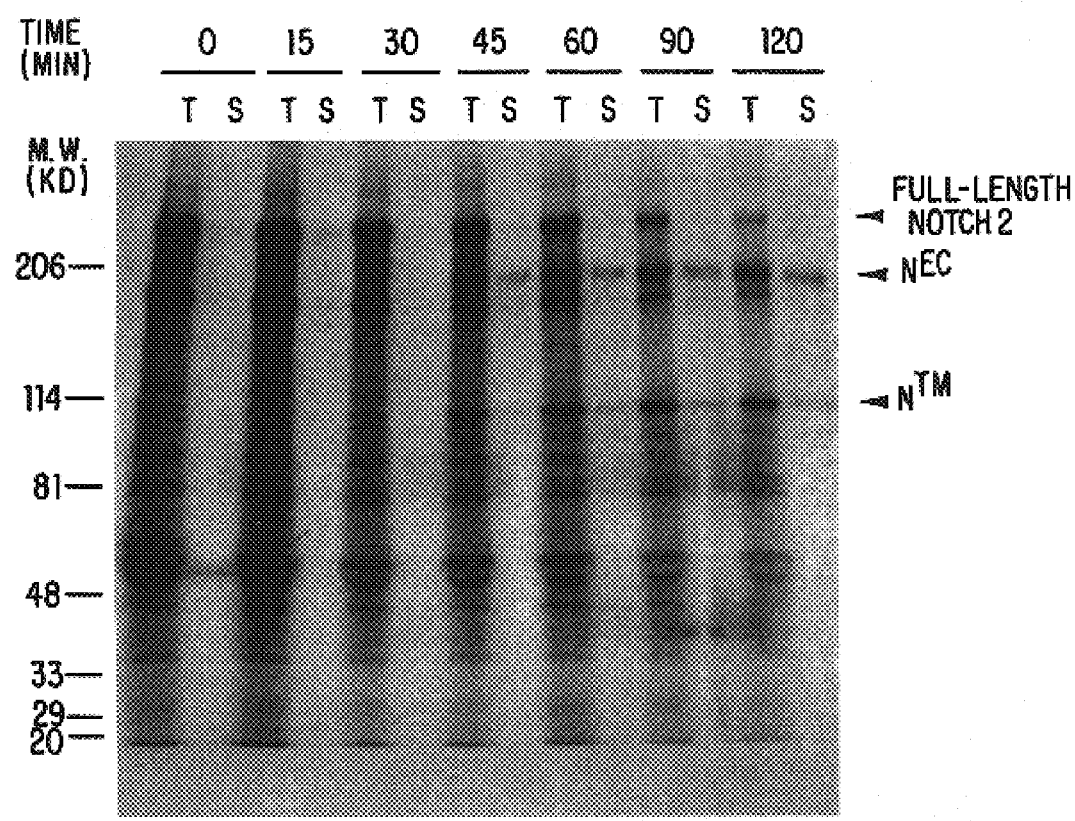

FIG. 7 shows that full-length Notch does not accumulate on the cell surface. SJ-NB5 cells were pulse labeled with [$^{35}$S]-methionine for 10 minutes, chased for 0, 15, 30, 45, 60, 90 and 120 minutes, and this was followed by the biotinylation of the surface proteins. The cell lysates were immunoprecipitated with the polyclonal Notch2 antibody PGHN (Zagouras et al., 1995, Proc. Natl. Acad. Sci. USA 92:6414–6418). Lanes corresponding to those lysates are designated T and show all the antigens recognized by PGHN. At each time point, part of the PGHN immunoprecipitate was resuspended and then immunoprecipitated by streptavidin, which would correspond to the Notch antigens on the surface (S lanes). The immunoprecipitation products were analyzed by SDS-PAGE followed by fluorography. The accumulation of the $N^{TM}$ and $N^{EC}$ fragments is evident, while full-length Notch is not detected on the surface.

Figure 8:
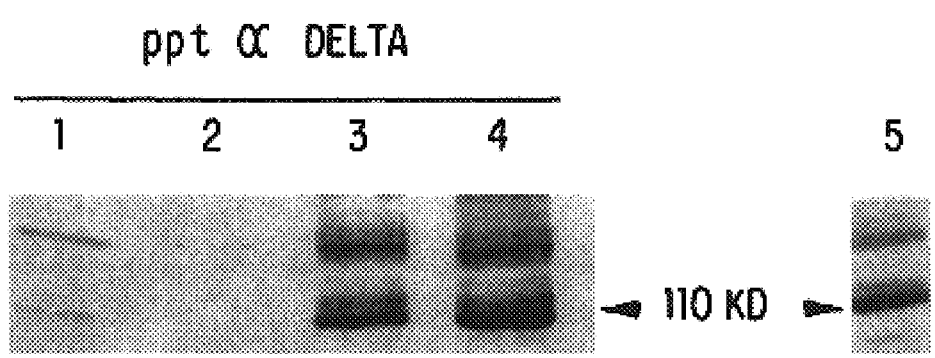

FIG. 8 shows that Delta binds to the heterodimeric form of Notch. Identical amounts of cell lysates were precipitated with Delta antibodies from S2 cells expressing Notch (lane 1), S2 cells expressing Delta (lane 2), Notch and Delta expressing cells after one hour of aggregation (lane 3) and Notch and Delta expressing cells after two hours of aggregation (lane 4). In addition, a cell lysate of Notch expressing cells which had not been incubated with Delta antibody is shown in lane 5. All lanes are visualized with Notch antibody 9C6, which recognizes intracellular epitopes. The 110 kd Notch $N^{TM}$ fragment is immunoprecipitated by the Delta antibodies in the extracts from Notch/Delta cell aggregates.

Figure 9:
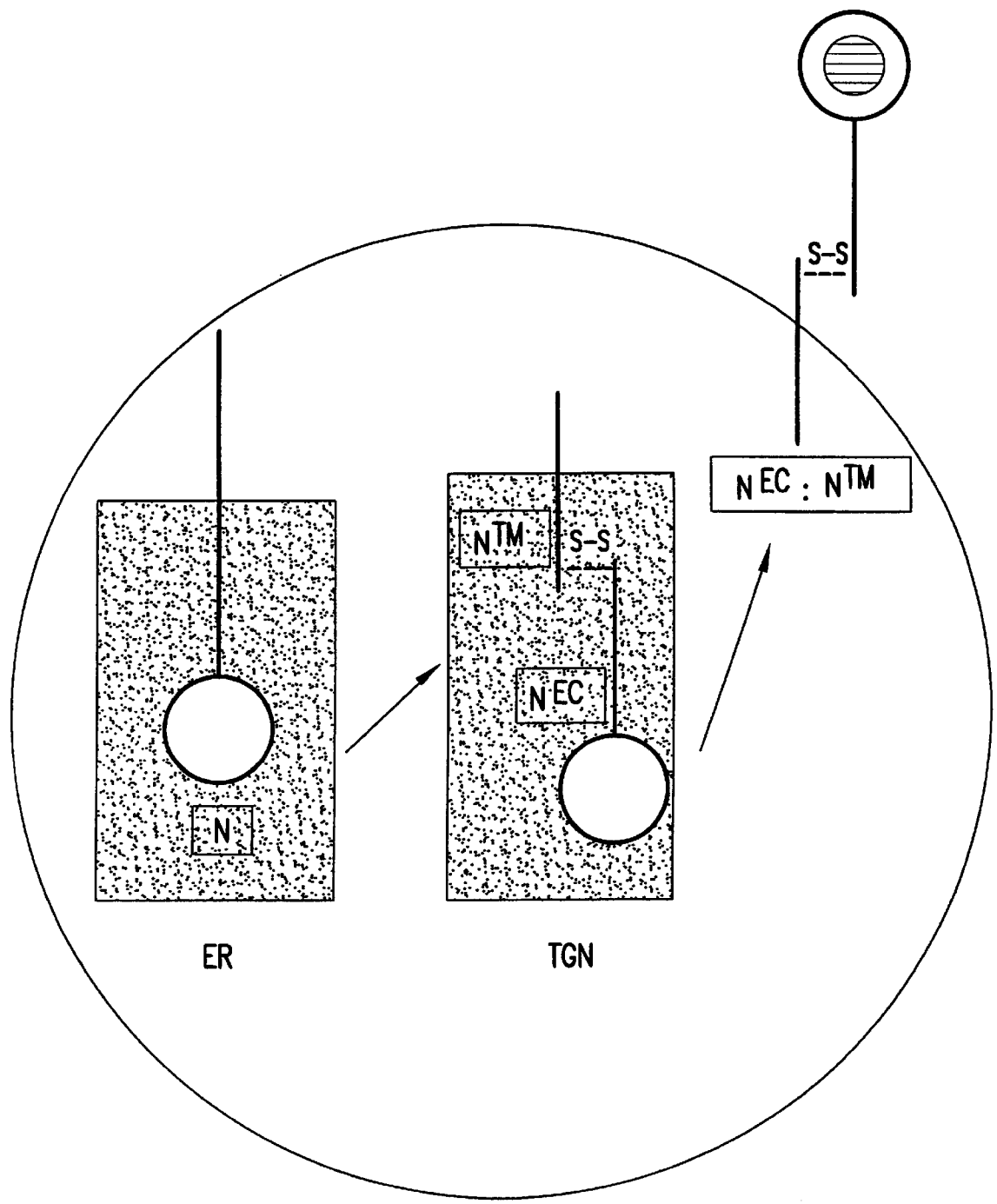

FIG. 9 is a model for the trafficking of the Notch receptor. Full-length Notch is synthesized in the ER (N) and then cleaved in the trans-Golgi network (TGN) extracellular region, producing two fragments, $N^{TM}$ and $N^{EC}$. Full-length Notch (N) reflects an inactive, presumably newly synthesized form of the receptor, which is not seen on the surface. $N^{TM}$ and $N^{EC}$, produced by a cleavage in the extracellular domain, are tethered together on the surface via a DTT-sensitive link, constituting the active form of the receptor that can interact with ligands (horizontally lined circle) and/or interact homotypically with another Notch receptor or conceivably with other surface molecules.

Figure 10A:
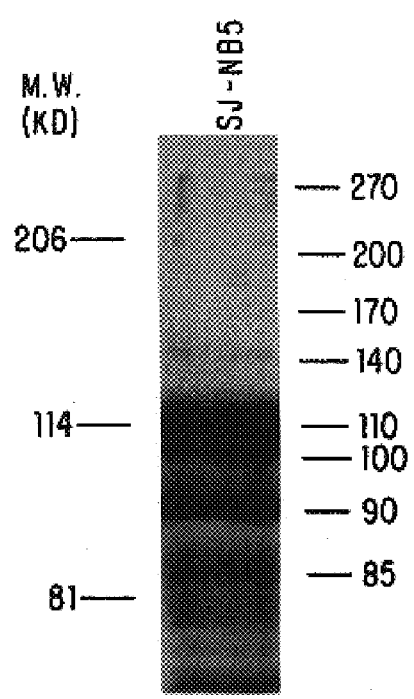
Figure 10B:
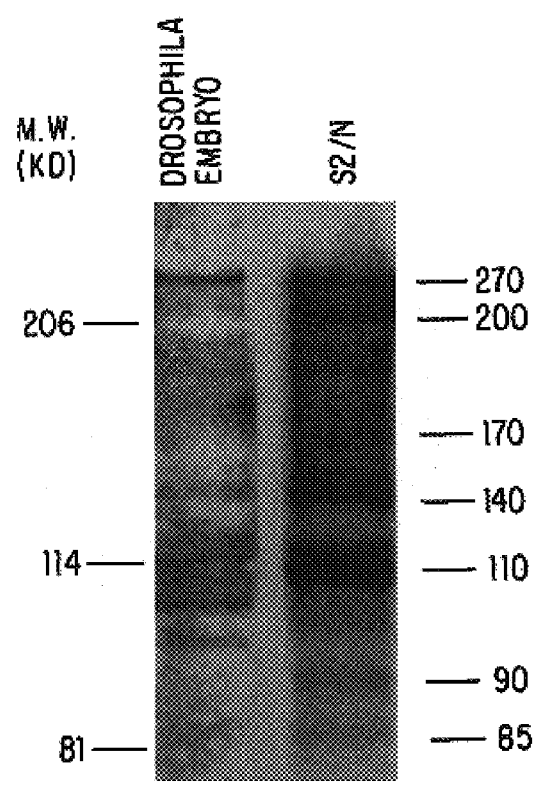

FIGS. 10A–10B are Western blot analyses showing the Notch cleavage pattern in human cells, in Drosophila embryo extracts and in Drosophila S2 cells which recombinantly express Notch. FIG. 10A is a Western blot of SJ-NB5 cells (human neuroblastoma) using antibody bhN6D and FIG. 10B is a Western blot of Drosophila embryo extracts and in Drosophila S2 cells which recombinantly express Notch using antibody 9C6. Molecular weight markers are indicated at left for both FIGS. 10A and 10B.

FIGS. 11A–11B show that $N^{EC}$ and $N^{TM}$ are associated in a non-covalent manner. FIG. 11A is a Western blot analysis demonstrating that $N^{EC}$ is present in the supernatant of Notch expressing S2 cells that have been resuspended in 2 mM EDTA, Tris-HCl saline buffer (EDTA), whereas in the presence of 2 mM $CaCl_2$ ($Ca^{2+}$) insignificant amounts of $N^{EC}$ are detected. FIG. 11B is a Western blot of a sucrose density centrifugation of S2 cell extracts that shows $N^{EC}$ and $N^{TM}$ co-sediment in the presence of $CaCl_2$, whereas $N^{EC}$ and $N^{TM}$ sediment separately in the presence of EDTA.

5. DETAILED DESCRIPTION OF THE INVENTION

The present invention is directed to methods for detecting or measuring Notch activation by observing or measuring the appearance of Notch on the cell surface or by observing or measuring Notch cleavage products, that are indicative of Notch activation. In one aspect of this embodiment of the invention, the method for detecting or measuring Notch activation in a cell comprises detecting or measuring the expression of Notch on the surface of said cell, wherein the presence and amount of Notch on the surface indicates the presence and amount, respectively, of Notch activation. In another aspect, the method comprises detecting or measuring the expression of one or more Notch cleavage products selected from the group consisting of $N^{EC}$ and $N^{TM}$. In yet another aspect, the method comprises detecting or measuring one or more fragments of Notch selected from the group consisting of an amino-terminal fragment of full-length Notch terminating between the epidermal growth factor-like repeat domain and the transmembrane domain (in particular, between the Lin-12/Notch repeats and the transmembrane domain) of full-length Notch, and a carboxy-terminal fragment of full-length Notch with its amino terminus situated between the epidermal growth factor-like repeat domain and the transmembrane domain (in particular, between the Lin-12/Notch repeats and the transmembrane domain), or detecting or measuring one or more fragments of Notch selected from the group consisting of Notch fragments having a molecular weight of about 270, 200, 170, 140, 110, 100, 90 and 85 kilodaltons. In yet another aspect, the method comprises detecting or measuring a Notch heterodimer containing a reducing agent-sensitive linkage, in particular, a non-covalent, metal ion-dependent (e.g., calcium ion-dependent) linkage.

The present invention is based, at least in part, on the discovery that Notch in its active form, i.e., the form that mediates signal transduction and that binds Notch ligands such as Delta, is a heterodimer of two Notch cleavage products, an about (±10%) 180 kilodaltons (kDa) subunit ($N^{EC}$) and an about (±10%) 110 kDa subunit ($N^{TM}$), which are tethered together through a reducing agent-sensitive linkage, in particular, a non-covalent, metal ion-dependent (e.g., calcium ion-dependent) linkage. Full length Notch is not expressed on the cell surface and is ligand inaccessible. As shown by way of example infra, the two subunits arise due to a proteolytic cleavage of the full length Notch molecule in the trans-Golgi at a site in Notch amino-terminal to the transmembrane domain and carboxy-terminal to the EGF repeat region, thus generating an extracellular fragment ($N^{EC}$) of about 180 kDa and a transmembrane/intracellular fragment ($N^{TM}$) of about 110 kDa. The detection of full length Notch and of Notch cleavage products, as well as Notch that is present on the cell surface, can be carried out by methods well known to those of skill in the art, e.g., precipitation or binding to an immobilized binding partner (e.g., on a plate or column), e.g., anti-Notch antibodies or ligands of Notch, such as Delta and Serrate.

Logeat et al., 1998, Proc. Natl. Acad. Sci. USA 95:8108–8112, demonstrated that the convertase furin cleaves human Notch1 on the carboxy side of the sequence ArgGlnArgArg (amino acids 1651–1654), which is in the region between the Lin-12/Notch repeats and the transmembrane domain. Although human Notch2, as well as mouse Notch (mNotch), do not have sequence identity at this region with human Notch1, we believe the cleavage site in these proteins likely to be between the epidermal growth factor-like repeats and the transmembrane domain, e.g., between the Lin-12/Notch repeats and the transmembrane domain.

The detection or measurement of Notch activation is important in the study and manipulation of differentiation processes, since Notch plays a key role in cell fate (differentiation) determination. Also, disorders of cell fate, in particular hyperproliferative (e.g., cancer) or hypoproliferative disorders, involving aberrant or undesirable levels of active Notch expression can be diagnosed or screened for by detecting such active Notch expression, as described more fully infra. Molecules that modulate Notch function are important tools for studying and manipulating differentiation processes, e.g., in expanding cell populations without substantial differentiation (International Publication WO 97/11716), in cancer studies and therapy (International Publication WO 94/07474), and differentiation studies on normal tissue.

In another embodiment, the present invention is also directed to methods for identifying a molecule that modulates Notch activation by detecting or measuring a change in the amount of Notch expressed on the cell surface or a change in the amount or pattern of Notch cleavage products. In one aspect of this embodiment of the invention, the method for identifying a modulator of Notch activation comprises providing a cell with a candidate modulator molecule and detecting or measuring the amount of Notch on the surface of the cell, in which a difference in the presence or amount compared to a cell not contacted with the candidate molecule indicates that the candidate molecule modulates Notch activation. In another aspect, the method for identifying a modulator of Notch activation comprises providing a cell with a candidate modulator molecule and detecting or measuring the expression by the cell of one or more Notch cleavage products selected from the group consisting of $N^{EC}$ and $N^{TM}$, in which a difference in the presence or amount of said one or more cleavage products compared to a Notch cell not contacted with the candidate molecule indicates that the molecule modulates Notch activity.

In an alternative aspect, the method for identifying a modulator of Notch activation comprises contacting a candidate modulator molecule with a full length Notch in the presence of a composition comprising cellular proteins, under conditions conducive to cleavage of the full-length Notch by one or more components of the composition and detecting or measuring the amount of Notch cleavage products $N^{EC}$ and $N^{TM}$ that result, in which a difference in the presence or amount of said Notch cleavage products compared to a full-length Notch in presence of said composition not contacted with the candidate molecule indicates that the molecule modulates Notch activity.

The present invention is also directed to a substantially purified active form of Notch which comprises Notch fragments tethered together through a reducing agent-sensitive linkage, in particular, a non-covalent, metal ion-dependent (e.g., calcium ion-dependent) linkage, and pharmaceutical compositions and kits thereof.

For clarity of disclosure, and not by way of limitation, the detailed description of the invention is divided into subsections, as follows.

5.1 Detection of the Active Form of Notch

In this embodiment of the invention, methods are provided for the detection or measuring of Notch activation comprising detecting or measuring the expression of Notch on the surface of said cell, wherein the presence and amount of Notch on the surface indicates the presence and amount, respectively, of Notch activation, or detecting or measuring the expression of one or more Notch cleavage products selected from the group consisting of $N^{EC}$ and $N^{TM}$, or detecting or measuring one or more fragments of Notch selected from the group consisting of an amino-terminal fragment of full-length Notch terminating between the epidermal growth factor-like repeat domain and the transmembrane domain (in particular, between the Lin-12/Notch repeats and the transmembrane domain) of full-length Notch repeats of full-length Notch, and a carboxy-terminal fragment with its amino terminus situated between the epidermal growth factor-like repeat domain and the transmembrane domain (in particular, between the Lin-12/Notch repeats and the transmembrane domain), or detecting or measuring one or more fragments of Notch selected from the group consisting of Notch fragments having a molecular weight of about 270, 200, 170, 140, 110, 100, 90 and 85 kilodaltons, or detecting or measuring a Notch heterodimer containing a reducing agent-sensitive linkage (particularly, a non-covalent, metal ion-dependent (e.g., calcium ion-dependent) linkage), or detecting or measuring a pattern of Notch fragments such as shown in FIG. 10A or 10B (with approximate molecular weights indicated on the right side of each figure). The assay methods of the invention are preferably carried out in vitro or in cell culture, but alternatively, may be carried out in vivo in an animal.

The invention is based, at least in part, on the discovery that the active form of Notch is not the full length form but rather a cell surface expressed heterodimer consisting of $N^{EC}$ and $N^{TM}$ Notch fragments tethered together through a reducing agent-sensitive linkage, in particular, a non-covalent, metal ion-dependent, (e.g., calcium ion-dependent) linkage.

In an alternative embodiment, methods are provided for the detecting or measuring of Notch activation comprising detecting or measuring the levels of $N^{EC}$ in cell culture medium in the presence of an amount of a divalent metal ion chelator such as but not limited to EDTA or EGTA sufficient to cause dissociation of Notch surface heterodimers, wherein the presence and amount of Notch in the culture medium indicates the presence and amount, respectively, of Notch activation.

The ability to detect the expression of the active form of Notch is an important diagnostic/screening tool for cancer since Notch is known to be aberrantly expressed in neoplasias. For example, the aberrant expression of a truncated Notch1 RNA is seen in a human T cell leukemia (Ellison et al., 1991, Cell 66:649–661). Further, human Notch1 and Notch2 are not normally expressed in columnar epithelia but are expressed in neoplasias, in cases ranging from relatively benign squamous metaplasias to cancerous invasive adenocarcinomas in which columnar epithelia are replaced by these tumors (Mello et al., 1994, Cell 77:95–106; see also International Publication WO 94/07474). Therefore, using the assay methods of the present invention, aberrant forms or levels of Notch activation, which may be present in various malignancies, can be detected.

Any method known in the art for detecting or measuring the expression of Notch on the cell surface or the expression of Notch cleavage products indicative of Notch activation can be used. For example, and not by way of limitation, one such method of detection of the active form of Notch by detecting cell surface expression of Notch is by labeling generally the cell surface-expressed proteins with, e.g., biotin or $^{125}I$, and then detecting the label on Notch. If no label is detected, Notch is not expressed on the cell surface, and thus the active form of Notch is not expressed. Another method of detection of the active form of Notch is, e.g., by labeling generally the cell surface-expressed proteins, with, e.g., biotin or $^{125}I$, adding a sufficient amount of a divalent metal ion chelator to disrupt the interaction between $N^{EC}$ and $N^{TM}$, and then detecting the label in the cell culture medium. If no label is detected, the active form of Notch is not expressed. In a specific embodiment, Notch can be isolated using, e.g., an anti-Notch antibody or Notch ligand or a binding fragment of a Notch ligand, before detecting the label on Notch. A particular method of detecting cell surface Notch is to contact a labelled anti-Notch antibody, e.g., labeled with a fluorescent dye or with a radioactive isotope such as $^{125}I$, to whole cells and then to detect cells having the label through, e.g., flow cytometry, fluorescent activated cell sorting (FACS) analysis, or scintillation counting.

Another method is to detect the active form of Notch by detecting one or more Notch cleavage products selected from the group consisting of $N^{EC}$ and $N^{TM}$, or selected from the group consisting of an amino-terminal fragment of full-length Notch terminating between the epidermal growth factor-like repeat domain and the transmembrane domain (in particular, between the Lin-12/Notch repeats and the transmembrane domain) of full-length Notch, and a carboxy-terminal fragment of full-length Notch with its amino terminus situated between the epidermal growth factor-like repeat domain and the transmembrane domain (in particular, between the Lin-12/Notch repeats and the transmembrane domain), or selected from the group consisting of Notch fragments having a molecular weight of about 270, 200, 170, 140, 110, 100, 90 and 85 kilodaltons. Yet another method is to detect a pattern of Notch cleavage products as shown in FIG. 10A or 10B.

Detection of such cleavage products can be done, e.g., by immunoprecipitating the cleavage products with an anti-Notch antibody or binding to anti-Notch antibody on an immunoaffinity column or immobilized on a plate or in a well, or visualizing the fragments by Western blotting. In a specific embodiment, the cleavage products can be labelled by general cell surface labeling, or, alternatively, by pulse labeling the cells by incubation in culture medium containing a radioactive label, or, alternatively, it can be anti-Notch antibody (or antibody binding partner) that is labeled rather than the Notch cleavage products.

According to a specific embodiment of the invention, antibodies and fragments containing the binding domain thereof, directed against Notch are used to detect. Notch in a specific embodiment of the above methods. Accordingly, Notch proteins, fragments or analogs or derivatives thereof, in particular, human Notch proteins or fragments thereof, may be used as immunogens to generate anti-Notch protein antibodies. Such antibodies can be polyclonal, monoclonal, chimeric, single chain, Fab fragments, or from an Fab expression library. In a specific embodiment, antibodies specific to EGF-like repeats 11 and 12 of Notch may be prepared. In other embodiments, antibodies reactive with the extracellular domain of Notch can be generated. In one embodiment, antibodies specific to human Notch are produced.

Various procedures known in the art may be used for the production of polyclonal antibodies to a Notch protein or peptide. In a particular embodiment, rabbit polyclonal antibodies to an epitope of the human Notch proteins depicted in FIGS. 2A–2D, or a subsequence thereof, can be obtained. For the production of antibody, various host animals can be immunized by injection with the native Notch protein, or a synthetic version, or fragment thereof, including but not limited to rabbits, mice, rats, etc. Various adjuvants may be used to increase the immunological response, depending on the host species, and including but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *corynebacterium parvum*.

For preparation of monoclonal antibodies directed toward a Notch protein sequence, any technique which provides for the production of antibody molecules by continuous cell lines in culture may be used. For example, the hybridoma technique originally developed by Kohler and Milstein (1975, Nature 256:495–497), as well as the trioma technique, the human B-cell hybridoma technique (Kozbor et al., 1983, Immunology Today 4:72), and the EBV-hybridoma technique to produce human monoclonal antibodies (Cole et al., 1985, in Monoclonal Antibodies and Cancer Therapy, Alan R. Liss, Inc., pp. 77–96).

Antibody fragments which contain the idiotype (binding domain) of the molecule can be generated by known techniques. For example, such fragments include but are not limited to: the $F(ab')_2$ fragment which can be produced by pepsin digestion of the antibody molecule; the Fab' fragments which can be generated by reducing the disulfide bridges of the $F(ab')_2$ fragment, and the Fab fragments which can be generated by treating the antibody molecule with papain and a reducing agent.

In the production of antibodies, screening for the desired antibody can be accomplished by techniques known in the art, e.g., ELISA (enzyme-linked immunosorbent assay). For example, to select antibodies which recognize the adhesive domain of a Notch protein, one may assay generated hybridomas for a product which binds to a protein fragment containing such domain. For selection of an antibody specific to human Notch, one can select on the basis of positive binding to human Notch and a lack of binding to Drosophila Notch.

Another method to detect the active form of Notch is to use a Notch ligand or other Notch binding partner or binding fragment thereof, such as Delta or Serrate and members of the Delta/Serrate family, to bind to Notch (e.g., when the ligand is labeled), or to recover Notch by coimmunoprecipitating with the appropriate anti-Notch ligand antibody to co-immunoprecipitate Notch cleavage products in the active Notch heterodimer bound to the Notch ligand, etc. Other Notch binding proteins, in addition to extracellular ligands, can also be used to co-immunoprecipitate Notch cleavage fragments. Examples of Notch ligands include but are not limited to Delta, Serrate, Deltex, and fragments and derivatives thereof that mediate binding to Notch; see e.g., International Publications WO 92/19734, WO 96/27610, WO 97/01571, and WO 97/18822.

Similar procedures to those described supra can be used to make antibodies to domains of other proteins (particularly toporythmic proteins) that bind or otherwise interact with Notch (e.g., binding fragments of Delta or Serrate).

Another method that can be used to detect the cell surface-expressed active form of Notch is to assay for cell adhesion between cells expressing Notch and cells expressing a Notch ligand, such as Delta or Serrate or members of the Delta/Serrate family, e.g., according to the method disclosed in Rebay et al., 1991, Cell 67:687–699 and International Publication WO 92/19734. In one aspect, this method comprises contacting a first plurality of said cell with a second plurality of cells expressing a Notch ligand on their surfaces; and measuring cell aggregation between cells in said first plurality and cells in second plurality.

The cell in which Notch activation is detected or measured can be any cell, e.g., one that endogenously or recombinantly expresses Notch. The cell can be vertebrate, insect (e.g., Drosophila), *C. elegans*, mammalian, bovine, murine, rat, avian, fish, primate, human, etc. The Notch which is expressed can be vertebrate, insect, *C. elegans*, mammalian, bovine, murine, rat, avian, fish, primate, human, etc. The cell can be a cell of primary tissue, a cell line, or of an animal containing and expressing a Notch transgene. For example, the transgenic animal can be a Drosophila (e.g., melanogaster) or a *C. elegans*. In a preferred embodiment, the transgene encodes a human Notch. Transgenic animals can be made by standard methods well known in the art (e.g., by use of P element transposons as a vector in Drosophila).

5.2 Methods of Identifying Modulators

In one embodiment of the invention, methods are provided for the identification of modulators, e.g., inhibitors, antagonists, or agonists, of Notch activation by detecting the ability of the modulators to effect cleavage of full length Notch and/or its expression on the cell surface. The invention is based, at least in part, on the discovery that the active form of Notch is not the full length protein but rather a cell surface-expressed heterodimer consisting of $N^{EC}$ and $N^{TM}$ Notch fragments (Notch cleavage products) tethered together through a reducing agent-sensitive linkage, in particular, a non-covalent, metal-ion-dependent (e.g., calcium ion-dependent) linkage. In one aspect of this embodiment of the invention, the method for identifying a modulator of Notch activation comprises providing a cell with a candidate modulator molecule and detecting or measuring the amount of Notch on the surface of the cell, in which a difference in the presence or amount compared to a cell not contacted with the candidate molecule indicates that the candidate molecule modulates Notch activation. In another aspect of this embodiment of the invention, the method comprises providing a cell with a candidate modulator molecule and detecting or measuring the expression by the cell of one or more Notch cleavage products selected from the group consisting of $N^{EC}$ and $N^{TM}$, in which a difference in the presence or amount of said one or more cleavage products compared to a Notch cell not contacted with the candidate molecule indicates that the molecule modulates Notch activity. In yet another aspect, the method comprises providing a cell with a candidate modulator molecule and detecting or measuring the amount of the expression by the cell of one or more fragments of Notch selected from the group consisting of an amino-terminal fragment of full-length Notch terminating between the epidermal growth factor-like repeat domain and the transmembrane domain (in particular, between the Lin-12/Notch repeats and the transmembrane domain) of full-length Notch, and a carboxy-terminal fragment of full-length Notch with its amino terminus situated between the epidermal growth factor-like repeat domain and the transmembrane domain (in particular, between the Lin-12/Notch repeats and the transmembrane domain); in which a difference in the presence or amount of said one or more fragments compared to a Notch cell not.contacted with the candidate molecule indicates that the molecule modulates Notch activity.

In yet another aspect, the method comprises providing a cell with a candidate modulator molecule and detecting or measuring the expression by the cell of one or more fragments of Notch selected from the group consisting of Notch fragments having a molecular weight of about 270, 200, 170, 140, 110, 100, 90 and 85 kilodaltons, in which a difference in the presence or amount of said one or more fragments compared to a Notch cell not contacted with the candidate molecule indicates that the molecule modulates Notch activity. In another aspect, the method comprises providing a cell with a candidate modulator molecule and detecting or measuring the amount of the expression by the cell of a pattern of Notch cleavage products as shown in FIG. 10A or 10B, in which a difference in the presence or amount of said pattern compared to a Notch cell not contacted with the candidate molecule indicates that the molecule modulates Notch activity. In yet another aspect, the method comprises providing a cell with a candidate modulator molecule and detecting or measuring the amount of the expression by the cell of one or more Notch fragments of about 180 kilodaltons and about 110 kilodaltons, respectively, in which a difference in the presence or amount of the fragments compared to a Notch cell not contacted with the candidate molecule indicates that the molecule modulates Notch activity. In another aspect, the method for identifying a modulator of Notch activation comprises contacting a cell with a candidate modulator molecule and detecting or measuring the amount of the expression by the cell of a Notch heterodimer containing a reducing agent-sensitive linkage, in a preferred aspect, a non-covalent, metal ion-dependent (e.g., calcium ion-dependent) linkage, in which a difference in the presence or amount of the heterodimer compared to a Notch cell not contacted with the candidate molecule indicates that the molecule modulates Notch activity. In a specific aspect of this embodiment of the invention, the detecting or measuring is carried out by contacting a first plurality of said cell with a second plurality of cells expressing a Notch ligand on their surfaces; and measuring cell aggregation between cells in said first plurality and cells in second plurality.

In yet another aspect of this embodiment of the invention, the method for identifying a modulator of Notch activation comprises contacting a candidate modulator molecule with a full length Notch in the presence of a composition comprising cellular proteins, under conditions conducive to cleavage of the full-length Notch by one or more components of the composition, and detecting or measuring the amount of Notch cleavage products $N^{EC}$ and/or $N^{TM}$ that result, in which a difference in the presence or amount of said Notch cleavage product(s) compared to a full-length Notch in presence of said composition not contacted with the candidate molecule indicates that the molecule modulates Notch activity. In another aspect, the method for identifying a modulator of Notch activation comprises contacting a candidate modulator molecule with a full length Notch in the presence of a composition comprising cellular proteins, under conditions conducive to cleavage of the full-length Notch by one or more components of the composition, and detecting or measuring one or more fragments of Notch selected from the group consisting of an amino-terminal fragment of full-length Notch terminating between the epidermal growth factor-like repeat domain and the transmembrane domain (in particular, between the Lin-12/Notch repeats and the transmembrane domain) of full-length Notch, and a carboxy-terminal fragment of full-length Notch with its amino terminus situated between the epidermal growth factor-like repeat domain and the transmembrane domain (in particular, between the Lin-12/Notch repeats and the transmembrane domain), that result, in which a difference in the presence or amount of said one or more Notch fragments compared to a full-length Notch in presence of said composition not contacted with the candidate molecule indicates that the molecule modulates Notch activity.

In yet another aspect, the method for identifying a modulator of Notch activation comprises contacting a candidate modulator molecule with a full length Notch in the presence of a composition comprising cellular proteins, under conditions conducive to cleavage of the full-length Notch by one or more components of the composition and detecting or measuring the amount of one or more fragments of Notch selected from the group consisting of Notch fragments having a molecular weight of about 270, 200, 170, 140, 110, 100, 90 and 85 kilodaltons, that result, in which a difference in the presence or amount of said one or more Notch fragments compared to a full-length Notch in presence of said composition not contacted with the candidate molecule indicates that the molecule modulates Notch activity. In yet another aspect, the method for identifying a modulator of Notch activation comprises contacting a candidate modulator molecule with a full length Notch in the presence of a composition comprising cellular proteins, under conditions conducive to cleavage of the full-length Notch by one or more components of the composition, and detecting or measuring the amount of a pattern of Notch cleavage products as shown in FIG. 10A or 10B that result, in which a difference in the presence or amount of said pattern compared to a full-length Notch in presence of said composition not contacted with the candidate molecule indicates that the molecule modulates Notch activity.

In yet another aspect of this embodiment of the invention, the method for identifying a modulator of Notch activation comprises contacting a candidate modulator molecule with a full length Notch in the presence of a composition comprising cellular proteins, under conditions conducive to cleavage of the full-length Notch by one or more components of the composition, and detecting or measuring the amount of one or more Notch fragments of about 180 kilodaltons and about 110 kilodaltons, respectively, that result, in which a difference in the presence or amount of said one or more Notch fragments compared to-a full-length Notch in presence of said composition not contacted with the candidate molecule indicates that the molecule modulates Notch activity. In yet another aspect, the method for identifying a modulator of Notch activation comprises contacting a candidate modulator molecule with a full length Notch in the presence of a composition comprising cellular proteins, under conditions conducive to cleavage of the full-length Notch by one or more components of the composition, and detecting or measuring the amount of a Notch heterodimer containing a reducing agent-sensitive linkage, in particular, a non-covalent, metal ion-dependent (e.g., calcium ion-dependent) linkage, that results, in which a difference in the presence or amount of said heterodimer compared to a full-length Notch in presence of said composition not contacted with the candidate molecule indicates that the molecule modulates Notch activity.

In a specific aspect of the embodiment using a composition comprising cellular proteins, the composition comprising cellular proteins is a cell lysate made from cells which recombinantly express Notch. In another specific aspect of this embodiment, the composition comprising cellular proteins is a cell lysate made from cells which endogenously express Notch.

Detection or measurement of Notch expressed on the cell surface and/or Notch cleavage products can be carried out by methods well known in the art and/or those methods disclosed in Section 5.1, supra.

The cells used in the methods of this embodiment can either endogenously or recombinantly express Notch. Examples of the cell types and Notch protein that can be expressed are described in Section 5.1. Recombinant Notch expression is carried out by introducing Notch encoding nucleic acids into expression vectors and subsequently introducing the vectors into a cell to express Notch or simply introducing Notch encoding nucleic acids into a cell for expression. Nucleic acids encoding vertebrate and non-vertebrate Notch have been cloned and sequenced and their expression is well known in the art. See, for example, International Publication WO 92/19734 and U.S. Pat. No. 5,648,464, which are incorporated by reference in their entirety herein; Wharton et al., 1985, Cell 43:567–581; and Coffman et al., 1990, Science 249:1438–1441. Expression can be from expression vectors or intrachromosomal.

Any method known to those of skill in the art for the insertion of Notch-encoding DNA into a vector may be used to construct expression vectors containing a chimeric gene consisting of appropriate transcriptional/translational control signals and the protein coding sequences. These methods may include in vitro recombinant DNA and synthetic techniques and in vivo recombinants (genetic recombination). Expression of nucleic acid sequence encoding a Notch protein may be regulated by a second nucleic acid sequence so that the Notch protein is expressed in a host transformed with the recombinant DNA molecule. For example, expression of a Notch protein may be controlled by any promoter/enhancer element known in the art. Promoters which may be used to control Notch gene expression include, but are not limited to, the SV40 early promoter region (Bernoist and Chambon, 1981, Nature 290:304–310), the promoter contained in the 3' long terminal repeat of Rous sarcoma virus (Yamamoto, et al., 1980, Cell:22 787–797), the herpes thymidine kinase promoter (Wagner et al., 1981, Proc. Natl. Acad. Sci. U.S.A. 78:1441–1445), the regulatory sequences of the metallothionein gene (Brinster et al., 1982, Nature 296:39–42); prokaryotic expression vectors such as the β-lactamase promoter (Villa-Kamaroff, et al., 1978, Proc. Natl. Acad. Sci. U.S.A. 75:3727–3731), or the tac promoter (DeBoer, et al., 1983, Proc. Natl. Acad. Sci. U.S.A. 80:21–25); see also "Useful proteins from recombinant bacteria" in Scientific American, 1980, 242:74–94; plant expression vectors comprising the nopaline synthetase promoter region (Herrera-Estrella et al., Nature 303:209–213) or the cauliflower mosaic virus 35S RNA promoter (Gardner, et al., 1981, Nucl. Acids Res. 9:2871), and the promoter of the photosynthetic enzyme ribulose biphosphate carboxylase (Herrera-Estrella et al., 1984, Nature 310:115–120); promoter elements from yeast or other fungi such as the Gal 4 promoter, the ADC (alcohol dehydrogenase) promoter, PGK (phosphoglycerol kinase) promoter, alkaline phosphatase promoter, and the following animal transcriptional control regions, which exhibit tissue specificity and have been utilized in transgenic animals: elastase I gene control region which is active in pancreatic acinar cells (Swift et al., 1984, Cell 38:639–646; Ornitz et al., 1986, Cold Spring Harbor Symp. Quant. Biol. 50:399–409; MacDonald, 1987, Hepatology 7:425–515); insulin gene control region which is active in pancreatic beta cells (Hanahan, 1985, Nature 315:115–122), immunoglobulin gene control region which is active in lymphoid cells (Grosschedl et al., 1984, Cell 38:647–658; Adames et al., 1985, Nature 318:533–538; Alexander et al., 1987, Mol. Cell. Biol. 7:1436–1444), mouse mammary tumor virus control region which is active in testicular, breast, lymphoid and mast cells (Leder et al., 1986, Cell 45:485–495), albumin gene control region which is active in liver (Pinkert et al., 1987, Genes and Devel. 1:268–276), alpha-fetoprotein gene control region which is active in liver (Krumlauf et al., 1985, Mol. Cell. Biol. 5:1639–1648; Hammer et al., 1987, Science 235:53–58; alpha 1-antitrypsin gene control region which is active in the liver (Kelsey et al., 1987, Genes and Devel. 1:161–171), beta-globin gene control region which is active in myeloid cells (Mogram et al., 1985, Nature 315:338–340; Kollias et al., 1986, Cell 46:89–94; myelin basic protein gene control region which is active in oligodendrocyte cells in the brain (Readhead et al., 1987, Cell 48:703–712); myosin light chain-2 gene control region which is active in skeletal muscle (Sani, 1985, Nature 314:283–286), and gonadotropic releasing hormone gene control region which is active in the hypothalamus (Mason et al., 1986, Science 234:1372–1378).

Many expression vectors can be used, including but not limited to, the following vectors or their derivatives: human or animal viruses such as vaccinia virus or adenovirus; insect viruses such as baculovirus; yeast vectors; bacteriophage vectors (e.g., lambda), and plasmid and cosmid DNA vectors, to name but a few.

In addition, a host cell strain may be chosen which modulates the expression of Notch, or modifies and processes the gene product in the specific fashion desired. Expression from certain promoters can be elevated in the presence of certain inducers; thus, expression of Notch protein may be controlled. Furthermore, different host cells have characteristic and specific mechanisms for the translational and post-translational processing and modification (e.g., glycosylation, cleavage) of proteins. Appropriate cell lines or host systems can be chosen to ensure the desired modification and processing of the Notch protein expressed. For example, expression in a bacterial system can be used to produce an unglycosylated core protein product. Expression in yeast will produce a glycosylated product. Expression in mammalian cells can be used to ensure "native" glycosylation of a mammalian Notch protein.

In the methods of the invention in which full-length Notch is incubated with compositions comprising cellular proteins (e.g., cell lysates or cell fractions) in the presence of candidate cleavage (and thus Notch activation) modulators the expression of Notch should be such that full length Notch is expressed and proteolytic cleavage of Notch is kept to a minimum such that Notch cleavage products are easily detected over any background proteolysis. There are several methods known in the art to keep proteolysis to a minimum. For example, one manner to keep Notch cleavage to a minimum is to express Notch in cells concurrently with Brefeldin A treatment. Brefeldin A has been shown to inhibit the cleavage of Notch, see Section 6.7, infra. Another manner to keep Notch cleavage to a minimum is to incubate Notch expressing cells at 19° C., see also Section 6.7, infra. Another manner is to express Notch in cells which do not contain a protease which cleaves Notch or to express Notch in an in vitro transcription-translation system in the presence of a protease inhibitor such as phenylmethylsulfonylfluoride (PMSF).

5.2.1 Candidate Molecules

Any molecule known in the art can be tested for its ability to modulate Notch activation as measured by the cell surface expression of Notch or the expression of one or more of the Notch cleavage products disclosed herein. For identifying a molecule that modulates Notch activation, candidate molecules can be directly provided to a cell expressing Notch, or, in the case of candidate proteins, can be provided by providing their encoding nucleic acids under conditions in which the nucleic acids are recombinantly expressed to produce the candidate proteins within the Notch expressing cell. In an embodiment of the invention directed to the assay using full-length Notch and a composition comprising cellular proteins, candidate molecules can also be added to a composition comprising cellular proteins (whole cell lysates, membrane fraction, etc.), preferably derived from cells endogenously or recombinantly expressing Notch.

This embodiment of the invention is well suited to screen chemical libraries for molecules which modulate, e.g., inhibit, antagonize, or agonize, Notch activation. The chemical libraries can be peptide libraries, peptidomimetic libraries, other non-peptide synthetic organic libraries, etc.

Exemplary libraries are commercially available from several sources (ArQule, Tripos/PanLabs, ChemDesign, Pharmacopoeia). In some cases, these chemical libraries are generated using combinatorial strategies that encode the identity of each member of the library on a substrate to which the member compound is attached, thus allowing direct and immediate identification of a molecule that is an effective modulator. Thus, in many combinatorial approaches, the position on a plate of a compound specifies that compound's composition. Also, in one example, a single plate position may have from 1–20 chemicals that can be screened by administration to a well containing the interactions of interest. Thus, if modulation is detected, smaller and smaller pools of interacting pairs can be assayed for the modulation activity. By such methods, many candidate molecules can be screened.

Many diversity libraries suitable for use are known in the art and can be used to provide compounds to be tested according to the present invention. Alternatively, libraries can be constructed using standard methods. Chemical (synthetic) libraries, recombinant expression libraries, or polysome-based libraries are exemplary types of libraries that can be used.

The libraries can be constrained or semirigid (having some degree of structural rigidity), or linear or nonconstrained. The library can be a cDNA or genomic expression library, random peptide expression library or a chemically synthesized random peptide library, or non-peptide library. Expression libraries are introduced into the cells in which the assay occurs, where the nucleic acids of the library are expressed to produce their encoded proteins.

In one embodiment, peptide libraries that can be used in the present invention may be libraries that are chemically synthesized in vitro. Examples of such libraries are given in Houghten et al., 1991, Nature 354:84–86, which describes mixtures of free hexapeptides in which the first and second residues in each peptide were individually and specifically defined; Lam et al., 1991, Nature 354:82–84, which describes a "one bead, one peptide" approach in which a solid phase split synthesis scheme produced a library of peptides in which each bead in the collection had immobilized thereon a single, random sequence of amino acid residues; Medynski, 1994, Bio/Technology 12:709–710, which describes split synthesis and T-bag synthesis methods; and Gallop et al., 1994, J. Medicinal Chemistry 37(9):1233–1251. Simply by way of other examples, a combinatorial library may be prepared for use, according to the methods of Ohlmeyer et al., 1993, Proc. Natl. Acad. Sci. USA 90:10922–10926; Erb et 15 al., 1994, Proc. Natl. Acad. Sci. USA 91:11422–11426; Houghten et al., 1992, Biotechniques 13:412; Jayawickreme et al., 1994, Proc. Natl. Acad. Sci. USA 91:1614–1618; or Salmon et al., 1993, Proc. Natl. Acad. Sci. USA 90:11708–11712. PCT Publication No. WO 93/20242 and Brenner and Lerner, 1992, Proc. Natl. Acad. Sci. USA 89:5381–5383 describe "encoded combinatorial chemical libraries," that contain oligonucleotide identifiers for each chemical polymer library member.

Further, more general, structurally constrained, organic diversity (e.g., nonpeptide) libraries, can also be used. By way of example, a benzodiazepine library (see e.g., Bunin et al., 1994, Proc. Natl. Acad. Sci. USA 91:4708–4712) may be used.

Conformationally constrained libraries that can be used include but are not limited to those containing invariant cysteine residues which, in an oxidizing environment, cross-link by disulfide bonds to form cystines, modified peptides (e.g., incorporating fluorine, metals, isotopic labels, are phosphorylated, etc.), peptides containing one or more non-naturally occurring amino acids, non-peptide structures, and peptides containing a significant fraction of γ-carboxyglutamic acid.

Libraries of non-peptides, e.g., peptide derivatives (for example, that contain one or more non-naturally occurring amino acids) can.also be used. One example of these are peptoid libraries (Simon et al., 1992, Proc. Natl. Acad. Sci. USA 89:9367–9371). Peptoids are polymers of non-natural amino acids that have naturally occurring side chains attached not to the alpha carbon but to the backbone amino nitrogen. Since peptoids are not easily degraded by human digestive enzymes, they are advantageously more easily adaptable to drug use. Another example of a library that can be used, in which the amide functionalities in peptides have been permethylated to generate a chemically transformed combinatorial library, is described by Ostresh et al., 1994, Proc. Natl. Acad. Sci. USA 91:11138–11142).

The members of the peptide libraries that can be screened according to the invention are not limited to containing the 20 naturally occurring amino acids. In particular, chemically synthesized libraries and polysome based libraries allow the use of amino acids in addition to the 20 naturally occurring amino acids (by their inclusion in the precursor pool of amino acids used in library production). In specific embodiments, the library members contain one or more non-natural or non-classical amino acids or cyclic peptides. Non-classical amino acids include but are not limited to the D-isomers of the common amino acids, α-amino isobutyric acid, 4-aminobutyric acid, Abu, 2-amino butyric acid; γ-Abu, ε-Ahx, 6-amino hexanoic acid; Aib, 2-amino isobutyric acid; 3-amino propionic acid; ornithine; norleucine; norvaline, hydroxyproline, sarcosine, citrulline, cysteic acid, t-butylglycine, t-butylalanine, phenylglycine, cyclohexylalanine, β-alanine, designer amino acids such as β-methyl amino acids, Cα-methyl amino acids, Nα-methyl amino acids, fluoro-amino acids and amino acid analogs in general. Furthermore, the amino acid can be D: (dextrorotary) or L (levorotary).

Further, toporythmic proteins, derivatives and fragments thereof, can be tested for the ability to modulate Notch activation. Toporythmic proteins, and more generally, members of the "Notch cascade" or the "Notch group" of genes, include Notch, Delta, Serrate, and other members of the Delta/Serrate family, which are identified by genetic (as detected phenotypically, e.g., in Drosophila) or molecular interaction (e.g., binding in vitro). See, International Publications WO 92/19734, WO 97/18822, WO 96/27610, and WO 97/01571 and references therein, for examples of vertebrate and non-vertebrate members of the Notch family of genes.

5.3 Heterodimeric Notch

The present invention is also directed to a substantially purified heterodimeric form of Notch comprising Notch fragments tethered together through a reducing agent-sensitive linkage, in particular, a non-covalent, metal ion-dependent (e.g., calcium ion-dependent) linkage. In its active state Notch is a heterodimer of an about (±10%) 180 kilodaltons (kDa) subunit ($N^{EC}$) and an about (±10%) 110 kDa subunit ($N^{TM}$), which are tethered together through a reducing agent-sensitive linkage, particularly, a non-covalent, metal ion-dependent (e.g., calcium ion-dependent) linkage. As shown by way of example infra, the two subunits arise due to a proteolytic cleavage of the full length Notch molecule in the trans-Golgi at a site in Notch amino-terminal to the transmembrane domain and carboxy-terminal to the EGF repeat region, thus generating an extracellular fragment ($N^{EC}$) of about 180 kDa and a transmembrane/intracellular fragment ($N^{TM}$) of about 110 kDa.

The present invention is also directed to an amino-terminal fragment of full-length Notch terminating between the epidermal growth factor-like repeat domain and the transmembrane domain (in particular, between the Lin-12/Notch repeats and the transmembrane domain) of full-length Notch. The present invention is also directed to a carboxy-terminal fragment of full-length Notch with its amino terminus situated between the epidermal growth factor-like repeat domain and the transmembrane domain (in particular, between the Lin-12/Notch repeats and the transmembrane domain).

Nucleic acids encoding vertebrate and non-vertebrate Notch have been cloned and sequenced. See, for example, WO 92/19734 and U.S. Pat. No. 5,648,464, which are incorporated by reference in their entirety herein; Wharton et al., 1985, Cell 43:567–581; and Coffman et al., 1990, Science 249:1438–1441. These nucleic acids can be used to express the full length Notch molecule either in vivo or in vitro, and either the full length molecule is isolated and then proteolytically cleaved (e.g., by exposure to cell lysates) or the full-length Notch is physiologically cleaved by the cell and the fragment(s) are then isolated therefrom. Also, the Notch encoding nucleic acids can be subcloned to express the two subunits $N^{EC}$ and $N^{TM}$, respectively, either in vivo or in vitro, which can then be isolated, and if desired, can then be tethered together by addition of, or in the presence of, $Ca^{2+}$ to form a non-covalent, metal ion-dependent, reducing agent-sensitive linkage.

The present invention is also directed to pharmaceutical compositions comprising the heterodimeric form of Notch, or the amino-terminal fragment, or the carboxy-terminal fragment, or mixtures thereof suitable for in vivo administration, in combination with a pharmaceutically acceptable carrier or excipient. Such a carrier includes but is not limited to saline, buffered saline, dextrose, water, glycerol, ethanol, and combinations thereof. The carrier and composition can be sterile. The formulation should suit the mode of administration.

The composition, if desired, can also contain minor amounts of wetting or emulsifying agents, or pH buffering agents. The composition can be a liquid solution, suspension, emulsion, tablet, pill, capsule, sustained release formulation, or powder. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc.

In a preferred embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration.

6. Intracellular Cleavage of Notch Leads to a Heterodimeric Receptor on the Plasma Membrane Previous models for signal transduction via the Notch pathway have depicted the full-length Notch receptor expressed at the cell surface. Evidence is presented herein demonstrating that the Notch receptor on the plasma membrane is cleaved. This cleavage is an evolutionary conserved, general property of Notch and occurs in the trans-Golgi network as the receptor traffics towards the plasma membrane. although full-length Notch is detectable in the cell, it does not reach the surface. Cleavage results in a C-terminal fragment, $N^{TM}$, which appears to be cleaved N-terminal to the transmembrane domain, and an N-terminal fragment $N^{EC}$ that contains most of the extracellular region. Evidence is provided herein that these fragments are tethered together on the plasma membrane by a link that is sensitive to reducing conditions and dependent upon the presence of metal ions, forming a heterodimeric receptor. On the basis of the experimental evidence gathered, it is proposed that the active, ligand accessible form of the receptor is the heterodimeric form, whereas full-length Notch reflects newly synthesized, intracellular and, hence, inactive molecules.

6.1 Materials and Methods

6.1.1 Isolating and Sequencing Human Notch2 cDNAs

A human fetal brain cDNA Zap II library (from 17–18 week embryo; Stratagene, La Jolla, Calif.) was used in the screening for human Notch homologs. The Notch cDNA clones were originally obtained by using a probe encoding portions of the human Notch2 protein (hN2K and hN5K), (Stifani et al., 1992, Nature Genetics 2:119–127). A probe used to screen for cDNAs spanning 5' regions of the human Notch2 gene was generated from the hN2K cDNA. Because the extreme 5' terminus of the human Notch2 gene was not isolated using this probe, advantage was taken of the fortuitous isolation of a human Notch2 cDNA (Adams, et al., 1993, Nature Genetics 4:256–267) that extends further 5', as determined by sequence comparison to the rat Notch2 cDNA isolated by Weinmaster et al., 1992, Development 116:931–941. Although this human cDNA does not extend to the extreme 5' end of the human Notch2 coding region, it was used to generate a new probe that was closer to the 5' end of the gene. This probe was used to isolate the 5'-most cDNAs encoding human Notch2. Sequencing was done using the Sequenase™ Kit (United States Biochemical Corporation, Cleveland, Ohio).

6.1.2 Cell Culture

Human neuroblastoma (SJ-NB5) cells were grown at 37° C. in an atmosphere of 5% $CO_2$/95% air, in RPMI (Gibco-BRL, Grand Island, N.Y.) supplemented with 10% fetal bovine serum (Gibco BRL, Grand Island, N.Y.), 2 mM L-Glutamine (ICN Biomedicals, Inc., Costa Mesa, Calif.), 100 µg/ml penicillin, and 100 µg/ml streptomycin (ICN Biomedicals, Inc., Costa Mesa, Calif.). Cells were dissociated using phosphate buffered saline (PBS) with 0.25% trypsin and 0.03% EDTA (J. T. Baker, Inc., Phillipsburg, N.J.), and subcultured at ratios of 1:3 to 1:10. HaCat Cells (cultured human keratinocytes) were a gift from Dr. Michael Reiss (Yale University). Aggregation experiments and the maintenance of Drosophila S2 and KC cells were as described in Fehon et al., 1990, Cell 61:523–534.

6.1.3 Antibodies

Antibodies bhN6D and bTAN20 are monoclonal antibodies (rat, IgG) directed against the non-conserved intracellular epitopes of human Notch2 and Notch1, respectively (Zagouras et al., 1995, Proc. Natl. Acad. Sci. USA 92:6414–6418). On western blots they recognize specifically Notch1 and Notch2 but are not useful for immunoprecipitations. In contrast, antibody PGHN, a polyclonal antibody (Rabbit, IgG) directed against intracellular epitopes of human Notch2, can be used to immunoprecipitate Notch2 (Zagouras et al., 1995, Proc. Natl. Acad. Sci. USA 92:6414–6418). The Drosophila antibody 9C6 is a monoclonal antibody which recognizes intracellular epitopes of Notch (Fehon et al., 1990, Cell 61:523–534).

6.1.4 Subcellular Fractionation and Western Blotting

SJ-NB5 cells were grown to 80–90% confluence in six T-75 tissue culture flasks, scraped in TBS, washed once and resuspended in 1 ml cold buffer A (75 mM KCl; 10 mM imidazole, pH 7.2; 1 mM EGTA; 2.5 MM $MgCl_2$; 0.02% $NaN_3$; 1 mM DTT; and 1 mM Pefabloc SC [Boehringer Mannheim]). During the fractionation process all samples were kept on ice and resuspended in cold buffer A. Pellet samples at all stages of fractionation were resuspended in their original volumes so that stoichiometric ratios of all samples would be equivalent.

Cells were homogenized using Omini's hand homogenizer with microscopic monitoring of cell lysis throughout homogenization. A 50 µl aliquot was kept as Fraction 1 (whole cell lysate). The lysate was then centrifuged at low speed (900×g) for 5 minutes at 4° C. The resulting pellet was resuspended in buffer A, with a 50 µl aliquot of the suspension as Fraction 2 (0.9K/P). The suspension was centrifuged again. The pellet was washed once with buffer A. After a third centrifugation, the pellet was resuspended in 200 µl buffer A, mixed with 1.8 ml 60% sucrose made in buffer A containing 5 mM $MgCl_2$, and then transferred to a Beckman SW 50.1 centrifuge tube. The suspension was overlaid with 2 ml 40% sucrose-buffer A, and then 2 ml buffer A. The sample was centrifuged at 100,000×g for 1 hr at 4° C. Two banded fractions were collected separately and 50 µl aliquots were kept. The upper and lower fractions were termed 40/0 and 40/50, respectively, and the nuclear pellet at bottom was resuspended in buffer A and designated NP.

The supernatant from the 900×g spin was centrifuged again at 40,000×g for 15 minutes at 4° C. using a Sorval SS-34 fixed angle rotor. The pellet from this mid-speed spin was resuspended in buffer A and designated 40K/P. The supernatant from the mid-speed spin was further centrifuged at 100,000×g for 1 hr at 4° C. using a Beckman 70 Ti fixed angle rotor. The pellet was again resuspended in buffer A and termed 100K/P. The supernatant was labeled 100K/S.

All samples were resuspended in 10× sample buffer, boiled and subjected to 4–20% SDS-PAGE, transferred to nitrocellulose and western blotted as described in Stifani et al., 1992, Nature Genetics 2:119–127. For western blotting, a culture supernatant of anti-human Notch2 antibody bhN6D, which recognizes the intracellular domain of human Notch2, was used at a dilution of 1:10.

6.1.5 Biotinylation

Cells were grown in 10 cm plastic tissue culture plates to ~80% confluence. Six plates were used per sample (+ or −biotin). Cells were washed four times with cold PBS/CMG (PBS/0.1 mM $CaCl_2$/1.0 MM $MgCl_2$/1.0 % glucose/pH~8.0). 1.7 ml of fresh, cold PBS/CMG+/−Sulfo-NHS-biotin was added to each plate, then incubated at 4° C. for 15 minutes with shaking. This solution was replaced with cold RPMI without serum to absorb excess biotin, and cells were pipetted off the plates in cold serum free RPMI medium and incubated at 4° C. for 15 minutes. The cells were washed three times in cold PBS/CMG solution, and were then lysed in 1.2 ml lysis buffer per sample as described in Zagouras et al., 1995, Proc. Natl. Acad. Sci. USA 92:6414–6418. After addition of SDS to 0.2%, the samples were divided into three equal portions (~400 μl each) for precipitation: 20 μl immobilized streptavidin (Immunopure Immobilized Streptavidin, Pierce, Rockford, Ill.); 2 μl anti-human Notch2 antibody PGHN (as described in Zagouras et al., 1995, Proc. Natl. Acad. Sci. USA 92:6414–6418), or 2 μl normal rabbit serum (NRbS) as a negative control. Samples were incubated overnight at 4° C. *Staphylococcus aureus* (Sigma Chemical Co., St. Louis, Mo.) was added to PGHN and NRbS samples at 80 μl per sample and incubations continued at 4° C. for 30 minutes. All samples were washed two times in 500 μl RIPA buffer A (10 mM Tris-HCl, pH 7.4/1% Triton X-100/0.1% SDS/1% Sodium Deoxycholate/150 mM NaCl) with 2.5 ug/ml antipain (Sigma Chemical Co., St. Louis, Mo.), 2.5 μg/ml aprotinin (Sigma Chemical Co., St. Louis, Mo.), 2 μM leupeptin (Sigma Chemical Co., St. Louis, Mo.), 2.5 μg/ml pepstatin (Sigma Chemical Co., St. Louis, Mo.), and 1 mM mg/ml phenylmethylsulfonyl fluoride (Sigma Chemical Co., St. Louis, Mo.). Samples were resuspended in 2×sample buffer, boiled, and subjected to SDS-polyacrylamide gel electrophoresis.

6.1.6 Pulse Chase and Brefeldin A Treatment

SJ-NB5 cells were grown on 60 mm petri dishes until ~80% confluent, washed once with PBS, and then incubated in methionine and cysteine free DMEM medium for 1 hr. 100 μCi $^{35}$S-translabled Met-Cys (ICN) was added to each plate, pulsed at 37° C. for 20 minutes, and chased for varying times and temperatures. The chase began by adding 2× volume complete medium plus 100 μg/ml cold methionine and cysteine to the plates.

For Brefeldin A samples, Brefeldin A was maintained at a final concentration of 10 μg/ml in starvation medium as well as in both pulse and chase. Cells were washed with cold PBS and lysed in lysis buffer (Zagouras et al., 1995, Proc. Natl. Acad. Sci. USA 92:6414–6418) containing 1 mM Pefabloc SC, 0.7 μg/ml pepstatin A, and 0.5 μg/ml leupeptin. Cell lysates were centrifuged at 14,000 rpm for 5 minutes. The supernatants were transferred to fresh tubes and precleared by incubating with 5 μl normal rabbit serum and 50 μl 10% protein A-sephrose CL-4B (Pharmacia LKB) for 1 hr at 4° C. The beads were pelleted by centrifugation and the supernatants were divided into two equal aliquots. One aliquot was immunoprecipitated by incubating with rabbit polyclonal anti-human Notch2 antibody PGHN and 50 μl protein A-sephrose CL-4B for 2–3 hrs or overnight at 4° C. The other aliquot was immunoprecipitated by normal rabbit serum as control. The beads were washed three times in RIPA buffer B (150 mM NaCl, 1% NP40, 0.5% DOC, 0.1% SDS, 50 mM Tris, pH 7.5); washed once in 50 mM Tris-Cl, 150 mM NaCl, pH 7.5; resuspended in 50 μl SDS-sample buffer; boiled; and subjected to a 3–15% gradient SDS-PAGE gel. The gel was fixed in 25% iso-propanol, 10% acetic acid for 30 minutes, soaked in Amplify™ (Amersham) for 15–30 minutes, dried, and exposed to X-ray film at −70° C.

6.1.7 Pulse Chase and Biotinylation

SJ-NB5 cells were grown on 100 mm petri dishes until ~80% confluent and pulse chased as described in Section 6.1.6 above. The pulse-chase times shown are described in the description of the figures. After pulse-chase, the plates were put on ice, washed three times in cold PBS (containing 0.1 mM $CaCl_2$, 1 mM $MgCl_2$), and then incubated 30 minutes at 4° C. in 2 ml biotinylation buffer (10 mM triethanolamine, pH 9.0, 2 mM $CaCl_2$, and 150 mM NaCl) containing 1 mg/ml NHS-SS-Biotin (Pierce, Rockford, Ill.) (freshly diluted from a 200 mg/ml DMSO stock stored at −20° C.) with very gentle shaking, and subsequently incubated in PBS-CMG buffer (0.1 mMCaCl$_2$, 1 mM MgCl$_2$, 100 mM Glycine) for another 30 minutes to quench unreacted biotin. Post incubation plates were washed twice in PBS-CM buffer to wash away the quenched biotin. Finally, the cells were lysed and immunoprecipitated by PGHN as previously described. After the final wash, the beads were divided equally into two aliquots. One aliquot was boiled in SDS-sample buffer, the second aliquot was incubated in 100 μl elution buffer (1% SDS, 50 mM Tris-Cl, 150 mM NaCl, pH 7.5) at 80° C. for 10 minutes, then 900 μl of lysis buffer was added to the eluted protein. After centrifugation, the supernatant was transferred to a fresh tube containing 50 μl of packed streptavidin beads (Pierce, Rockford, Ill.), and incubated at 4° C. for 2–3 hrs. The beads were washed and boiled in SDS-sample buffer as described above. The samples were analyzed by 3–15% SDS-PAGE electrophoresis. The gel was fixed in 25% iso-propanol, 10% acetic acid for 30 minutes, soaked in Amplify (Amersham) for 15–30 minutes, dried, and exposed to X-ray film at −70° C.

6.2 Characterization of the Human Notch2 Gene

The full-length cDNA encoding the human Notch2 protein is 7.8 kb in length, and the predicted protein product is 2471 amino acids long. This protein has all of the expected domains of Notch family proteins and is 92% identical to the rat Notch2 amino acid sequence overall. An amino acid alignment of human Notch2 (SEQ ID NO:1) with human Notch1 (SEQ ID NO:2), Xenopus Notch (Xotch) (SEQ ID NO:3) and Drosophila Notch (SEQ ID NO:4) is shown in FIGS. 2A–2D.

36 EGF repeats are present in all of the proteins shown, and each is more closely related to the corresponding EGF repeat in the other Notch homologs than to neighboring EGF repeats within the same protein. The overall identity for the EGF repeat region between the human Notch paralogs is 59%, while the identity levels between the Drosophila and human proteins in this region are slightly lower (51% for human Notch1 and 52% for human Notch2). While the overall amino acid conservation across the EGF repeat domain is low, the conservation of individual EGF repeats from one protein to another is variable (M. Baron and S. Artavanis-Tsakonas, unpublished results). Certain repeats, including numbers 11 and 12, which are capable of ligand-binding (Rebay et al., 1991, Cell 67:687–699), are more highly conserved than others. The overall conservation of the LN repeats is similar to that for the EGF repeats, having 54% identity between the human homologs and slightly lower values between Drosophila Notch and either human Notch1 or human Notch2 (49% and 44%, respectively).

In Notch2, the conservation of the intracellular domain is high. All of the known structural hallmarks of the Notch proteins are maintained, including the Ankyrin repeats, the PEST-containing region, and the basic stretch of amino acids which can function-as nuclear localization signals and target truncated forms of the protein into the nucleus (Stifani et al., 1992, Nature Genetics 2:119–127; Lieber et al., 1993, Genes and Development 7:1949–1965).

6.3 The Notch2 Protein Is Cleaved

Antibodies raised specifically against the human Notch2 protein were used to study its expression in cultured cells (Antibody bhN6D). Western blotting of Notch2 protein from the human SJ-NB5 neuroblastoma cell line revealed the presence of an approximately 110 kD ($N^{TM}$) polypeptide in addition to the full-length 300 kD protein (FIG. 3A, lane 1). This lower molecular weight polypeptide is the predominant species recognized by the antibody used in this experiment. A similar processing pattern is seen in HaCat cells (FIG. 3A, lane 2), a human keratinocyte cell line. The observed processing pattern is not confined to cell lines. The predominant polypeptide species recognized by the same antibody in rat embryo extracts and in a variety of human tissue extracts is also the 110 kD Notch breakdown product (FIG. 3A, lane 3, and FIG. 3B). Note that this western blot analysis reveals differences in the relative ratio of the full-length protein and the $N^{TM}$ derivative among the examined tissues.

6.4 Cleavage Is a General Property of the Notch Receptor

Whether the characteristic cleavage pattern of the human Notch2 paralog is peculiar only to this molecule or whether it reflects a general pattern for the Notch receptor family was examined. Western blot analysis, using an antibody raised against the human Notch1 paralog (antibody bTAN20), demonstrates that this protein displays a processing pattern that is similar to that of Notch2 (FIG. 3C and FIG. 3D). These results are compatible with earlier analyses involving Notch1. The existence of a prominent approximately 120 kD fragment was previously demonstrated in extracts of two different human cell lines that express the Notch1 paralog (Aster et al., 1994, Cold Spring Harbor Symposia on Quantitative Biology 59:125–136). When a Notch1 expression plasmid is transfected into a baby hamster kidney cell line (BHK cells), the major Notch peptide detected in these cells by western blot analysis is a 110 kD species (data not shown, and Zagouras et al., 1995, Proc. Natl. Acad. Sci. USA 92:6414–6418).

In order to determine whether the processing pattern seen for Notch1 and Notch2 is specific to mammalian Notch proteins, western blotting of Drosophila cell lysates was performed, using an antibody raised against intracellular epitopes of Drosophila Notch (FIG. 3E; Fehon et al., 1990, Cell 61:523–534). In an embryonic extract, in addition to the clearly detectable full-length protein, several smaller Notch polypeptides, including an approximately N band, are visible. In the KC cell line, which expresses Notch endogenously, $N^{TM}$ is clearly detectable. Finally, in an S2 cell line, which does not express endogenous Notch but has been stably transfected with a Notch expression plasmid, $N^{TM}$ is also prominent. It is concluded that the processing of the Notch receptor is a general property of the Notch proteins.

6.5 $N^{TM}$ Is Associated with Membranes

The subcellular localization of the Notch polypeptides was determined by cell fractionation. SJ-NB5 cells were fractionated as described in Section 6.1 and the resulting fractions were examined by western blotting. FIG. 4 shows a fractionation experiment in which the $N^{TM}$ Notch fragment is associated with membrane lanes. Each fraction was also tested for the presence of syntaxin, a plasma membrane protein expressed in the same cell line (Bennett et al., 1992, Science 257:255–259). In order to ensure that such fractionation pattern is not confined to the SJ-NB5 cell line, HaCat cells and Drosophila S2 cells that were stably transfected with a Notch expression plasmid were fractionated (data not shown) and similar results were obtained.

6.6 The Notch Receptor Presented at the Cell Surface Is Cleaved

The association of the $N^{TM}$ Notch fragment with the plasma membrane was further examined by biotin labeling of live SJ-NB5 cells (FIG. 5). Biotin labeling of surface proteins was performed by incubating live cells on ice in medium containing biotin (control cells were treated with the same medium lacking biotin). The cells were subsequently lysed and divided into three equal portions that were incubated with the following reagents: (1) immobilized streptavidin, which precipitates only biotin-labeled proteins, (2) the anti-Notch2 antibody PGHN, a polyclonal antibody which recognizes an intracellular epitope and immunoprecipitates human Notch2 (Zagouras et al., 1995, Proc. Natl. Acad. Sci. USA 92:6414–6418), and (3) normal rabbit serum (NRbS). Western blotting of the precipitated products was performed using the anti-Notch2 antibody, bhN6D. The results of this experiment are shown in FIG. 5. The only Notch2-related surface protein that was detected is the $N^{TM}$ breakdown product. Immobilized streptavidin precipitated only the $N^{TM}$ product in the biotin-labeled samples (lane 1) and no protein in the unlabeled samples (lane 4). In contrast, anti-Notch2 antibody PGHN efficiently precipitated both the full-length and breakdown Notch2 products in biotinylated (lane 2) and non-biotinylated samples (lane 5).

As expected, the negative control, NRbS, does not precipitate either protein form (lanes 3 and 6).

Based on the above results it is concluded that the $N^{TM}$ fragment is a transmembrane Notch polypeptide that resides on the plasma membrane and must be the result of a cleavage at a site in the extracellular domain.

6.7 Notch Is Cleaved in the Trans-Golgi Network Before Reaching the Surface

The experiments described above demonstrate that the steady state form of the Notch receptor found at the cell surface is a cleaved form. In an attempt to determine the cellular compartment where Notch is cleaved, pulse labeling analyses were carried out in the presence of drugs that are known to interfere with cellular trafficking. FIG. 6A demonstrates that Brefeldin A, which blocks transport between the cis- and trans-Golgi network, effectively blocks the breakdown of full-length Notch. In contrast, monensin or chloraquinone do not affect processing (data not shown). Cleavage is also effectively blocked at 19° C., a characteristic feature of processing events that occur in the trans-Golgi network (FIG. 6B).

6.8 The Cleaved Extracellular Domain of Notch Is Tethered to the $N^{TM}$ Transmembrane Fragment In the aforementioned pulse labeling experiments (FIGS. 6A–6B), the accumulation of the $N^{TM}$ fragment is closely paralleled by the accumulation of a larger fragment that is approximately 180 kD in molecular weight. This larger fragment is co-immunoprecipitated by the antibody PGHN, which recognizes an intracellular epitope of human Notch2. However, blotting of the same immunoprecipitate by western blot, using antibody bhN6D, also raised against an intracellular epitope, detects only the $N^{TM}$ fragment.

A single cleavage of the Notch protein that produces a 110 kD fragment would also generate a second fragment of approximately 180 kD. It was therefore presumed that the $N^{EC}$ fragment, which accumulates with kinetics indistinguishable from those of $N^{TM}$, corresponds to the cleaved extracellular domain of the Notch2 protein that remains attached to the $N^{TM}$ polypeptide by a SDS and/or DTT sensitive linkage. Antibodies recognizing extracellular epitopes were not possessed by us for western blot analysis. However, the relatedness of these fragments is also supported by the fact that the appearance of $N^{EC}$ is not inhibited by monensin or chloraquinone (data not shown) but is inhibited by Brefeldin A and a 19° C. block (FIG. 6A). Additional supporting evidence comes from pulse labeling experiments done with a cysteine rather than a methionine label. Labeling with cysteine shows that the $N^{EC}$ band incorporates nearly an order of magnitude more label than the $N^{TM}$ band, consistent with the hypothesis that it carries most of the Notch extracellular domain (data not shown).

Additional biochemical data shows that the tethering of $N^{EC}$ to $N^{TM}$ is not only reducing agent-sensitive but is also metal ion-dependent. FIG. 11A is a Western blot analysis demonstrating that $N^{EC}$ is present in the supernatant of Notch expressing S2 cells that have been resuspended in 2 mM EDTA, Tris-HCl saline buffer (EDTA), whereas in the presence of 2 mM $CaCl_2$ ($Ca^{2+}$) insignificant amounts of $N^{EC}$ are detected. Briefly, Drosophila S2 cells were induced to express Notch with the addition of 0.7 mM $CuSO_4$ for 16 hours; Notch expression was under the control of the metallothionien promoter (Fehon et al., 1990, Cell 61:523–534). The cells were washed once with 20 mM Tris-HCl, 150 mM NaCl, 2 mM $CaCl_2$ ($TBS/Ca^{2+}$) and were resuspended in $TBS/Ca^{2+}$ or in 20 mM Tris-HCl, 150 mM NaCl, 2 mM EDTA (TBS/EDTA) and incubated for one hour at room temperature under slow rocking. The cells were centrifuged and pelleted and the supernatants were collected for SDS-PAGE and Western blot analysis. The blot was probed with a monoclonal antibody directed to the extracellular domain of Notch, specifically against EGF-like repeats 5–7 of Drosophila Notch (clone C461.3B). This monoclonal was detected using goat anti-mouse horseradish peroxidase secondary antibody and chemiluminescent substrate.

FIG. 11B is a Western blot of a sucrose density centrifugation of S2 cell extracts that shows $N^{EC}$ and $N^{TM}$ co-sediment in the presence of $CaCl_2$, whereas $N^{EC}$ and $N^{TM}$ sediment separately in the presence of EDTA. Briefly, S2 expressing Notch cell extracts were prepared in either TBS/$Ca^{2+}$ or TBS/EDTA with 1% Triton X-100, a non-ionic detergent, 1 mM PMSF, Pepstatin and Aprotinin each at 2 $\mu$g/mL and 1.8 $\mu$M Leupeptin. The extracts were sedimented through a 5–20% sucrose gradient in the above-respective buffers (without the protease inhibitors) in a Beckman SW50.1 rotor at 34,000 rpm for 16 hours at 4° C. Fractions were collected and precipitated with 10% trichloroacetic acid. The protein pellets were resuspended in SDS-PAGE sample buffer and analyzed by SDS-PAGE and Western blotting. Blots were probed with a mixture of monoclonal antibodies C461.3B and 9C6 (directed against the intracellular domain of Notch) and detected as described above.

These data demonstrate that $N^{EC}$ and $N^{TM}$ dissociate in the presence of calcium ion chelators such as EDTA and EGTA. Other evidence (not shown) shows that dissociated $N^{EC}$ and $N^{TM}$ can reassociate upon addition of calcium. Moreover, the interaction is sensitive to reducing agents such as β-mercaptoethanol and dithiothreitol (DTT), which are likely to act by disrupting the intra-chain disulfide bonds necessary to provide the secondary structure necessary for the Notch inter-chain interactions.

These data demonstrate that $N^{EC}$ and $N^{TM}$ are tethered through a non-covalent, metal ion-dependent, reducing agent-sensitive linkage, not through a disulfide bridge. Although the interaction between $N^{EC}$ and $N^{TM}$ does not appear to be dependent on inter-chain disulfide bond(s), intra-chain disulfide bond(s) appear to play a role in maintaining secondary structure such that $N^{EC}$ and $N^{TM}$ are able to interact.

6.9 Full Length Notch does not Reach the Cell Surface

The western blot analyses revealing the existence of the $N^{TM}$ Notch fragment (FIG. 3) also show varying amounts of full-length Notch. Therefore, the fate of the full-length molecule was explored by testing its expression at the cell surface.

SJ-NB5 cells were labeled with [$^{35}$S]-methionine for 10 minutes and then chased for varying periods. The live cells were incubated with Biotin as described above, subsequently lysed, and immunoprecipitated with PGHN. The immunoprecipitate was divided into two equal portions, one of which was re-precipitated with immobilized streptavidin. The two sets of samples were then examined by SDS gel electrophoreses followed by fluorography. FIG. 7 shows that negligible amounts of full-length Notch are detected on the surface throughout the chase, while substantial amounts of full-length molecules are precipitated by the Notch antibody (total cellular Notch). As the full-length, newly synthesized Notch decreases during the chase, the $N^{TM}$ fragment begins to accumulate in the streptavidin precipitated reaction. $N^{TM}$ accumulation is paralleled by the appearance of the $N^{EC}$ fragment, consistent with the contention that this fragment represents the extracellular domain of Notch and is tethered to the $N^{TM}$ Notch polypeptide. It is concluded that Notch protein reaches the surface in a cleaved form and that newly synthesized full-length Notch is not found on the plasma membrane.

6.10 Notch Heterodimers Bind the Ligand Delta

The biological significance of the heterodimeric Notch form would be questionable if it could not bind ligands. Physical interaction between the extracellular domains of Notch and Delta have been demonstrated with the help of aggregation assays involving Delta and Notch expressing cells. If the heterodimeric form interacts with Delta after aggregation then the 110 kd $N^{TM}$ fragment should co-immunoprecipitate using Delta antibodies. It was found that after aggregation, Delta antibodies are capable of efficiently immunoprecipitating the $N^{TM}$ fragment demonstrating that the heterodimeric form can bind Delta (FIG. 8). As expected, if the aggregation is disrupted by depleting calcium from the medium by EGTA (Fehon et al., 1993, Cell 61:523–534). Delta antibodies fail to efficiently precipitate $N^{TM}$ (data not shown).

6.11 Discussion

The strong structural conservation among both the Drosophila and vertebrate Notch gene products, and among homologs of other components of the same pathway, imply that the molecular and biochemical mechanisms involved in Notch signaling are conserved across species boundaries. The question of what particular roles are played by the assortment of paralogs within the Notch superfamily, in combination with the various paralogs of the other pathway components, remains unclear. Expression pattern comparisons, structural similarities and the available functional data for distinct paralogs suggest that these molecules possess different expression profiles but similar biochemical and developmental properties.

It has been found that the human Notch2 protein is a highly conserved member of the Notch protein family. Specific Notch EGF repeats have been implicated in protein interactions, and missense mutations in both Drosophila and humans have been associated with mutant phenotypes (Hartley et al., 1987, EMBO J. 6:3407–3417; Kelley et al., 1987, Cell 51:539–548; Rebay et al., 1991, Cell 67:687–699; Joutel et al., 1996, Nature 383:707–711). Functional data regarding the cysteine rich LN repeats are lacking. Nevertheless, all Notch homologs, from flies to humans, share similar LN repeat stretches in the equivalent extracellular region of the receptor. Within the intracellular domain of the Notch proteins, all six of the Ankyrin repeats are highly conserved. These repeats have been shown to play a crucial role in Notch signaling and have been implicated in molecular interactions between Drosophila Notch and the Deltex protein, which behaves as a positive regulator of Notch activity (Matsuno et al., 1995, Development 121:2633–2644), and with the downstream effector Suppressor of Hairless (Fortini and Artavanis-Tsakonas, 1994, Cell 79:273–282; Matsuno et al., 1995, Development 121:2633–2644). Consistent with the high degree of conservation, Notch2 Ankyrin repeats were found to interact both with Drosophila as well as with human Deltex (K. Matsuno and S. Artavanis-Tsakonas, unpublished observations).

The biochemical evidence presented herein shows that the Notch receptor is cleaved in the trans-Golgi network before reaching the cell surface. Pulse labeling experiments in combination with the biotinylation data indicate that the full-length Notch molecule does not reach the plasma membrane. The varying amounts of full-length Notch detected in different cell extracts presumably reflects a newly synthesized, inactive receptor that has not yet reached the Golgi and is inaccessible to ligands. Several lines of evidence indicate that this cleavage is a general property of cellular Notch. First, the same cleavage pattern is seen in all human cell lines and human tissues examined. Second, both Notch1 and Notch2 are processed in the same way. Third, the cleavage product $N^{TM}$ is seen in both freshly prepared embryonic rat tissues as well as in Drosophila extracts.

The subcellular fractionation and biotinylation studies demonstrate that $N^{TM}$ is associated with the plasma membrane, indicating a cleavage in the extracellular region of Notch. The epitope recognized by the antibodies used here was raised against the least conserved region of the intracellular domain mapping between the PEST sequence and the Ankyrin repeats (Zagouras et al., 1995, Proc. Natl. Acad. Sci. USA 92:6414–6418). Hence, $N^{TM}$ must include the intracellular Notch2 sequences mapping between this C-terminal epitope and the transmembrane domain. It is likely the C. elegans Notch-like receptors lin-12 and glp-1 are cleaved in an analogous fashion, since N-terminal and C-terminal fragments of glp-1 were found to co-purify (Crittenden et al., 1994, Development 120:2901–2911). A deletion analysis involving Notch1 expression constructs transfected in cell lines by Aster et al., 1994, Cold Spring Harbor Symposia on Quantitative Biology 59:125–136, led them to suggest that, under their experimental conditions, Notch1 may be cleaved between the LN repeats and the transmembrane domain. It is noted that in the extracts examined herein, the main Notch1 Notch processing product in SJ-NB5 and HaCat cells is, as in Notch2, approximately 110 kD. In rat embryos, however, the main cleavage product appears to be larger. The significance of such qualitative differences in the processing pattern, or the additional breakdown products detected in our western blots, remains to be determined.

The accumulated evidence strongly indicates that $N^{EC}$ contains the cleaved extracellular sequences of Notch, even though the lack of appropriate antibodies prevents one from directly demonstrating this hypothesis. The kinetics of $N^{EC}$ accumulation and its inhibition profile are identical to $N^{TM}$. The molecular weights of the Notch breakdown products, as argued above, are also compatible with such notion. Finally, the relative incorporation of radioactive cysteine in the two fragments reflects the approximately 10:1 ratio predicted by the amino acid composition of two fragments produced by a cleavage such that $N^{EC}$ has most of the extracellular domain. In this regard, it is noteworthy that extracellular Notch fragments are present in the conditioned medium of Drosophila cell cultures that express Notch (Rebay, 1993, Ph.D. Thesis Yale University; I. Rebay, R. Fehon and S. Artavanis-Tsakonas, unpublished observations). Immunocytochemical studies with Drosophila tissues do not reveal differences in the cellular distribution of the intracellular vs. the extracellular domain of Notch (R. Fehon and S. Artavanis-Tsakonas, unpublished observations).

The co-precipitation of the $N^{EC}$ fragment together with $N^{TM}$, and the simultaneous appearance of the two fragments on the plasma membrane, indicate that $N^{EC}$ and $N^{TM}$ are tethered to one another. The inability to detect full-length Notch on the surface indicates that the cleaved form is the active form of the receptor.

Tethering of $N^{TM}$ to $N^{EC}$ is compatible with both the assumed mode of action of Notch, which necessitates interactions between the extracellular domains of the Notch receptor and its ligands, and with the cell autonomous nature of Notch signaling (Stern and Tokunaga, 1968, Proc. Natl. Acad. Sci. USA 60:1252–1259; Markopoulou et al., 1990, Journal of Experimental Zoology 27:23–27; Hoppe and Greenspan, 1990, Development 109:875–885; Heitzler and Simpson, 1991, Cell 64:1083–1092). On the other hand, any model of Notch biochemical activity and cellular function must take into account that Notch is cleaved. Several questions raised by this finding are worth pointing out. The possibility that $N^{EC}$ may be released from the surface, acting as an inhibitor of the pathway, must be further examined, especially in view of reports that have appeared in the literature over the years suggesting that Notch may have non-autonomous activities (Gehring, 1973, In Genetic Mechanisms of Development: The 31st Symposium of the Society for Developmental Biology. (New York: Academic Press Inc.); Technau et al., 1987, Proc. Natl. Acad. Sci. USA:84, 4500–4504; Baker and Schubiger, 1996, Development 122:617–626). Such a scenario must take into account that the expression of truncated forms of Notch, approximately corresponding to the postulated structure of $N^{TM}$, results in the constitutive activation of the receptor (Ellisen et al., 1991, Cell 66:649–661; Kopan et al., 1994, Development 120:2385–2396; Jennings et al., 1994, Development 120:3537–3548; Sun and Artavanis-Tsakonas, 1996, Development 122:2465–2474).

The notion that alterations in the extracellular domain may facilitate signaling events has been proposed on the basis of studies involving the expression of engineered constructs in cultured cells (Kopan et al., 1996, Proc. Natl. Acad. Sci. USA 93:1683–1688). Irrespective of how well these studies reflect the in vivo situation, together with the well documented in vivo action of truncated forms of Notch, they do raise the possibility that a ligand-dependent degradation or cleavage of the extracellular domain may result in the activation of the receptor. However, it seems unlikely that signaling would involve a simple ligand-dependent "shedding" of $N^{EC}$. For instance, cell adhesion mediated by Notch/Ligand interactions has been shown to trigger an endocytic flow of Delta molecules in the Notch expressing cells, where it is eventually found in multivesicular bodies (Fehon et al., 1990, Cell 61:523–534; R. Fehon and S. Artavanis-Tsakonas, unpublished results). Detailed expression studies of Delta expression in cells known to undergo Notch signaling are consistent with the cell culture findings (Kooh et al., 1993, Development 117:493–507). At this stage it seems that the simplest working hypothesis on Notch signaling should involve the heterodimeric ($N^{EC}/N^{TM}$) surface Notch complex proposed here, rather than the action of any single cleaved fragment (see the proposed model in FIG. 9). The negative complementation displayed by the Abruptex mutation, a group of gain-of-function mutants affecting amino acids in the EGF homologous region of Notch, has been thought to reflect homotypic interactions between Notch receptors (Foster, 1975, Genetics 81:99–120; Xu et al., 1990, Genes Dev. 4:464–475). Therefore akin, for example, to the insulin receptor, the $N^{EC}/N^{TM}$ heterodimer may be engaged in homotypic, or conceivably heterotypic, interactions. The analysis of the Notch receptor on nonreducing gels is consistent with this notion. In the absence of reducing agents, $N^{EC}$ and $N^{TM}$ are not detected. However, instead of detecting the full length molecule we detect higher molecular weight complexes of a yet undetermined nature (data not shown).

Since full-length Notch appears to reflect a ligand inaccessible, intracellular form of the protein, cleavage provides an important tool to regulate the Notch pathway. Such cleavage can effectively control the number of active surface receptors. Genetic analysis in Drosophila has demonstrated that the animal is unusually sensitive to the number of wild type copies of the Notch gene. In fact, Notch is one of a handful of genes in Drosophila that are both haplo insufficient as well as triplo mutant (Lindsley and Zimm, 1992, The genome of *Drosophila melanogaster*, (Academic Press, San Diego).

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims.

Various publications are cited herein, the disclosures of which are incorporated by reference in their entireties.

What is claimed is:

1. A method for detecting or measuring the form of Notch that mediates Notch signal transduction in a sample of cells comprising detecting or measuring the expression of a Notch heterodimer containing a reducing agent-sensitive linkage on the surface of cells in said cell sample, in which the heterodimer consists of an amino-terminal fragment of full-length Notch terminating between the epidermal growth factor-like repeat domain and the transmembrane domain of full-length Notch, and a carboxy-terminal fragment of full-length Notch with its amino terminus situated between the epidermal growth factor-like repeat domain and the transmembrane domain, and comparing said detected or measured expression to the detected or measured expression of full length Notch in said cells, wherein the presence and amount of Notch on the surface of said cells compared to the presence and amount, respectively, of full length Notch in said cells indicates the relative presence and amount, respectively, of the form of Notch that mediates Notch signal transduction.

2. The method according to claim 1 in which the amino-terminal fragment of full-length Notch terminates between the Lin-12/Notch repeats and the transmembrane domain, and the carboxy-terminal fragment of full-length Notch has its amino terminus situated between the Lin-12/Notch repeats and the transmembrane domain.

3. The method according to claim 1 in which the reducing agent sensitive linkage is a non-covalent, metal ion-dependent sensitive linkage.

4. The method according to claim 1 in which the heterodimer consists of $N^{EC}$ and $N^{TM}$.

5. A method for detecting or measuring the form of Notch that mediates Notch signal transduction in a sample of cells comprising detecting or measuring the expression of a Notch heterodimer containing a reducing agent-sensitive linkage in said cells, and comparing said detected or measured expression of Notch heterodimer to the detected or measured expression of full length Notch in said cells, wherein the presence and amount of said Notch heterodimer compared to the presence and amount, respectively, of full length Notch in said cells indicates the relative presence and amount, respectively, of the form of Notch that mediates Notch signal transduction, in which the heterodimer consists of $N^{EC}$ and $N^{TM}$.

6. The method according to claim 5 in which the reducing agent-sensitive linkage is a non-covalent, metal ion-dependent sensitive linkage.

* * * * *